(12) United States Patent
Hoeg-Jensen et al.

(10) Patent No.: US 11,541,122 B2
(45) Date of Patent: Jan. 3, 2023

(54) GLUCOSE SENSITIVE INSULINS AND USES THEREOF

(71) Applicant: Ziylo Limited, Gatwick (GB)

(72) Inventors: Thomas Hoeg-Jensen, Broenshoej (DK); Alice Ravn Madsen, Roedovre (DK); Thomas Kruse, Herlev (DK); Per Sauerberg, Farum (DK); Anthony Murray, Charlottenlund (DK); Andrew Michael Chapman, Bristol (GB); Anthony Peter Davis, Bristol (GB)

(73) Assignee: ZIYLO LIMITED

(*) Notice: Subject to any disclaimer, the term of this patent is extended or adjusted under 35 U.S.C. 154(b) by 80 days.

(21) Appl. No.: 17/274,802

(22) PCT Filed: Sep. 18, 2019

(86) PCT No.: PCT/EP2019/074987
§ 371 (c)(1),
(2) Date: Mar. 10, 2021

(87) PCT Pub. No.: WO2020/058322
PCT Pub. Date: Mar. 26, 2020

(65) Prior Publication Data
US 2022/0047708 A1     Feb. 17, 2022

(30) Foreign Application Priority Data

Sep. 19, 2018 (EP) .................................. 18195490
May 28, 2019 (EP) .................................. 19176911

(51) Int. Cl.
*A61K 47/55* (2017.01)
*C07K 14/62* (2006.01)
*A61P 5/50* (2006.01)

(52) U.S. Cl.
CPC .............. *A61K 47/55* (2017.08); *A61P 5/50* (2018.01); *C07K 14/62* (2013.01)

(58) Field of Classification Search
None
See application file for complete search history.

(56) References Cited

U.S. PATENT DOCUMENTS

| | | |
|---|---|---|
| 5,180,481 A | 1/1993 | Carey |
| 10,800,747 B2 | 10/2020 | Davis et al. |
| 2020/0017454 A1 | 1/2020 | Davis et al. |
| 2020/0399232 A1 | 12/2020 | Davis et al. |

FOREIGN PATENT DOCUMENTS

| | | | |
|---|---|---|---|
| JP | H04120049 A | 4/1992 | |
| WO | 9951570 A1 | 10/1999 | |
| WO | 2010107520 | 9/2010 | |
| WO | WO-2010107520 A1 * | 9/2010 | ............. A61K 38/28 |
| WO | 2013160701 A1 | 10/2013 | |
| WO | 2016149222 A2 | 9/2016 | |
| WO | 2018167503 | 9/2018 | |
| WO | WO-2018167503 A1 * | 9/2018 | ........... C07D 259/00 |

OTHER PUBLICATIONS

Davis et al., Carbohydrate Recognition Through Noncovalent Interactions: A Challenge for Biomimetic and Supramolecular Chemistry, Angew Chem. Int. Ed., 1999, vol. 38, pp. 2978-2996.
Maverick et al. "Torsional Motion in (tert-Butyl) ammonium Hemispheraplexes: Rotational Barriers and Energy of Binding." Helvetica chimica acta, 2003, vol. 86, No. 5, pp. 1309-1319.
Barwell et al., "A Synthetic Lectin for b-Glucosyl", Angewandte Chemie, Sep. 2009, vol. 48, pp. 7673-7676.
Snellink-Ruel et al., "Neutral Anion Receptors with Multiple Urea-Binding Sites", European Journal of Organic Chemistry, Dec. 13, 1999, vol. 2000, No. 1, pp. 165-170.
"Product Class 8: Acyclic and Cyclic Ureas", Science of Synthesis, 2005, vol. 18, p. 679-680.
Rajashree S. Hirlekar et al., "Oral insulin delivery: novel strategies", Asian Journal of Pharmaceutics, Oct. 2017, vol. 11, No. 3, pp. S434-S443.

* cited by examiner

*Primary Examiner* — Christina Bradley
(74) *Attorney, Agent, or Firm* — Jianjie Hu

(57) ABSTRACT

The present invention provides glucose sensitive insulin derivatives comprising a macrocycle, a glucose mimetic and human insulin or an analogue thereof, and their pharmaceutical use. Furthermore, the invention relates to pharmaceutical compositions comprising such glucose sensitive insulin derivatives, and to the use of such compounds for the treatment or prevention of medical conditions relating to diabetes.

23 Claims, 3 Drawing Sheets

Specification includes a Sequence Listing.

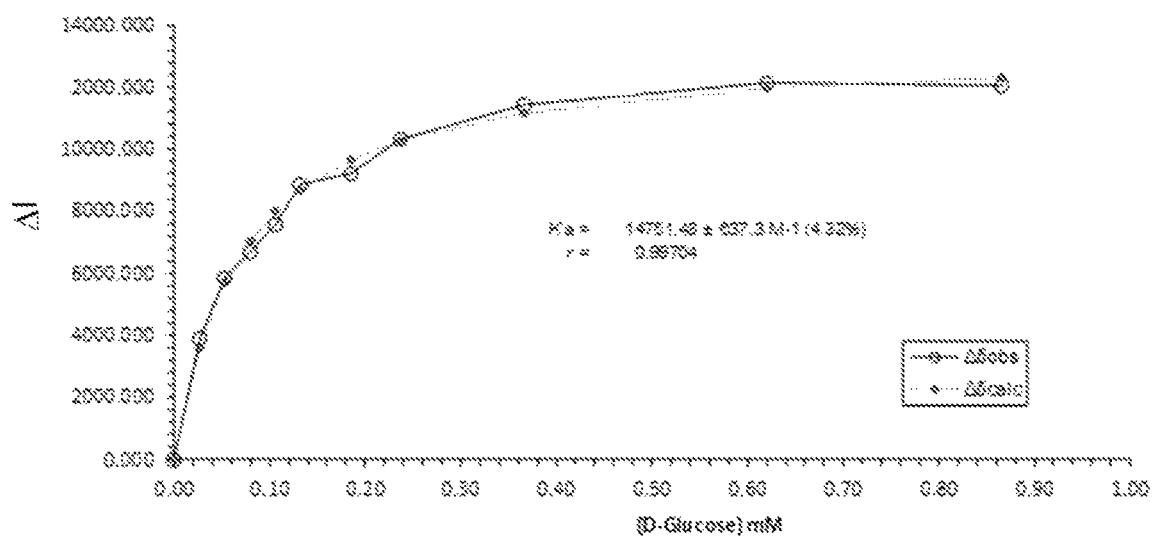
Fig. 3/3

SEQUENCE LISTING

<160> NUMBER OF SEQ ID NOS: 3

<210> SEQ ID NO 1
<211> LENGTH: 21
<212> TYPE: PRT
<213> ORGANISM: Artificial Sequence
<220> FEATURE:
<223> OTHER INFORMATION: human insulin A-chain

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 2
<211> LENGTH: 30
<212> TYPE: PRT

```
<213> ORGANISM: Artificial Sequence
<220> FEATURE:
<223> OTHER INFORMATION: Human insulin B-chain

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 3
<211> LENGTH: 29
<212> TYPE: PRT
<213> ORGANISM: Artificial Sequence
<220> FEATURE:
<223> OTHER INFORMATION: des B30 human insulin B-chain

<400> SEQUENCE: 3

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys
            20                  25
```

GLUCOSE SENSITIVE INSULINS AND USES THEREOF

CROSS-REFERENCE TO RELATED APPLICATIONS

This application is a 35 U.S.C. § 371 National Stage application of International Application PCT/EP2019/074987 (WO 2020/058322), filed Sep. 18, 2019, which claims priority to European Patent Applications 18195490.0, filed Sep. 19, 2018 and 19176911.6, filed May 28, 2019; the contents of which are incorporated herein by reference.

BACKGROUND

Glucose is the most important component in human energy homeostasis, and uncontrolled blood glucose is the hallmark of diabetes. The major objective of diabetes treatment is to adjust blood glucose levels towards normal values, and insulin is the most effective drug for this purpose. Glucose adjustment using insulin is however a difficult balance between hyperglycaemia and hypoglycaemia. Even with modern blood glucose monitors, hypoglycaemia is commonly occurring, and various glucose-sensitive insulin delivery systems have been engineered in attempts to improve the situation, both in form of mechanical systems (pumps/sensors) or molecular delivery systems. It would therefore be advantageous to equip diabetes-related peptide and protein drugs with a glucose-regulated bioactivity, e.g. a weaker glucose-lowering activity of insulin at low blood glucose values.

Glucose-sensitive insulin bioactivity can be achieved by equipping insulin with a glucose-binding element plus a binding partner that binds the glucose-binding element in competition with blood glucose, and thus controls insulin folding in equilibria between active and inactive states (WO2016149222, WO2010107520). When the glucose binding element on the insulin derivative binds the binding partner on the same insulin, the insulin attains an inactive or weakly active conformation. As glucose levels increase, the binding partner on the insulin derivative is displaced from the glucose binder, and the conformation of insulin changes to an active state.

Such systems must incorporate a glucose binder in some form. This has led to attempts to de novo design of small molecule glucose binders. It is however a very difficult task to bind glucose with reasonable affinity and selectivity in water since the structural differences from other carbohydrates is very subtle.

SUMMARY

The present invention provides glucose sensitive insulin derivatives. The insulin derivatives of the present invention comprise a macrocycle M, a glucose mimetic and human insulin or an analogue thereof. The macrocycle M is of Formula M1:

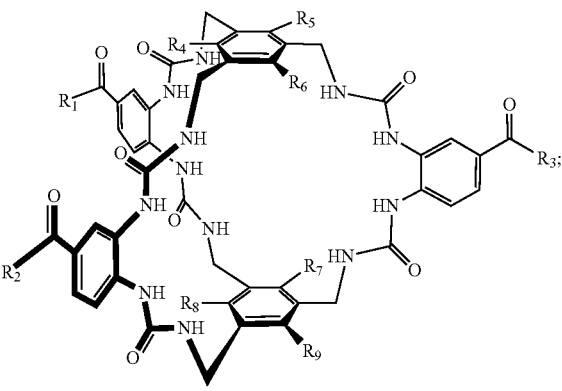

Formula M1 wherein $R_1$ and $R_2$ are independently selected from —OH,

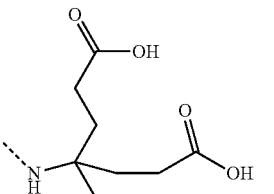

and

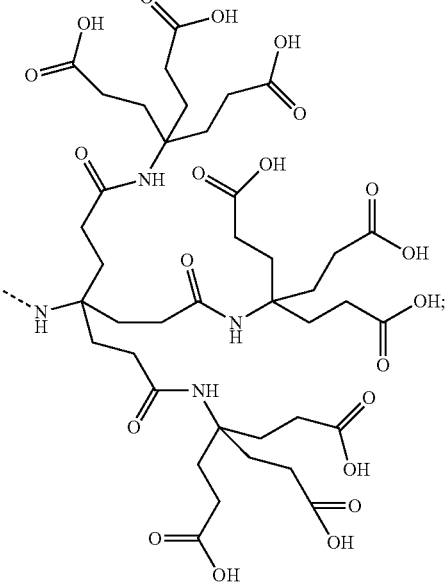

wherein $R_4$, $R_5$, $R_6$, $R_7$, $R_8$, and $R_9$ are independently selected from hydrogen, halogen, (1-4C)alkyl and (1-4C) alkoxy; and wherein $R_3$ denotes the attachment point of the macrocycle of Formula M1.

The macrocycles comprised in the insulin derivatives of the invention display an exceptionally high affinity towards glucose in aqueous media. Furthermore, the macrocycles comprised in the insulin derivatives of the invention display unprecedented levels of selectivity towards glucose over other structurally similar saccharides (e.g. mannose or fructose).

Without being bound by theory, it is believed that when the macrocycle M on the insulin derivative binds the glucose mimetic on the same insulin, the insulin attains an inactive or weakly active conformation. As glucose levels increase, the glucose mimetic on the insulin derivative is displaced from the macrocycle M, and the conformation of insulin changes to an active state. FIG. 1 illustrates the principle in schematic form (the positions of substitution on insulin in FIG. 1 should not be taken literally).

In one aspect, the invention relates to the furnishing of insulin derivatives which, after administration, activate insulin as a function of the blood glucose concentration.

In one aspect, the invention relates to the furnishing of insulin derivatives having low or no activity/availability during situations of low blood glucose levels, for example at levels below about 3 mM glucose.

In one aspect, the invention relates to the furnishing of insulin derivatives having high activity/availability in response to high blood glucose levels, for example, above about 10 mM glucose.

BRIEF DESCRIPTION OF DRAWINGS

FIG. 3: Open circles: Measured Intensity at 380 nm versus D-glucose concentration. Dashed line: Isotherm fitted to experimental data (1:1 binding model). Calculated Ka=14751.48±637.3 M−1.

DESCRIPTION

Figure 1:
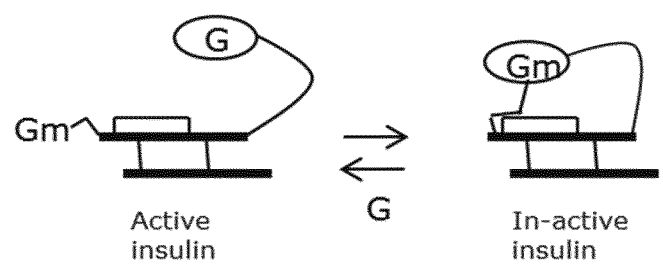
FIG. 1 is a schematic illustration of glucose sensitive insulin derivatives (Gm=glucose mimetic, G=glucose). Glucose-sensitive insulin bioactivity can be achieved by equipping insulin with a glucose-binding element plus a binding partner (a glucose mimetic, such as a glucoside) that binds the glucose-binding element in competition with blood glucose, and thus controls insulin folding in equilibria between active and inactive states.

The present invention relates to glucose sensitive compounds which activates the insulin receptor in a glucose dependent fashion.

In one aspect of the present invention, the invention relates to a glucose sensitive insulin derivative comprising human insulin or a human insulin analogue, a glucose mimetic and a glucose binder.

In one aspect of the present invention, the glucose binder is a macrocycle M. In one aspect of the present invention, the macrocycle M is of Formula M1:

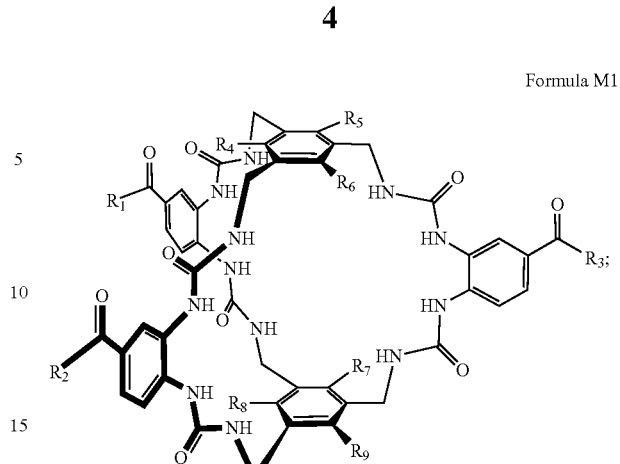

Formula M1 wherein $R_1$ and $R_2$ are independently selected from —OH,

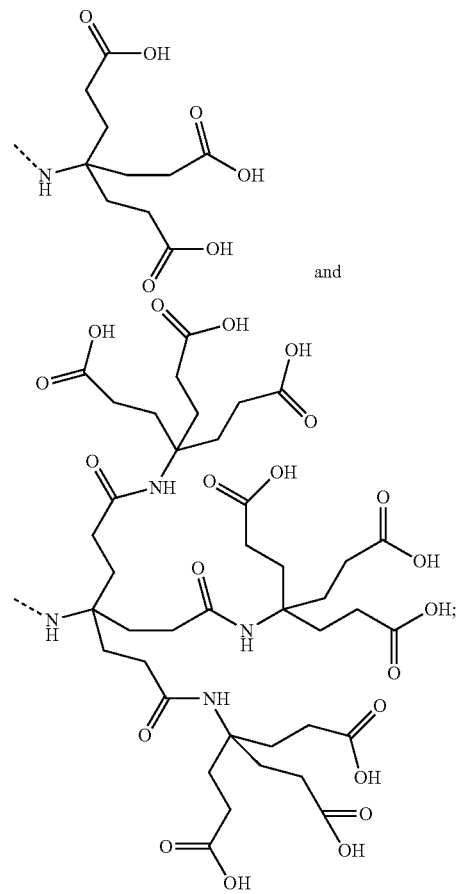

wherein $R_4$, $R_5$, $R_6$, $R_7$, $R_8$, and $R_9$ are independently selected from hydrogen, halogen, (1-4C)alkyl and (1-4C) alkoxy; and wherein $R_3$ denotes the attachment point of the macrocycle of Formula M1.

In another aspect, the invention relates to a glucose sensitive insulin derivative comprising human insulin or a human insulin analogue, two glucose mimetics and two glucose binders.

General Definitions

The term "compound" is used herein to refer to a molecular entity, and "compounds" may thus have different structural elements besides the minimum element defined for each compound or group of compounds. It follows that a compound may be a polypeptide or a derivative thereof, as long as the compound comprises the defined structural and/or functional elements. The term "compound" is also meant to cover pharmaceutically relevant forms hereof, i.e. the invention relates to a compound as defined herein or a pharmaceutically acceptable salt, amide, or ester thereof.

The term "peptide" or "polypeptide", as e.g. used in the context of the invention, refers to a compound which comprises a series of amino acids interconnected by amide (or peptide) bonds. In a particular embodiment the peptide consists of amino acids interconnected by peptide bonds.

The term "analogue" generally refers to a peptide, the sequence of which has one or more amino acid changes when compared to a reference amino acid sequence. Analogues "comprising" certain specified changes may comprise further changes, when compared to their reference sequence. In particular embodiments, an analogue "has" or "comprises" specified changes. In other particular embodiments, an analogue "consists of" the changes. When the term "consists" or "consisting" is used in relation to an analogue e.g. an analogue consists or consisting of a group of specified amino acid mutations, it should be understood that the specified amino acid mutations are the only amino acid mutations in the analogue. In contrast an analogue "comprising" a group of specified amino acid mutations may have additional mutations. An "analogue" may also include amino acid elongations in the N-terminal and/or C-terminal positions and/or truncations in the N-terminal and/or C-terminal positions.

In general, amino acid residues may be identified by their full name, their one-letter code, and/or their three-letter code. These three ways are fully equivalent.

The term "derivative" generally refers to a compound which may be prepared from a native peptide or an analogue thereof by chemical modification, in particular by covalent attachment of one or more substituents.

The term "amino acid" includes proteinogenic (or natural) amino acids (amongst these the 20 standard amino acids), as well as non-proteinogenic (or non-natural) amino acids. Proteinogenic amino acids are those which are naturally incorporated into proteins. The standard amino acids are those encoded by the genetic code. Non-proteinogenic amino acids are either not found in proteins, or not produced by standard cellular machinery (e.g., they may have been subject to post-translational modification).

In what follows, each amino acid of the peptides of the invention for which the optical isomer is not stated is to be understood to mean the L-isomer (unless otherwise specified). Amino acids are molecules containing an amino group and a carboxylic acid group, and, optionally, one or more additional groups, often referred to as a side chain.

In what follows, each carbohydrate for which the optical isomer is not stated is to be understood to mean the D-isomer (unless otherwise specified).

The term "(1-4C)alkyl" as used herein covers a straight or branched alkyl group containing 1-4 carbon atoms.

The term "(1-4C)alkoxy" as used herein covers a straight or branched alkoxy group containing 1-4 carbon atoms.

The solid and dashed lines used in the chemical formulae hereinabove will be readily understood to have been used for illustration purposes only (i.e. to display the relative orientation of the compounds of the present invention). They do not refer to the absolute configuration (i.e. stereochemistry) of the compounds shown.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the invention may have geometric isomeric centres (E- and Z-isomers). It is to be understood that the present invention encompasses all optical, diastereoisomers and geometric isomers and mixtures thereof that are capable of saccharide recognition.

It is also to be understood that certain macrocyclic compounds of the invention may exist in solvated as well as unsolvated forms such as, for example, hydrated forms. It is to be understood that the invention encompasses all such solvated forms that are capable of saccharide recognition. It is also to be understood that certain compounds may exhibit polymorphism, and that the invention encompasses all such forms that are capable of saccharide recognition.

The macrocyclic compounds of the invention may exist in a number of different tautomeric forms and references to compounds of specific formulas include all such forms. For the avoidance of doubt, where a compound can exist in one of several tautomeric forms, and only one is specifically described or shown, all others are nevertheless embraced by a given formula. Examples of tautomeric forms include keto-, enol-, and enolate-forms, as in, for example, the following tautomeric pairs: keto/enol, imine/enamine, amide/imino alcohol, amidine/amidine, nitroso/oxime, thioketone/enethiol, and nitro/aci-nitro.

Compounds containing an amine function may also form N-oxides. A reference herein to a compound of a given formula that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example Advanced Organic Chemistry, by Jerry March, 4th Edition, Wiley Interscience, pages. More particularly, N-oxides can be made by the procedure of L. W. Deady (Syn. Comm. 1977, 7, 509-514) in which the amine compound is reacted with m-chloroperoxybenzoic acid (mCPBA), for example, in an inert solvent such as dichloromethane.

Insulin

The term "human insulin" as used herein means the human insulin hormone whose structure and properties are well-known. Human insulin has two polypeptide chains, named the A-chain and the B-chain. The A-chain is a 21 amino acid peptide and the B-chain is a 30 amino acid peptide, the two chains being connected by disulphide bridges: a first bridge between the cysteine in position 7 of the A-chain and the cysteine in position 7 of the B-chain, and a second bridge between the cysteine in position 20 of the A-chain and the cysteine in position 19 of the B-chain. A third bridge is present between the cysteines in position 6 and 11 of the A-chain.

The human insulin A-chain has the following sequence: GIVEQCCTSICSLYQLENYCN (SEQ ID NO:1), while the B-chain has the following sequence:

```
                                        (SEQ ID NO: 2)
         FVNQHLCGSHLVEALYLVCGERGFFYTPKT.
```

In the human body, the hormone is synthesized as a single-chain precursor proinsulin (preproinsulin) consisting of a prepeptide of 24 amino acids followed by proinsulin containing 86 amino acids in the configuration: prepeptide-B-Arg Arg-C-Lys Arg-A, in which C is a connecting peptide of 31 amino acids. Arg-Arg and Lys-Arg are cleavage sites for cleavage of the connecting peptide from the A and B chains.

"An insulin" according to the invention is herein to be understood as human insulin or an insulin from another species such as porcine or bovine insulin.

The term "insulin peptide", "insulin compound" or "insulin" as used herein means a peptide which is either human insulin or an analogue or a derivative thereof with insulin activity.

Insulin Analogue

The term "insulin analogue" as used herein means a modified human insulin wherein one or more amino acid residues of the insulin have been substituted by other amino acid residues and/or wherein one or more amino acid residues have been deleted from the insulin and/or wherein one or more amino acid residues have been added and/or inserted to the insulin.

The term "modification" as used herein, means substitutions, deletions, and additions (including insertions). The term "mutation" as used herein, means substitution or deletion of amino acids within the sequence of human insulin. The term mutation does not include additions, elongations or extensions to the sequence of human insulin. Mutations in the insulin molecule are denoted stating the chain (A or B), the position, and the one or three letter code for the amino acid residue substituting the native amino acid residue.

In one embodiment an insulin analogue comprises less than 10 amino acid mutations relative to human insulin, alternatively less than 9, 8, 7, 6, 5, 4, 3, 2 or 1 mutation(s) relative to human insulin. Any mutation to the insulin analogue as used herein means a mutation to the insulin peptide alone and does not include any linking group attached to the insulin peptide/analogue.

By "desB30" or "B(1-29)" is meant a natural insulin B chain or an analogue thereof lacking the B30 amino acid and "A(1-21)" means the natural insulin A chain. Thus, e.g., desB30 human insulin is an analogue of human insulin where the amino acid in position 30 in the B chain is deleted.

Herein terms like "A1", "A2" and "A3" etc. indicates the amino acid in position 1, 2 and 3 etc., respectively, in the A chain of insulin (counted from the N-terminal end). Similarly, terms like B1, B2 and B3 etc. indicates the amino acid in position 1, 2 and 3 etc., respectively, in the B chain of insulin (counted from the N-terminal end). Using the one letter codes for amino acids, terms like A21A, A21G and A21Q designates that the amino acid in the A21 position is A, G and Q, respectively. Using the three letter codes for amino acids, the corresponding expressions are A21Ala, A21Gly and A21Gln, respectively.

Herein, the term "amino acid residue" is an amino acid from which, formally, a hydroxy group has been removed from a carboxy group and/or from which, formally, a hydrogen atom has been removed from an amino group.

A human insulin analogue comprising desB30 was used in the examples of insulin derivatives. However, other tolerated mutations, combinations, number of mutations, sequence extensions/truncations etc. of the insulin analogue could likewise have been used to illustrate the invention. Examples of such insulin analogues are B28D human insulin, B28K B29P human insulin, and B3K B29E human insulin.

In one aspect, the insulin analogues of the present invention include: desB30 human insulin (A-chain of SEQ ID NO:1 and B-chain of SEQ ID NO:3).

In one aspect, the insulin analogue of the present invention is desB30 human insulin (A-chain of SEQ ID NO:1 and B-chain of SEQ ID NO:3).

Insulin Derivatives

The term 'insulin derivative', or 'derivative of an insulin analogue' as used herein refers to human insulin or an analogue thereof ('insulin analogue') to which a glucose mimetic and a macrocycle are attached. In other words, an insulin derivative of the present invention comprises human insulin or an analogue thereof, a macrocycle and a glucose mimetic.

In one aspect, an insulin derivative of the present invention comprises human insulin or an analogue thereof and at least one macrocycle and at least one glucose mimetic.

In another aspect, an insulin derivative of the invention comprises at least two macrocycles and at least two glucose mimetics.

In another aspect, an insulin derivative of the invention comprises two macrocycles and two glucose mimetics.

In one aspect, the macrocycle and the glucose mimetic, respectively, may each be attached via a linker to the human insulin or human insulin analogue. In one aspect, the points of attachment to human insulin or the human insulin analogue are selected from a) the alpha amino group of the amino acid residue in position 1 of the A-chain of human insulin or the human insulin analogue;

b) the alpha amino group in position 1 of the B-chain of human insulin or the human insulin analogue; and c) the epsilon amino group or the alpha carboxylic acid group of the lysine in position 29 of the B-chain of the human insulin or human insulin analogue.

In one aspect, the macrocycle and the glucose mimetic are not attached to the same attachment point on human insulin or the human insulin analogue.

Macrocycle

The macrocycle comprised in the insulin derivatives of the invention display high affinity towards glucose. The macrocycles comprised in the insulin derivatives of the invention display selectivity towards glucose over other structurally similar saccharides (e.g. mannose).

The macrocycle comprised in the insulin derivatives of the invention is macrocycle M of Formula M1:

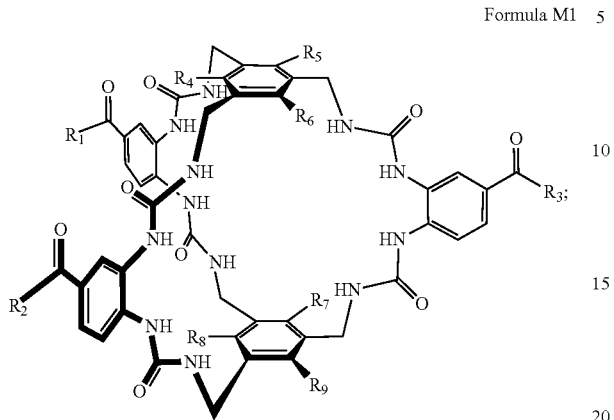

Formula M1 wherein $R_1$ and $R_2$ are independently selected from —OH,

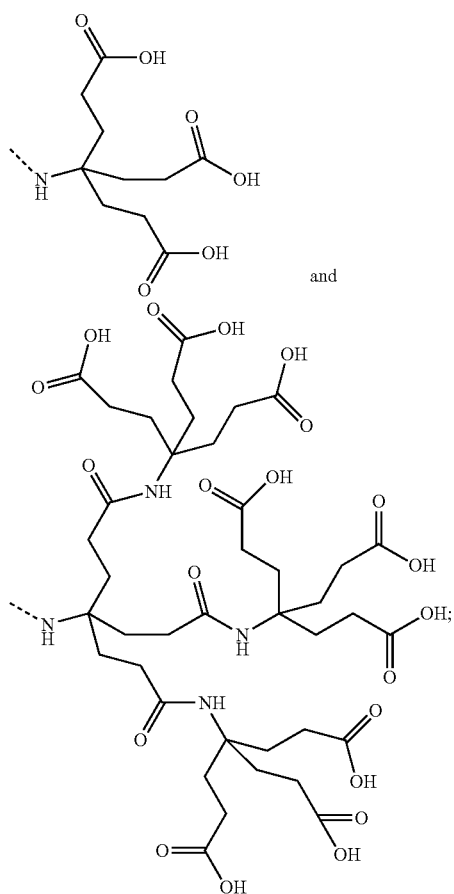

and wherein $R_4$, $R_5$, $R_6$, $R_7$, $R_8$, and $R_9$ are independently selected from hydrogen, halogen, (1-4C)alkyl and (1-4C)alkoxy; and wherein $R_3$ denotes the attachment point of the macrocycle of Formula M1.

In one aspect, $R_1$ and $R_2$ are identical. In one aspect, $R_1$ and $R_2$ are —OH. In another aspect, $R_1$ and $R_2$ are

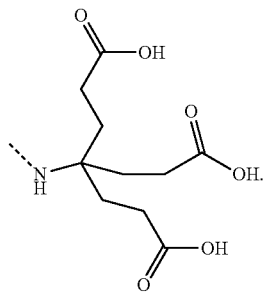

In a further aspect, $R_1$ and $R_2$ are

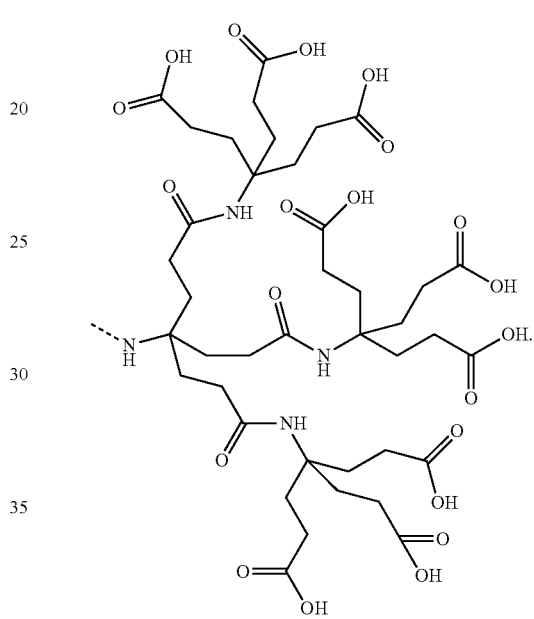

In one aspect, $R_4$, $R_5$, $R_6$, $R_7$, $R_8$, and $R_9$ are identical. In a further aspect, $R_4$, $R_5$, $R_6$, $R_7$, $R_8$, and $R_9$ are ethyl.

Glucose Mimetic

The term 'glucose mimetic' as used herein refers to a compound that is structurally similar to glucose, and binds to the macrocycle M. In other words, the glucose mimetic has affinity for the macrocycle M.

In one aspect, the glucose mimetic comprised in the insulin derivatives of the present invention is a glucoside. In a further aspect, the glucose mimetic comprised in the insulin derivatives of the present invention is 1-substituted beta-D-glucopyranoside.

Linker

The insulin derivatives according to the present invention may further comprise a linker between the macrocycle M and the human insulin analogue and/or a linker between the human insulin analogue and the glucose mimetic.

In the context of this invention a linker is a chemical moiety or residue used to covalently link the macrocycle and glucose mimetic, respectively, to human insulin or a human insulin analogue. The term "-linker-" is thus intended to mean the chemical unit of the insulin derivative, which is covalently linked to an amino acid residue of human insulin or a human insulin analogue and to the macrocycle or glucose mimetic, respectively.

Depending on the point of attachment, the reactivity of the linker ends may vary. The linker may have various forms, depending on the product in question.

The linker used to covalently link the macrocycle to human insulin or a human insulin analogue may be different from the linker used to covalently link the glucose mimetic to human insulin or a human insulin analogue.

In one embodiment, the linker comprises —(CH$_2$CH$_2$O)$_p$—, wherein p is an integer from 1-5.

In one embodiment, the linker is —NH(CH$_2$CH$_2$O)$_3$—CH$_2$CH$_2$-triazole-PhCH$_2$. In one embodiment, the linker is —(CH$_2$CH$_2$O)$_2$—CH$_2$CH$_2$C(O)—.

Alternative linkers having different length and composition could have been employed to generate linkage between human insulin or the human insulin analogue and the macrocycle and glucose mimetic, respectively.

In one aspect, the macrocycle M is attached to the alpha amino group in position 1 of the B-chain of the human insulin or human insulin analogue via a linker of Formula L1:

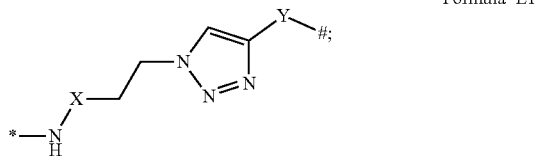

Formula L1 wherein X is CH$_2$— or (CH$_2$CH$_2$O—)$_p$, wherein p is an integer from 2 to 4;

wherein Y is CH$_2$—, (CH$_2$CH$_2$CO—), or -Ph-para-CH$_2$—;

wherein * denotes the attachment point to the macrocycle M; and wherein # denotes the attachment point to human insulin or the human insulin analogue, and wherein the glucose mimetic is attached via a linker to the epsilon amino group of the lysine (K) in position 29 of the B-chain of the human insulin or human insulin analogue, wherein said linker is of Formula L2:

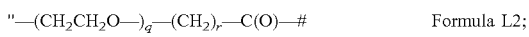

Formula L2;

wherein q is 1 or 2;

wherein r is 1 or 2;

wherein " denotes the attachment point to the glucose mimetic; and wherein # denotes the attachment point to human insulin or the human insulin analogue.

In a second aspect, the insulin derivative comprises two glucose mimetics and two macrocycles M of Formula M1, wherein the two macrocycles are attached to the alpha amino group in position 1 of the B-chain of human insulin or the human insulin analogue, and wherein the two glucose mimetics are attached to the alpha carboxylic acid group and/or the epsilon amino group of the lysine (K) in position 29 of the B-chain of the human insulin or human insulin analogue. The two glucose mimetics may be attached via a trivalent linker to the alpha carboxylic acid group or the epsilon amino group of the lysine (K) in position 29 of the B-chain of the human insulin or human insulin analogue, or each of the two glucose mimetics may be attached via a bivalent linker attached to the alpha carboxylic acid group and the epsilon amino group of the lysine (K), respectively, in position 29 of the B-chain of the human insulin or human insulin analogue.

In one aspect, the trivalent linker linking the two macrocycles M to the alpha amino group in position 1 of the B-chain of human insulin or the human insulin analogue is of Formula L3:

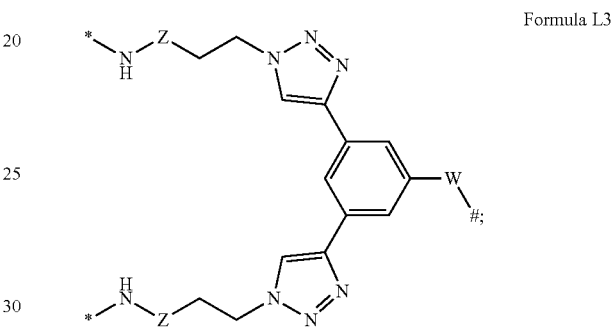

Formula L3 wherein Z is CH$_2$— or (CH$_2$CH$_2$O—)$_3$;

wherein W is CH$_2$—, (CH$_2$CH$_2$CO—), or -Ph-para-CH$_2$—;

wherein * denotes the attachment points to the macrocycle M; and wherein # denotes the attachment point to human insulin or the human insulin analogue.

In one aspect, the trivalent linker linking the two glucose mimetics to the alpha carboxylic acid group of the lysine (K) in position 29 of the B-chain of the human insulin or human insulin analogue is of Formula L4:

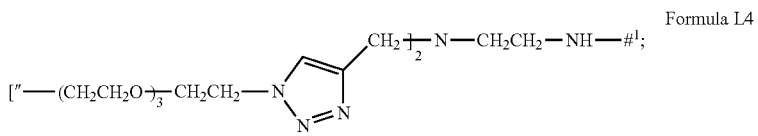

Formula L4 wherein " denotes the attachment points to the glucose mimetic; and wherein #$^1$ denotes the attachment point to the alpha carboxyl acid group of the lysine (K) in position 29 of the B-chain of the human insulin or human insulin analogue.

In one aspect, the trivalent linker linking the two glucose mimetics to the epsilon amino group of the lysine (K) in position 29 of the B-chain of the human insulin or human insulin analogue is of Formula L5:

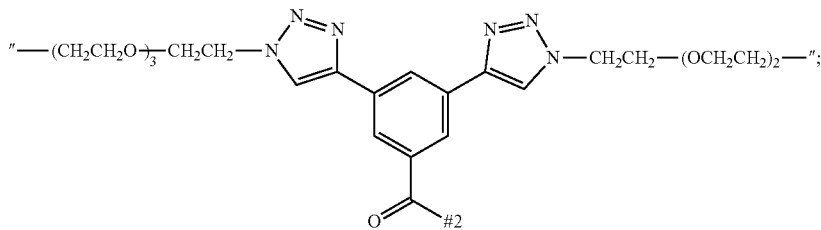

Formula L5 wherein " denotes the attachment points to the glucose mimetic; and wherein #² denotes the attachment point to the epsilon amino group of the lysine (K) in position 29 of the B-chain of the human insulin or human insulin analogue.

In one aspect, the two bivalent linkers linking the two glucose mimetics to the alpha carboxylic acid group and the epsilon amino group of the lysine (K), respectively, in position 29 of the B-chain of the human insulin or human insulin analogue are of Formula L6 and L7, respectively:

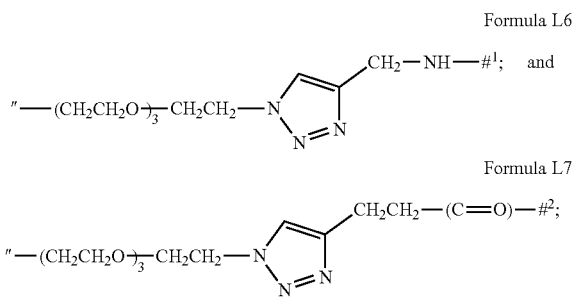

Formula L6

Formula L7 wherein " denotes the attachment point to the glucose mimetic; and wherein #¹ denotes the attachment point to the alpha carboxyl acid group of the lysine (K) in position 29 of the B-chain of the human insulin or human insulin analogue; and wherein #² denotes the attachment point to the epsilon amino group of the lysine (K) in position 29 of the B-chain of the human insulin or human insulin analogue.

Production of Human Insulin and Insulin Analogues

The production of polypeptides, e.g., insulins, is well known in the art. The insulin or insulin analogue may for instance be produced by classical peptide synthesis, e.g., solid phase peptide synthesis using t-Boc or Fmoc chemistry or other well-established techniques, see, e.g., Greene and Wuts, "Protective Groups in Organic Synthesis", John Wiley & Sons, 1999. The insulin or insulin analogue may also be produced by a method which comprises culturing a host cell containing a DNA sequence encoding the analogue and capable of expressing the insulin analogue in a suitable nutrient medium under conditions permitting the expression of the insulin analogue. Several recombinant methods may be used in the production of human insulin and human insulin analogues. Examples of methods which may be used in the production of insulin in microorganisms such as, e.g., *Escherichia coli* and *Saccharomyces cerevisiae* are, e.g., disclosed in WO2008034881.

Typically, the insulin or insulin analogue is produced by expressing a DNA sequence encoding the insulin analogue in question or a precursor thereof in a suitable host cell by well-known technique as disclosed in e.g. EP1246845 or WO2008034881.

The insulin or insulin analogue is recovered from the cell culture medium and may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., Protein Purification, J.-C. Janson and Lars Ryden, editors, VCH Publishers, New York, 1989). Preferably, the insulin or insulin analogue is purified by affinity chromatography on an anti-insulin analogue antibody column. Additional purification may be achieved by conventional chemical purification means, such as high performance liquid chromatography. Other methods of purification, including barium citrate precipitation, are known in the art, and may be applied to the purification of the insulin or insulin analogue described herein (see, for example, Scopes, R., Protein Purification, Springer-Verlag, N.Y., 1982).

Pharmaceutical Compositions

The invention also relates to pharmaceutical compositions comprising a compound of the invention, or a pharmaceutically acceptable salt, amide, or ester thereof, and one or more pharmaceutically acceptable excipient (s). Such compositions may be prepared as is known in the art.

The term "excipient" broadly refers to any component other than the active therapeutic ingredient(s). The excipient may be an inert substance, an inactive substance, and/or a not medicinally active substance. The excipient may serve various purposes, e.g. as a carrier, vehicle, diluent, tablet aid, and/or to improve administration, and/or absorption of the active substance. Non-limiting examples of excipients are: solvents, diluents, buffers, preservatives, tonicity regulating agents, chelating agents, and stabilisers. The formulation of pharmaceutically active ingredients with various excipients is known in the art, see e.g. Remington: The Science and Practice of Pharmacy (e.g. 21st edition (2005), and any later editions).

A composition of the invention may be in the form of a liquid formulation, i.e. aqueous formulation comprising water. A liquid formulation may be a solution, or a suspension. Alternatively, it may be a solid formulation, e.g. a freeze-dried or spray-dried composition.

A pharmaceutical composition of the invention may further comprise a second active ingredient, such as a therapeutic agent, which may simplify administration in case of combination treatments.

Pharmaceutical Indications

Diabetes

The term "diabetes" or "diabetes mellitus" includes type 1 diabetes, type 2 diabetes, gestational diabetes (during pregnancy) and other states that cause hyperglycaemia. The term is used for a metabolic disorder in which the pancreas produces insufficient amounts of insulin, or in which the cells of the body fail to respond appropriately to insulin thus preventing cells from absorbing glucose. As a result, glucose builds up in the blood.

Type 1 diabetes, also called insulin-dependent diabetes mellitus (IDDM) and juvenile-onset diabetes, is caused by B-cell destruction, usually leading to absolute insulin deficiency.

Type 2 diabetes, also known as non-insulin-dependent diabetes mellitus (NIDDM) and adult-onset diabetes, is associated with predominant insulin resistance and thus relative insulin deficiency and/or a predominantly insulin secretory defect with insulin resistance.

Other Indications

In one embodiment, a compound according to the invention is used for the preparation of a medicament for the treatment or prevention of hyperglycemia including stress induced hyperglycemia, type 2 diabetes, impaired glucose tolerance, or type 1 diabetes.

In another embodiment, a compound according to the invention is used as a medicament for delaying or preventing disease progression in type 2 diabetes.

In one embodiment of the invention, the compound is for use as a medicament for the treatment or prevention of hyperglycemia including stress induced hyperglycemia, type 2 diabetes, impaired glucose tolerance, or type 1 diabetes.

In a further embodiment the invention is related to a method for the treatment or prevention of hyperglycemia including stress induced hyperglycemia, type 2 diabetes, impaired glucose tolerance, or type 1 diabetes, the method comprising administering to a patient in need of such treatment an effective amount for such treatment of a compound according to the invention.

Mode of Administration

The term "treatment" is meant to include both the prevention and minimization of the referenced disease, disorder, or condition (i.e., "treatment" refers to both prophylactic and therapeutic administration of a compound of the present invention or composition comprising a compound of the present invention unless otherwise indicated or clearly contradicted by context.

The route of administration may be any route which effectively transports a compound of this invention to the desired or appropriate place in the body, such as parenterally, for example, subcutaneously, intramuscularly or intravenously. Alternatively, a compound of this invention can be administered orally, pulmonary, rectally, transdermally, buccally, sublingually, or nasally.

For parenteral administration, a compound of this invention is formulated analogously with the formulation of known insulins. Furthermore, for parenteral administration, a compound of this invention is administered analogously with the administration of known insulins and the physicians are familiar with this procedure.

The amount of a compound of this invention to be administered, the determination of how frequently to administer a compound of this invention, and the election of which compound or compounds of this invention to administer, optionally together with another antidiabetic compound, is decided in consultation with a practitioner who is familiar with the treatment of diabetes.

Embodiments

The invention is further described by the following non-limiting embodiments:

1. An insulin derivative comprising human insulin or a human insulin analogue, a glucose mimetic and a macrocycle M of Formula M1:

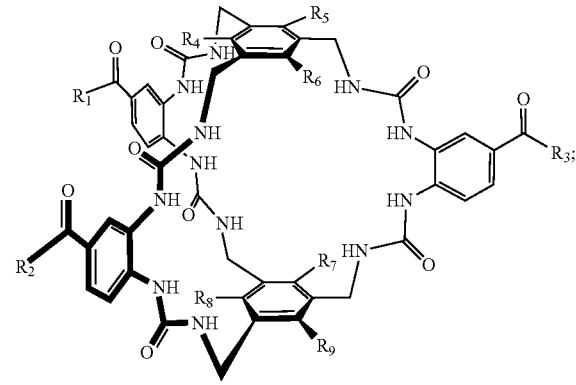

Formula M1 wherein $R_1$ and $R_2$ are independently selected from —OH,

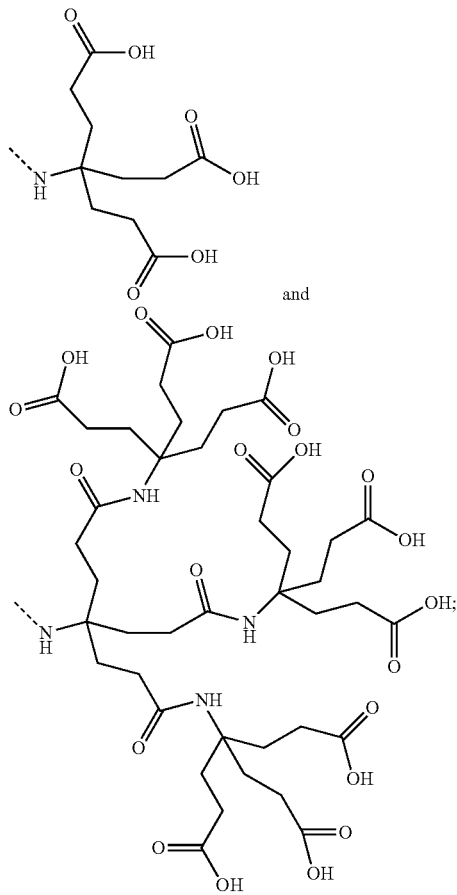

and wherein $R_4$, $R_5$, $R_6$, $R_7$, $R_8$, and $R_9$ are independently selected from hydrogen, halogen, (1-4C)alkyl and (1-4C)alkoxy; and wherein $R_3$ denotes the attachment point of the macrocycle of Formula M1.

2. The insulin derivative according to embodiment 1, wherein the insulin derivative comprises two glucose mimetics and two macrocycles M of Formula M1.

3. The insulin derivative according to anyone of embodiments 1-2, wherein $R_1$ and $R_2$ are

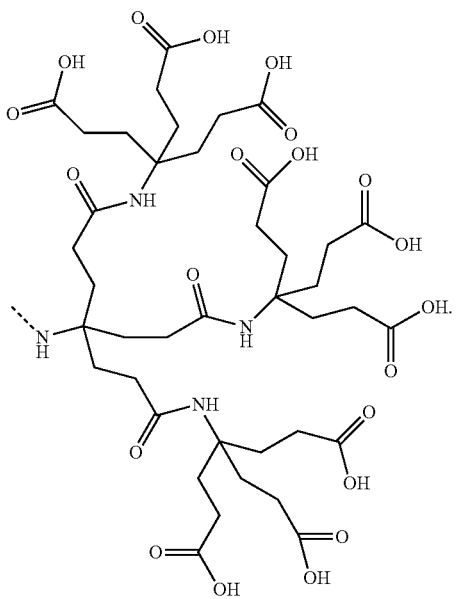

4. The insulin derivative according to any one of embodiments 1-3, wherein each of $R_4$, $R_5$, $R_6$, $R_7$, $R_8$, and $R_9$ are ethyl.

5. The insulin derivative according to any one of embodiments 1-4, wherein the macrocycle and the glucose mimetic, respectively, each is attached via an optional linker to the human insulin or human insulin analogue, wherein the points of attachment to human insulin or the human insulin analogue are selected from:

a) the alpha amino group of the amino acid residue in position 1 of the A-chain of human insulin or the human insulin analogue;

b) the alpha amino group in position 1 of the B-chain of human insulin or the human insulin analogue; and c) the epsilon amino group of the lysine (K) in position 29 of the B-chain of the human insulin or human insulin analogue;

provided that the macrocycle and the glucose mimetic are not attached to the same attachment point on human insulin or the human insulin analogue.

6. The insulin derivative according to any one of embodiments 1-5, wherein the macrocycle M is attached via a linker to the human insulin or human insulin analogue, wherein said linker is \*—NH(CH$_2$CH$_2$O)$_m$—CH$_2$CH$_2$-triazole-PhCH$_2$-#, wherein m is an integer from 1-5;

\* is the attachment point to the macrocycle M; and # is the attachment point to human insulin or the human insulin analogue.

7. The insulin derivative according to any one of embodiments 1-6, wherein the glucose mimetic is attached via a linker to the human insulin or human insulin analogue, wherein said linker is "—(CH$_2$CH$_2$O)$_n$—CH$_2$CH$_2$C(O)—#, wherein n is an integer from 0-5;

" is the attachment point to the glucose mimetic; and # is the attachment point to human insulin or the human insulin analogue.

8. The insulin derivative according to any one of embodiments 1-7, wherein the human insulin or a human insulin analogue is the human insulin analogue desB30 human insulin.

9. The insulin derivative according to any one of embodiments 1-8, wherein the glucose mimetic is beta-D-glucopyranoside.

10. The insulin derivative according to any one of embodiments 1-9, wherein the insulin derivative is selected from B1-macrocycle B29-glycoside desB30 human insulin 8 of Example 1;

B1-macrocycle A1-glycoside desB30 human insulin 12 of Example 2;

B29-macrocycle A1-glycoside desB30 human insulin 13 of Example 3; and

B1-bis-macrocycle B29-bis-glycoside desB30 human insulin 14 of Example 4.

11. A pharmaceutical composition for the treatment of diabetes in a patient in need of such treatment, comprising a therapeutically effective amount of an insulin derivative according to any one of embodiments 1-10, together with a pharmaceutically acceptable excipient.

12. The pharmaceutical composition of embodiment 11, for use as a medicament.

13. The pharmaceutical composition of embodiment 11, for use in the treatment of patients with diabetes.

The invention is even further described by the following non-limiting embodiments:

14. An insulin derivative comprising human insulin or a human insulin analogue, a glucose mimetic and a macrocycle M of Formula M1:

Formula M1

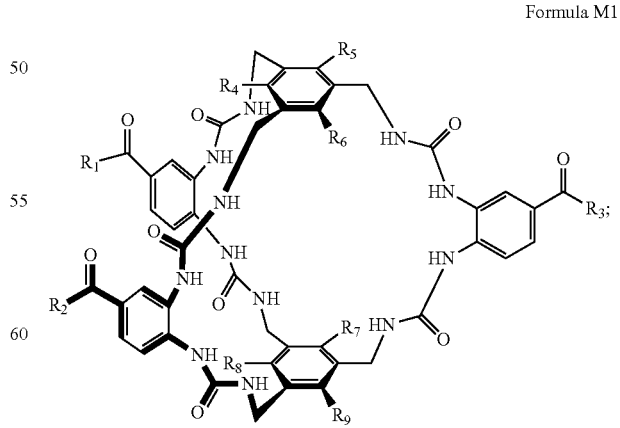

wherein $R_1$ and $R_2$ are independently selected from —OH,

19

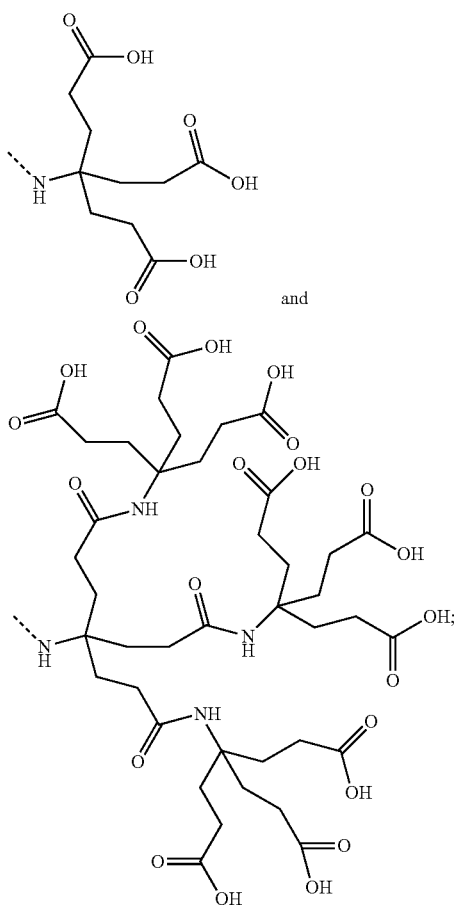

wherein R₄, R₅, R₆, R₇, R₈, and R₉ are independently selected from hydrogen, halogen, (1-4C)alkyl and (1-4C)alkoxy; and wherein R₃ denotes the attachment point of the macrocycle of Formula M1.

15. The insulin derivative according to embodiment 14, wherein the glucose mimetic is a glucoside.

16. The insulin derivative according to embodiment 15, wherein the glucose mimetic is beta-D-glucopyranoside.

17. The insulin derivative according to anyone of embodiments 14 to 16, wherein $R_1$ and $R_2$ are —OH.

18. The insulin derivative according to anyone of embodiments 14 to 16, wherein $R_1$ and $R_2$ are

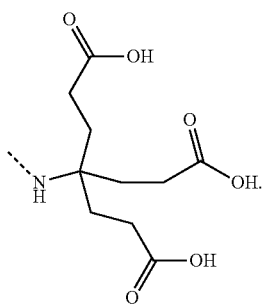

19. The insulin derivative according to anyone of embodiments 14 to 16, wherein $R_1$ and $R_2$ are

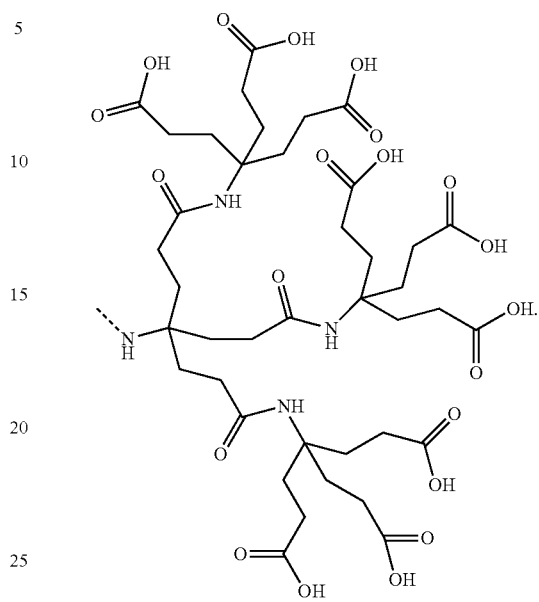

20. The insulin derivative according to any one of embodiments 14 to 19, wherein each of R₄, R₅, R₆, R₇, R₈, and R₉ are ethyl.

21. The insulin derivative according to any one of embodiments 14 to 20, wherein the macrocycle and the glucose mimetic, respectively, each is attached via an optional linker to the human insulin or human insulin analogue, wherein the points of attachment to human insulin or the human insulin analogue are selected from:

a) the alpha amino group of the amino acid residue in position 1 of the A-chain of human insulin or the human insulin analogue;

b) the alpha amino group in position 1 of the B-chain of human insulin or the human insulin analogue; and c) the epsilon amino group or the alpha carboxylic acid group of the lysine (K) in position 29 of the B-chain of the human insulin or human insulin analogue;

provided that the macrocycle and the glucose mimetic are not attached to the same attachment point on human insulin or the human insulin analogue.

22. The insulin derivative according to embodiment 21, wherein the macrocycle is attached to the alpha amino group in position 1 of the B-chain of human insulin or the human insulin analogue; and wherein the glucose mimetic is attached to the epsilon amino group of the lysine (K) in position 29 of the B-chain of the human insulin or human insulin analogue.

23. The insulin derivative according to embodiment 22, wherein the macrocycle M is attached via a linker to the human insulin or human insulin analogue, wherein said linker is of Formula L1

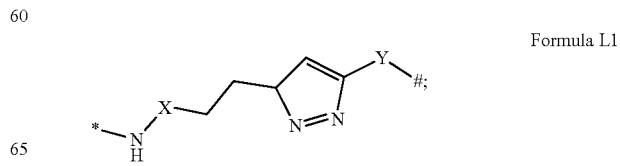

Formula L1 wherein X is CH₂— or (CH₂CH₂O—)$_p$, wherein p is an integer from 2 to 4;

wherein Y is CH₂—, (CH₂CH₂CO—), or -Ph-para-CH₂—;

wherein * denotes the attachment point to the macrocycle M; and wherein # denotes the attachment point to human insulin or the human insulin analogue.

24. The insulin derivative according to embodiment 23, wherein the glucose mimetic is attached via a linker to the human insulin or human insulin analogue, wherein said linker is of Formula L2:

"—(CH₂CH₂O—)$_q$—(CH₂)$_r$—C(O)—#;

wherein q is 1 or 2;
wherein r is 1 or 2;
wherein " denotes the attachment point to the glucose mimetic; and
wherein # denotes the attachment point to human insulin or the human insulin analogue.

25. The insulin derivative according to any one of embodiments 14 to 24, wherein the human insulin or a human insulin analogue is the human insulin analogue desB30 human insulin.

26. The insulin derivative according embodiment 25, wherein the insulin derivative is selected from the group of INS1 of Example 1

INS1

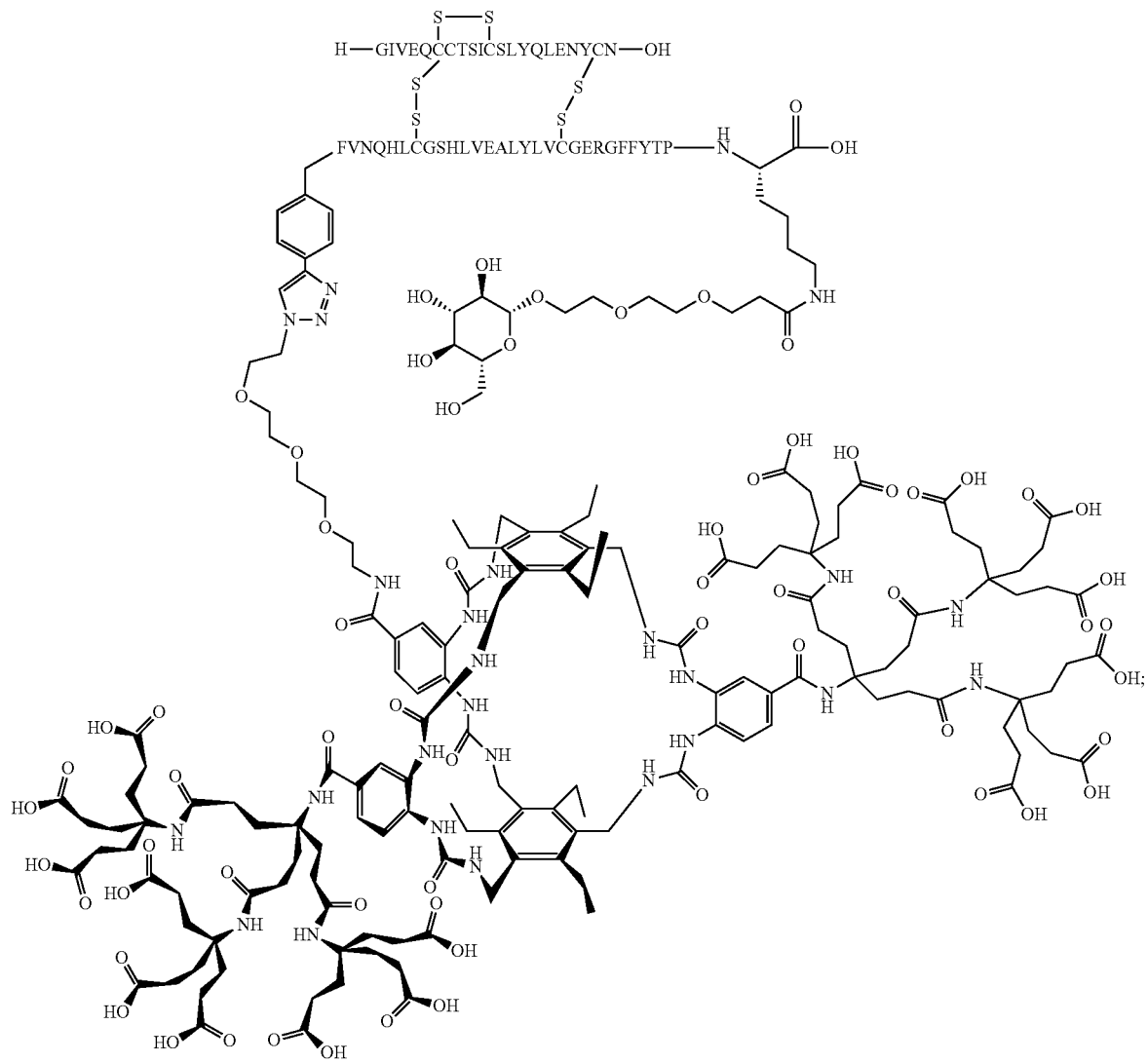

INS9 of Example 5;
INS18 of Example 8;
INS21 of Example 9;
INS28 of Example 12;
INS30 of Example 14;
INS34 of Example 18;
INS35 of Example 19;
INS36 of Example 20;
INS37 of Example 21; and
INS38 of Example 22.

27. The insulin derivative according to any one of embodiments 14 to 22, wherein the insulin derivative comprises two glucose mimetics and two macrocycles M of Formula M1.

28. The insulin derivative according to embodiment 27, wherein the two macrocycles are attached to the alpha amino group in position 1 of the B-chain of human insulin or the human insulin analogue.

29. The insulin derivative according to embodiment 28, wherein the two macrocycles M are attached via a trivalent linker to the alpha amino group in position 1 of the B-chain of human insulin or the human insulin analogue, wherein said linker is of Formula L3

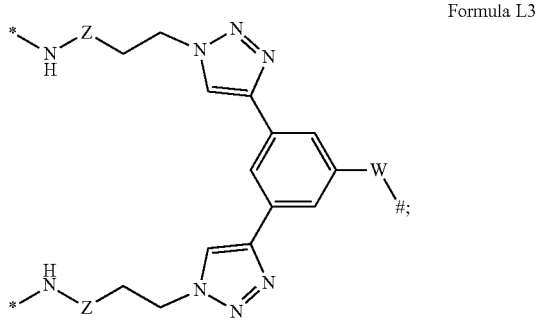

Formula L3 wherein Z is $CH_2$— or $(CH_2CH_2O—)_3$;
wherein W is $CH_2$—, $(CH_2CH_2CO—)$, or -Ph-para-$CH_2$—;
wherein * denotes the attachment point to the macrocycle M; and
wherein # denotes the attachment point to human insulin or the human insulin analogue.

30. The insulin derivative according to embodiment 29, wherein the two glucose mimetics are attached to the alpha carboxylic acid group and/or the epsilon amino group of the lysine (K) in position 29 of the B-chain of the human insulin or human insulin analogue.

31. The insulin derivative according to embodiment 30, wherein the two glucose mimetics are attached via a trivalent linker attached to the alpha carboxylic acid group or the epsilon amino group of the lysine (K) in position 29 of the B-chain of the human insulin or human insulin analogue; wherein said linker is selected from the group of wherein said linkers are of Formula L6 and Formula L7:

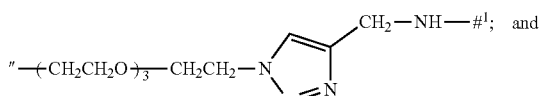

Formula L6

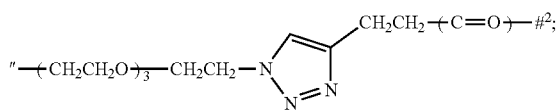

Formula L7 wherein " denotes the attachment point to the glucose mimetic; and
wherein $\#^1$ denotes the attachment point to the alpha carboxyl acid group of the lysine (K) in position 29 of the B-chain of the human insulin or human insulin analogue; and wherein $\#^2$ denotes the attachment point to the epsilon amino group of the lysine (K) in position 29 of the B-chain of the human insulin or human insulin analogue.

32. The insulin derivative according to any one of embodiments 27 to 31, wherein the human insulin or a human insulin analogue is the human insulin analogue desB30 human insulin.

33. The insulin derivative according to embodiment 32, wherein the insulin derivative is selected from the group of
INS22 of Example 10;
INS29 of Example 13;
INS32 of Example 16; and
INS33 of Example 17.

34. The insulin derivative according to embodiment 14, wherein the insulin derivative is INS41 of Example 25.

35. The insulin derivative according to embodiment 14, wherein the insulin derivative is INS5 of Example 3.

36. The insulin derivative according to embodiment 1, wherein the insulin derivative is INS4 of Example 2.

37. An insulin derivative according to any one of embodiments 14 to 36, wherein the insulin derivative has the ability to bind to the insulin receptor.

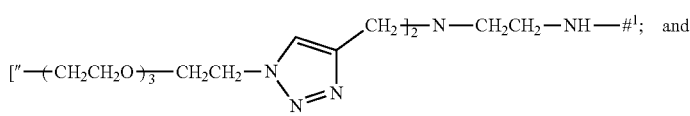

Formula L4

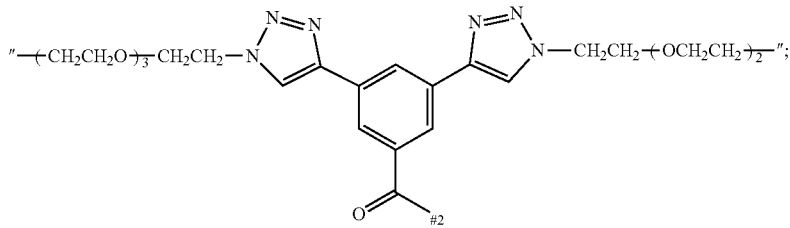

Formula L5 or wherein the two glucose mimetics are each attached via a bivalent linker attached to the alpha carboxylic acid group and the epsilon amino group of the lysine (K), respectively, in position 29 of the B-chain of the human insulin or human insulin analogue;

38. An insulin derivative according to any one of embodiments 14 to 36, wherein the insulin derivative has higher insulin receptor affinity in presence of 20 mM glucose than when no glucose is present.

39. An insulin derivative according to any one of embodiments 14 to 36, wherein the insulin derivative has at least 2-fold higher insulin receptor affinity in presence of 20 mM glucose than when no glucose is present.

40. A pharmaceutical composition for the treatment and/or prevention of diabetes in a patient in need of such treatment, comprising a therapeutically effective amount of an insulin derivative according to any one of embodiments 14 to 36, together with a pharmaceutically acceptable excipient.

41. The pharmaceutical composition of embodiment 40, for use as a medicament.

42. The pharmaceutical composition of embodiment 40, for use in the treatment and/or prevention of diabetes.

43. An insulin derivative according to any one of embodiments 14 to 36 for use as a medicament.

44. An insulin derivative according to any one of embodiments 14 to 36 for use in the treatment and/or prevention of diabetes, diabetes of Type 1, diabetes of Type 2, impaired glucose tolerance, hyperglycemia, and metabolic syndrome (metabolic syndrome X, insulin resistance syndrome).

45. An insulin derivative according to any one of embodiments 14 to 36 for use in a method for treatment and/or prevention of diabetes, diabetes of Type 1, diabetes of Type 2, impaired glucose tolerance, hyperglycemia, and metabolic syndrome (metabolic syndrome X, insulin resistance syndrome).

46. A method for treatment and/or prevention of diabetes, diabetes of Type 1, diabetes of Type 2, impaired glucose tolerance, hyperglycemia, and metabolic syndrome (metabolic syndrome X, insulin resistance syndrome) comprising administration of an effective amount of the insulin derivative according to any one of embodiments 14 to 36 to a patient in need thereof.

EXAMPLES

The chemical structure is shown for all final products and also intermediate products unless the chemical name is unambiguous. The final products and some intermediates are in addition to their structure listed with chemical names in the following sections; these chemical names are however not complete chemical names unambiguously defining the products and are only provided to ease reading. The nomenclature used for numbering PEG linkers vary in literature; herein PEG3 denotes a PEG linker having three ethylene groups; PEG4 denotes a PEG linker having four ethylene groups, etc.

Materials and Methods
List of Abbreviations
CV Column volume
DBU 1,8-Diazabicyclo(5.4.0)undec-7-en
DCM Dichloromethane
DIC N,N-diisopropylcarbodiimide
DMF N,N-dimethylformamide
DMSO dimethylsulfoxide
EtOAc Ethyl acetate
DIPEA N,N-diisopropylethylamine
Fmoc-OSu 9-Fluorenylmethyl N-succinimidyl carbonate
HBTU 2-(1H-benzotriazol-1-yl)-1,1,3,3-tetramethyluronium hexafluorophosphate
HOBt 1-Hydroxybenzotriazole
HONSu M-hydroxysuccinimide
HRMS High resolution mass spectrometry
LCMS Liquid chromatography mass spectrometry
MeCN Acetonitrile
NMR Nuclear magnetic resonance
NMP N-methyl-pyrrolidone
RP-HPLC Reverse-phase high performance chromatography
TEMPO (2,2,6,6-tetramethylpiperidin-1-yl)oxyl
THF Tetrahydrofuran
THPTA tris(3-hydroxypropyltriazolylmethyl)amine Preparation of Building Blocks
Preparation of Compound 1

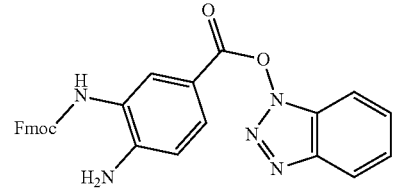

3,4-Diaminobenzoic acid (41.0 g, 0.269 mol) was mixed with saturated $NaHCO_3$ (0.40 L) and acetonitrile (0.40 L) to give a brown slurry. Next, solid Fmoc-OSu (99.99 g, 0.296 mol) was added in portions over 5 minutes. The heterogenous suspension was allowed to stir at room temperature for 16 hours and then acidified with 1M HCl (aq). The solids were collected on a frit and washed with cold diethyl ether (3×100 mL), hexane (3×100 mL), then MeOH (3×50 mL) and then dried under vacuum. Brown solid (101 g, 0.269 mol, 100%). This intermediate (10.0 g, 0.027 mol), HOBt (8.181 g, 0.053 mol), and HBTU (20.259 g, 0.053 mol) were dissolved in THF (300) mL) and DIPEA (18.610 mL, 0.107 mol). The heterogenous slurry was stirred at room temperature for 90 minutes after which the solvent was removed in vacuo to afford a viscous oil. The oil was dissolved in EtOAc (80 ml) and was added to a rapidly stirring mixture of water (200 ml) and EtOAc (40 mL). After ca. 2 mins a precipitate formed and diethyl ether (100 mL) was added to the flask. After stirring for 10 minutes, solid 1 were collected by filtration and washed with water (3×10 mL) and diethyl ether (2×10 mL) before drying under vacuum for 16 hours.

$^1$H NMR: (500 MHz, DMSO-d6) δ 8.94 (s, 1H), 8.14 (dd, J=17.7, 8.4 Hz, 2H), 8.01-7.93 (m, 1H), 7.90 (d, J=7.6 Hz, 2H), 7.87-7.68 (m, 6H), 7.68-7.61 (m, 1H), 7.54 (dt, J=11.5, 7.5 Hz, 1H), 7.42 (t, J=7.4 Hz, 2H), 7.34 (t, J=7.6 Hz, 2H), 6.89 (d, J=8.6 Hz, 1H), 6.46 (s, 2H), 4.44 (s, 2H), 4.31 (s, 1H), 3.40 (s, 7H), 3.03 (s, 7H), 2.50 (s, 4H).

Preparation of Compound 2a

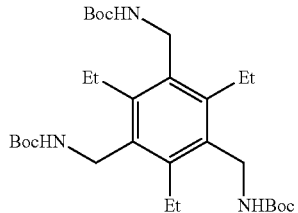 [SMILES: CCc1c(CNC(=O)OC(C)(C)C)c(CC)c(CNC(=O)OC(C)(C)C)c(CC)c1CNC(=O)OC(C)(C)C]

NaH (3.809 g, 0.095 mol, 60% in mineral oil) was added to a Schlenk flask (100 mL) and placed under nitrogen. The mineral oil was removed by washing the solids with 3×25 mL petroleum ether 60-80° C. The washed NaH was suspended in anhydrous DMF (40 mL) and vigorously stirred for ca. 10 mins whilst cooling in an ice bath. Solid trifluoroacetamide (16.147 g, 0.143 mol) was added portion-wise under a nitrogen counter-flow. After five minutes of stirring the mixture was let warm to room temperature. Once the 3evolution of gas had completely stopped (within 1 hour), solid 1,3,5-tribromomethyl-2,4,6-triethylbenzene (7.00 g, 0.016 mol, Sigma-Aldrich) was added portion-wise under a nitrogen counter-flow and the resulting white suspension was stirred at room temperature. After 18 hours, the suspension was poured into 0.5 M HCl (150 mL) and the light orange precipitate collected on a frit. The solids were washed with water (2×10 mL) and then dried under vacuum overnight (ca. $10^{-2}$ mbar). Off-white solid (7.910 g, 0.015 mol, 93%). The intermediate acetamide (4.90 g, 0.009 mol) was dissolved in methanol (38.6 mL) and water (38.6 mL). NaOH (1.05 g, 3.150 mol) was added and the reaction mixture was left to stir for ca. 18 hours at 65° C. Solid Boc$_2$O (7.287 g, 0.033 mol) and triethylamine (2.534 mL, 0.026 mol) were added and the reaction was left to stir for a further 4 hours at ambient temperature. The reaction mixture was diluted with DCM (200 mL) and washed with sat. aq. NaHCO$_3$ (200 mL), 1 M NaOH (200 mL) and brine (100 mL). The organic phase was concentrated to dryness and the resultant crude product purified by MPLC (Biotage with 0 to 50% MeOH in DCM). Colourless solid 2a (4.820 g, 0.009 mol, 96%).

$^1$H NMR (450 MHz, CDCl$_3$) δ m.br 4.33 (9H, ArC$\underline{H}_2$NHCO$_2$C(CH$_3$)$_3$), N$\underline{H}$), q. 2.71 (6H, $^3J_{HH}$=7.5 Hz, ArC$\underline{H}_2$CH$_3$), s. 1.44 (27H, CO$_2$C(C$\underline{H}_3$)$_3$), t. 1.19 (9H, $^3J_{HH}$=7.5 Hz, ArCH$_2$C$\underline{H}_3$).

$^{13}$C NMR (125 MHz, CDCl$_3$) δ 155.5 ($\underline{C}$O$_2$C(CH$_3$)$_3$), 143.9, 132.6 (Ar), 79.7 (CO$_2$$\underline{C}$(CH$_3$)$_3$), 38.9 Ar$\underline{C}$H$_2$NHCO$_2$C(CH$_3$)$_3$, 28.6 (CO$_2$C($\underline{C}$H$_3$)$_3$), 23.0 (Ar$\underline{C}$H$_2$CH$_3$), 16.7 (ArCH$_2$$\underline{C}$H$_3$).

Preparation of Compound 2b

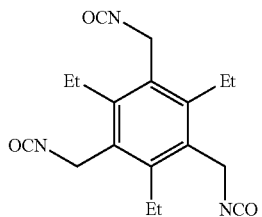

A pre-dried 200 mL Schlenk flask was charged with a magnetic stirrer and compound 2a (1.266 g, 2.25 mmol) and then placed under a nitrogen atmosphere. 2-chloropyridine (1.7 mL, 20.21 mmol) and anhydrous DCM (70 mL) were added via syringe to give a colourless, homogenous solution. Triflic anhydride (1.5 mL, 10.11 mmol) was added dropwise at ambient temperature over 2 mins with stirring (400 rpm). The reaction was stirred for 30 mins before a small aliquot of the reaction mixture (ca 50 mL) was withdrawn and analysed by TLC (SiO$_2$, 50% Et$_2$O in petrol), which revealed complete consumption of the starting material (Rf=0.24) and conversion to 2b (Rf=0.5). The solvent was removed on a rotary evaporator to give an off-white solid. The solids were extracted with Et$_2$O (×2 15 mL) and passed through an alumina plug (20 mm×20 mm), eluting with a further 20 mL of Et$_2$O. The colourless filtrate was evaporated to dryness and the residue recrystallized from hexane. Colourless crystalline solid 2b (0.435 g, 1.33 mmol, 59%).

$^1$H NMR (400 MHz, Toluene-d$_6$) δ s. 3.93 (6H, ArC$\underline{H}_2$NCO), m. 2.51-2.37 (6H, ArC$\underline{H}_2$CH$_3$), m. 0.96-0.86 (9H, ArCH$_2$C$\underline{H}_3$).

$^{13}$C NMR (100 MHz, Toluene-d$_6$) 143.2, 132.6 (Ar), 124.0 (N$\underline{C}$O), 40.4 (Ar$\underline{C}$H$_2$NCO), 22.8 (Ar$\underline{C}$H$_2$CH$_3$), 16.0 (ArCH$_2$$\underline{C}$H$_3$).

Preparation of Compound 3

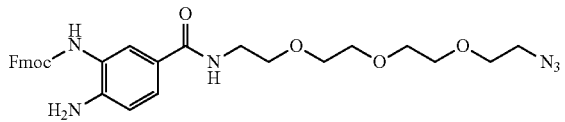

Compound 1 (3.308 g, 5.443 mmol) and anhydrous DIPEA (1.270 mL, 7.258 mmol) were dissolved in anhydrous THF (20 mL). 11-Azido-3,6,9-trioxanundecan-1-amine (1.000 mL, 4.536 mmol) was added dropwise. After 16 hours stirring at room temperature the reaction mixture was concentrated under vacuum to yield a brown residue. The crude product was purified by flash column chromatography eluting with 50 to 100% EtOAc/DCM. The product containing fractions were combined and evaporated to dryness to give a colourless amorphous solid 3 (2.50 g, 4.35 mmol, 80%).

$^1$H NMR: (400 MHz, CDCl$_3$) δ 7.74 (d, J=7.5 Hz, 2H, ArH), 7.60 (d, J=2.0 Hz, 2H, ArH), 7.45 (s, 1H, ArH), 7.38 (t, J=7.5 Hz, 2H, ArH), 7.26 (d, J=9.6 Hz, 2H, ArH), 7.05 (s, 1H, ArH), 6.84 (s, 1H ArH), 6.65 (d, J=8.4 Hz, 1H C(O)NHCH2), 4.49 (s, 1H, Flu-CH2), 4.18 (s, 2H, Flu-OCH2), 3.68-3.45 (m, 14H, OCH2), 3.27 (t, J=5.0 Hz, 2H C(O)NHCH2), 1.34 (d, J=6.7 Hz, 2H, N3CH$_2$).

Preparation of Compound 4

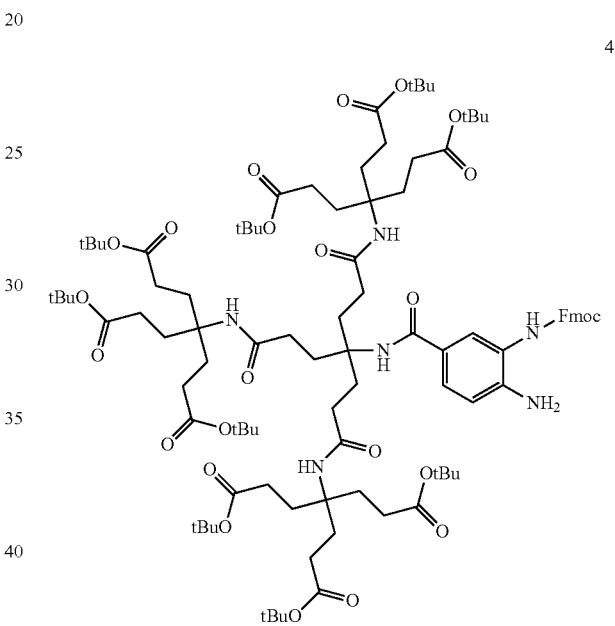

N,N',N"-tris[tris(2-tert-butoxycarbonyl-ethyl)methyl]-3,3',3"-(1-aminomethanetriyl)-tripropanamide (7.0 g, 5.0 mmol, Allichem (G2 amine)) and compound 1 (5.310 g, 10 mmol) were dissolved in anhydrous THF (210 mL). Triethylamine (2.23 mL, 16 mmol) was added and the reaction was left to stir for 18 hours at room temperature. The reaction mixture was diluted with Et$_2$O (40 mL) and the resulting suspension filtered. The resulting filtrate was concentrated under vacuum and the residue loaded onto 120 g C18 cartridge in MeCN (10 mL) and purified by reverse phase chromatography (70-100% acetone in water gradient). The product containing fractions were combined and evaporated to dryness to give off-white amorphous solid 4 (7.61, 4.0 mmol g, 81%).

$^1$H NMR: (400 MHz, (CDCl3): δ 1.43 (s, 81H, C(26)H3), 1.95 (m, 18H, C(23)H2), 2.11 (t, J=7.2 Hz, 6H, C(18)H2), 2.17 (m, 18H, C(22)H2), 2.25 (t, J=7.2 Hz, 6H, C(19)H2), 4.27 (m, 3H, C(7)H and NH2), 4.47 (d, J=7.4 Hz, 2H, C(8)H2), 6.08 (s, 3H, NH), 6.76 (d, J=8.4 Hz, 1H, C(13)H), 7.26-7.31 (m, 2H, C(4)H), 7.38 (t, J=7.4 Hz, 2H, C(3)H), 7.57-7.69 (m, 2H, C(5)H), 7.71 (d, J=8.7 Hz, 1H, C(2)H), 7.75 (d, J=7.6 Hz, 3H, C(2)H), 7.78 (d, J=2.1 Hz, 1H, C(15)H), 8.54 (s, 1H, NH)

$^{13}$C NMR: (100 MHz, (CDCl3): δ 28.0 (C26), 29.8 (C22), 29.9 (C23), 31.8 (C19), 32.2 (C18), 47.2 (C7), 53.4 (C17), 57.4 (C21), 67.3 (C8), 80.6 (C25) 116.6 (C12), 119.9 (C2), 122.6 (C10), 124.6 (C14), 125.3 (C4), 126.0 (C15), 126.8 (C13), 127.0 (C5), 127.6 (C3), 141.3 (C1), 143.8 (C6), 145.3 (C11), 154.9 (C9), 166.6 (C16), 172.7 (C24), 173.1 (C20);

IR: $\lambda_{max}$ (cm$^{-1}$) 2977, 2963, 1752, 1723, 1689, 1637, 1535, 1367, 1242, 1151, 1098, 844;

HRMS: (ESI+) Found [M+2Na]$^{2+}$: 921.0252.

Preparation of Compound 5a

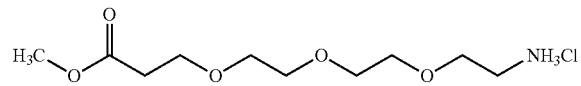

Into a flask were added 1-amino-3,6,9-trioxadodecan-12-oic acid (Fluorochem) (10.0 g, 37.7 mmol) and MeOH (50 mL). The mixture was cooled in an ice bath (0° C.). Thionyl chloride (7.25 mL, 99.4 mmol) was added dropwise. The mixture was heated to reflux (3 h), allowed to cool to ambient temperature, and diluted with EtOAc (100 mL, producing white precipitate). Solids were isolated by vacuum filtration and dried under vacuum to yield pure ester hydrochloride 1 b (8.09 g, 25.6 mmol, 68% yield, white solid 5a), which was used directly in the next step.

Preparation of Compound 5b

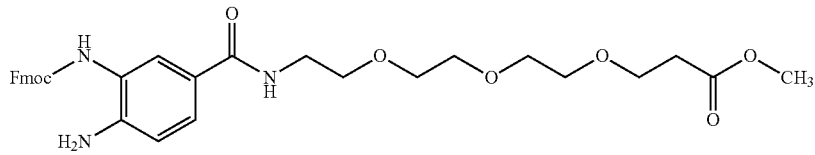

Compound 1 (1.100 g, 2.014 mmol) and anhydrous DIPEA (0.702 mL, 4.028 mmol) were dissolved in anhydrous THF (70 mL). Compound 5a (0.763 g, 2.417 mmol) dissolved in anhydrous THF (10 mL) was added dropwise. After 16 hours stirring at room temperature 150 mL saturated NH$_4$Cl$_{(aq)}$ was added. The resulting suspension was extracted with DCM (3×30 mL). The combined organic extracts were dried over MgSO$_4$ and evaporated to dryness. The resulting residue was recrystalised from minimal boiling EtOAc to give a waxy solid 5b (1.03 g, 1.62 mmol, 80%).

Preparation of Compound 6a

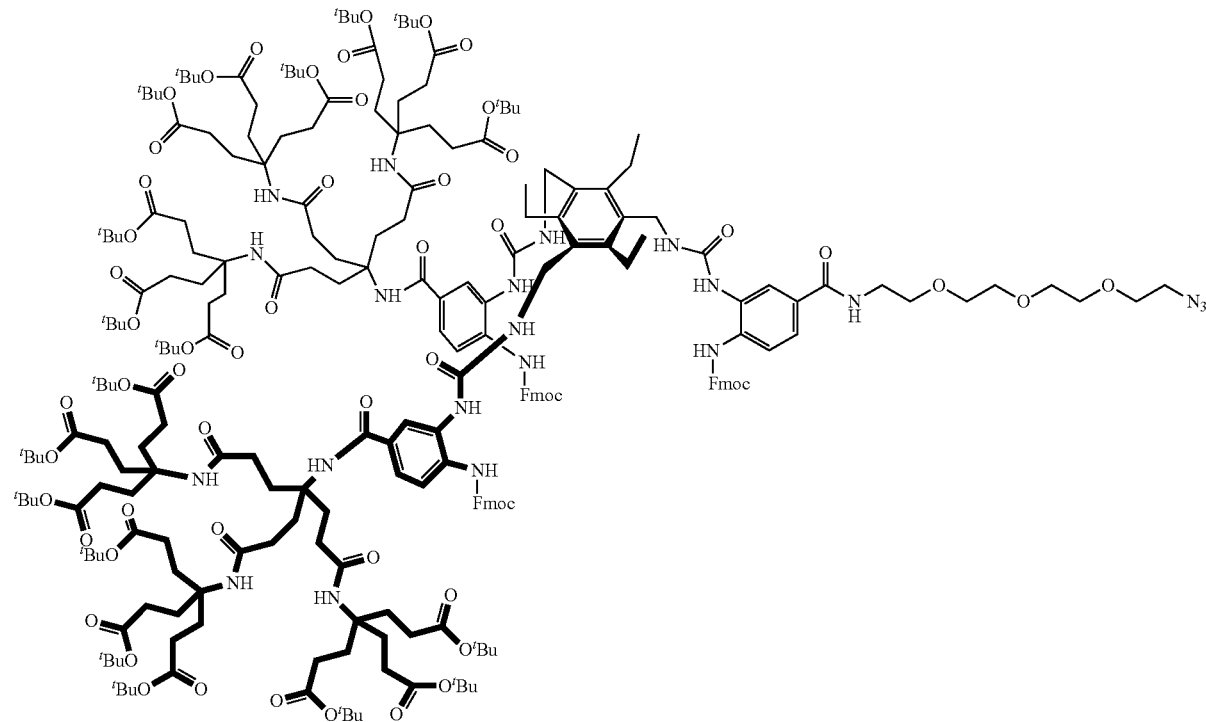

A Schlenk flask was charged with a stirrer bar, compound 4 (0.933 g, 0.519 mmol), compound 2b (0.100 g, 0.305 mmol), anhydrous THF (6 mL), and anhydrous pyridine (0.147 mL, 1.833 mmol). The mixture was then heated to 50° C. for 5 hours. Compound 3 (0.228 g, 0.397 mmol) dissolved in anhydrous THF (1 mL) was added in one portion and the reaction stirred for a further 12 hours. The reaction mixture was concentrated under vacuum and the crude residue loaded onto a 120 g C18 cartridge in 5 mL MeCN and purified by reverse phase flash chromatography (1CV 85% acetone/H2O, 10 CV 85-95% acetone/H2O, 2CV 95% acetone). The product containing fractions were combined and evaporated to dryness to give an off-white amorphous solid (458 mg, 46%).

$^1$H NMR: (400 MHz, (CD$_3$OD): δ 8.02-7.46 (19H, br. m, ArH), 7.46-7.11 (14H, br. m, ArH), 4.60-4.30 (12H, br. m, NHCH2Ph and FmocH), 4.19 (3H, br. s, NHCH2Ph and FmocH), 3.71-3.55 (14H, m, PEG CH$_2$), 3.33 (2H, m, PEG CH$_2$), 2.85 (6H, br. s, CH$_2$), 2.35-1.86 (96H, m, dendrimer CH$_2$), 1.42 (162H, s, CH$_3$), 1.23 (9H, br. s, CH$_3$);

HRMS: (ESI+) calculated for $C_{244}H_{352}N_{21}O_{57}Na_3^{2+}$: 1520.8407, found [M+3Na]$^{3+}$: 1520.8395.

Preparation of Compound 6b

Compound 6a (2.400 g, 0.534 mmol) was dissolved in anhydrous DCM (26 mL) and treated with DBU (0.479 mL, 3.204 mmol) at room temperature under nitrogen. After 1 hour, the reaction mixture was concentrated under vacuum to remove the DCM, re-dissolved in EtOAc (50 mL), washed with HCl (50 mL, 1 M) and the organic phase dried over MgSO$_4$, filtered and the resulting filtrate concentrated under vacuum. the crude residue loaded onto a 120 g SNAP Ultra C18 135 cartridge in 5 mL MeCN and purified by reverse phase flash chromatography (70 to 100% MeOH:water gradient. The product containing fractions were combined and evaporated to dryness to give light yellow amorphous solid 6b (1.56 g, 0.408 mmol, 76%).

$^1$H NMR (400 MHz, Methanol-d$_4$) δ 7.91 (s, 2H), 7.41 (s, 7H), 7.38 (d, J=8.2 Hz, 2H), 7.35 (d, J=8.2 Hz, 1H), 7.27 (d, J=2.0 Hz, 2H), 7.23 (d, J=2.0 Hz, 1H), 7.18 (dd, J=8.4, 2.0 Hz, 2H), 7.10 (dd, J=8.3, 2.1 Hz, 1H), 4.48 (s, 6H), 3.71-3.55 (m, 14H), 3.51 (t, J=5.3 Hz, 2H), 2.96-2.72 (m, 6H), 2.28-2.13 (m, 48H), 2.13-2.03 (m, 12H), 2.01-1.83 (m, 36H), 1.42 (s, 162H), 1.31-1.15 (m, 9H).

$^{13}$C NMR (101 MHz, Methanol-d$_4$) δ 175.5, 174.4, 170.2, 170.1, 158.0, 157.9, 145.1, 141.8, 141.4, 133.9, 132.8, 132.3, 129.9, 129.7, 124.9, 124.5, 118.9, 118.4, 117.3, 117.0, 81.6, 71.6, 71.5, 71.3, 71.1, 70.6, 59.3, 58.7, 51.7, 40.9, 39.3, 32.5, 32.2, 30.7, 30.4, 28.4, 23.9, 17.0.

HRMS [M+3H]$^{3+}$ calculated for $C_{199}H_{328}N_{21}O_{51}$ requires: 1276.1239, found: 1276.1305.

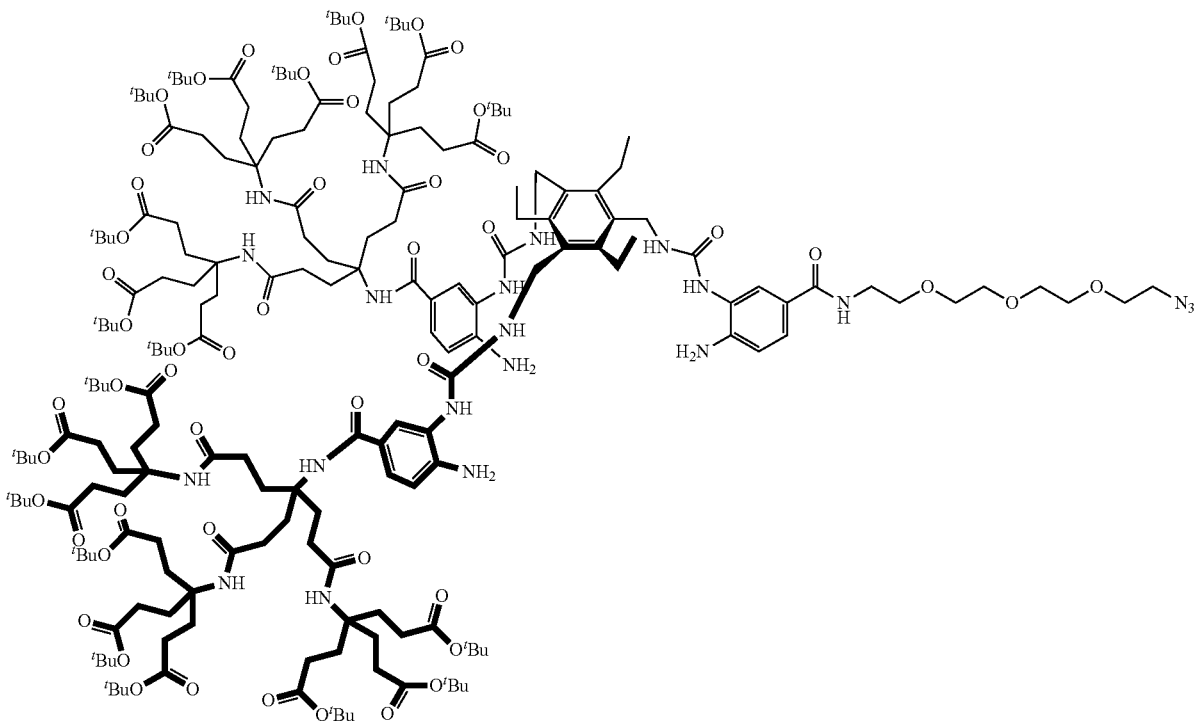

Preparation of Compound 6c

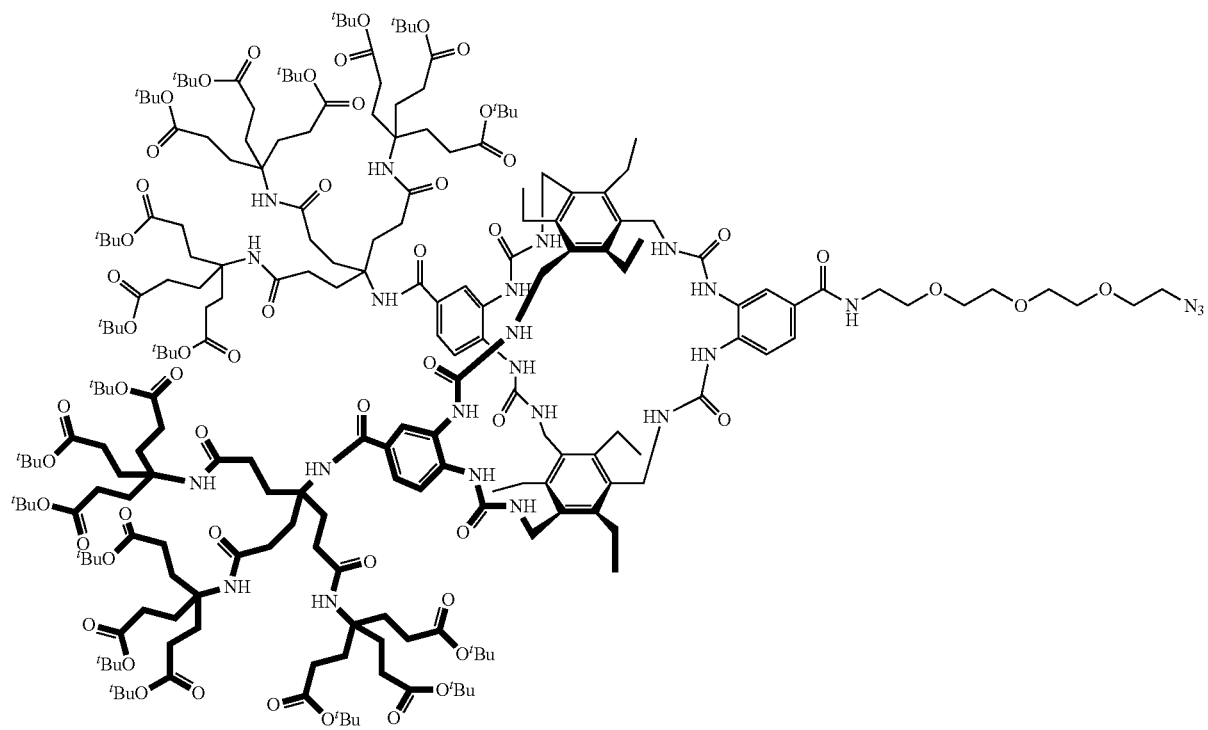

Compound 6b (1.057 g, 0.276 mmol) was dissolved in anhydrous pyridine and heated to 50° C. under nitrogen. In a separate pear-shaped flask compound 2b (0.108 g, 0.331 mmol) was dissolved in anhydrous DCM (11.500 mL) and added via syringe pump (1.2 mL/hr). After the addition was complete the reaction mixture was concentrated under vacuum to give an orange solid which was azeotroped with toluene (50 mL) to remove residual pyridine. The crude product was onto a 120 g C18 cartridge in 5 mL MeCN and purified by reverse phase flash chromatography (80 to 100% acetone:water gradient). The product containing fractions were combined and evaporated to dryness to give light orange amorphous solid 6c (0.70 g, 0.169 mmol, 61%).

$^1$H NMR (400 MHz, Methanol-$d_4$) δ 8.09-7.86 (m, 6H), 7.64 (dd, J=8.6, 2.1 Hz, 2H), 7.58 (dd, J=8.5, 2.1 Hz, 1H), 7.44 (s, 6H), 4.57-4.24 (m, 12H), 3.69-3.54 (m, 12H), 3.53-3.45 (m, 2H), 3.34-3.30 (m, 2H), 3.07-2.82 (m, 6H), 2.80-2.68 (m, 6H), 2.33-2.04 (m, 60H), 2.04-1.80 (m, 36H), 1.41 (s, 162H), 1.28-1.11 (m, 18H).

$^{13}$C NMR (101 MHz, Methanol-$d_4$) δ 174.3, 174.2, 173.1, 168.3, 168.0, 157.1, 156.0, 155.9, 143.2, 143.2, 143.1, 135.8, 135.4, 133.0, 133.0, 132.7, 132.5, 129.9, 129.2, 128.8, 128.1, 124.7, 124.6, 121.0, 120.9, 80.3, 70.3, 70.3, 70.2, 70.0, 69.8, 69.3, 58.1, 57.5, 57.4, 50.4, 39.6, 37.6, 37.4, 31.1, 30.9, 30.9, 29.4, 29.1, 27.1, 22.3, 15.5, 15.4, 15.3. HRMS [M+3H]$^{3+}$ calculated for $C_{217}H_{349}N_{24}O_{54}$ requires: 1385.1768, found: 1385.1824

Preparation of Compound 6d

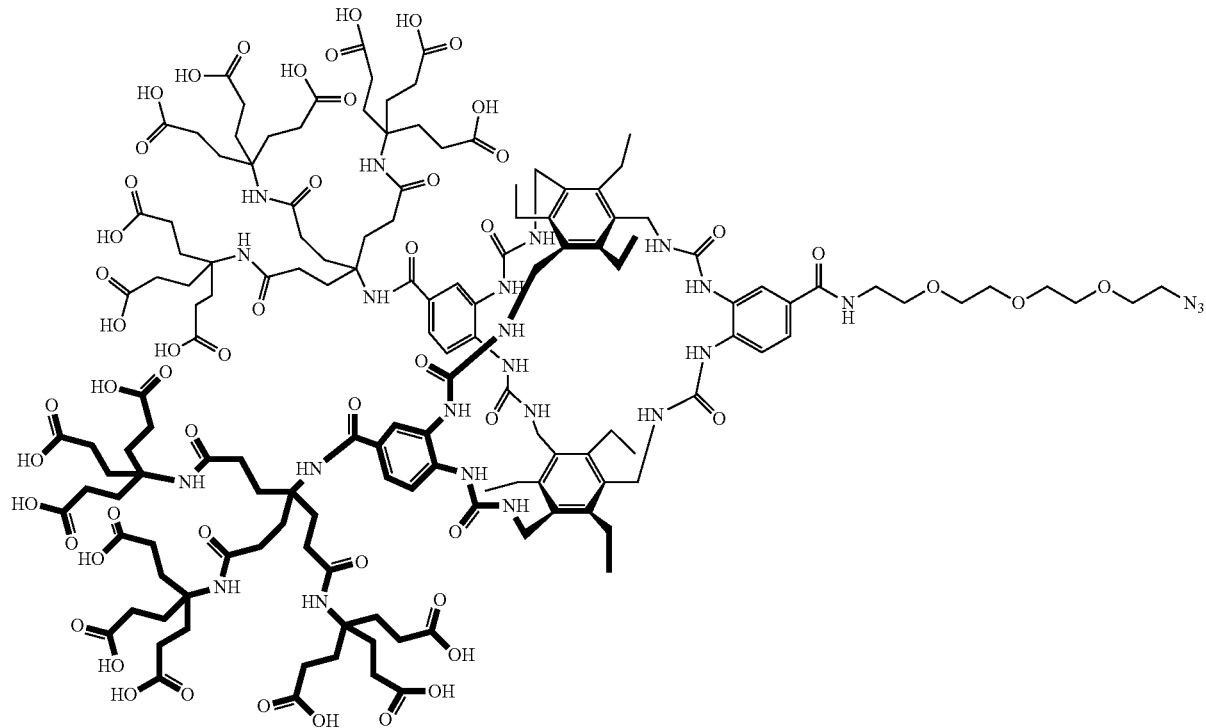

Compound 6c (334.0 mg, 0.080 mmol) was dissolved in DCM (8.00 mL) and TFA (5.50 mL, 72 mmol) and stirred for 16 hours at room temperature. The reaction mixture was poured into water (90 mL) and the DCM evaporated under vacuum. The resulting white solid was collected by centrifugation. The pellet was re-suspended in water (30 mL) and centrifuged. The supernatant was decanted and the resulting solid dried under high vacuum to give and off-white solid 6d. 250 mg, 0.0796 mmol, 99%.

$^1$H NMR (400 MHz, deuterated phosphate buffer in D20) δ 7.78-7.60 (m, 6H), 7.52-7.41 (m, 3H), 7.33 (s, 3H), 4.55-4.07 (m, 12H), 3.70-3.38 (m, 14H), 3.24 (t, J=4.9 Hz, 1H), 3.02-2.94 (m, 1H), 2.81-2.46 (m, 12H), 2.26-2.11 (m, 12H), 2.10-1.86 (m, 48H), 1.86-1.63 (m, 36H), 1.23-0.79 (m, 18H).

Preparation of Compound 7a

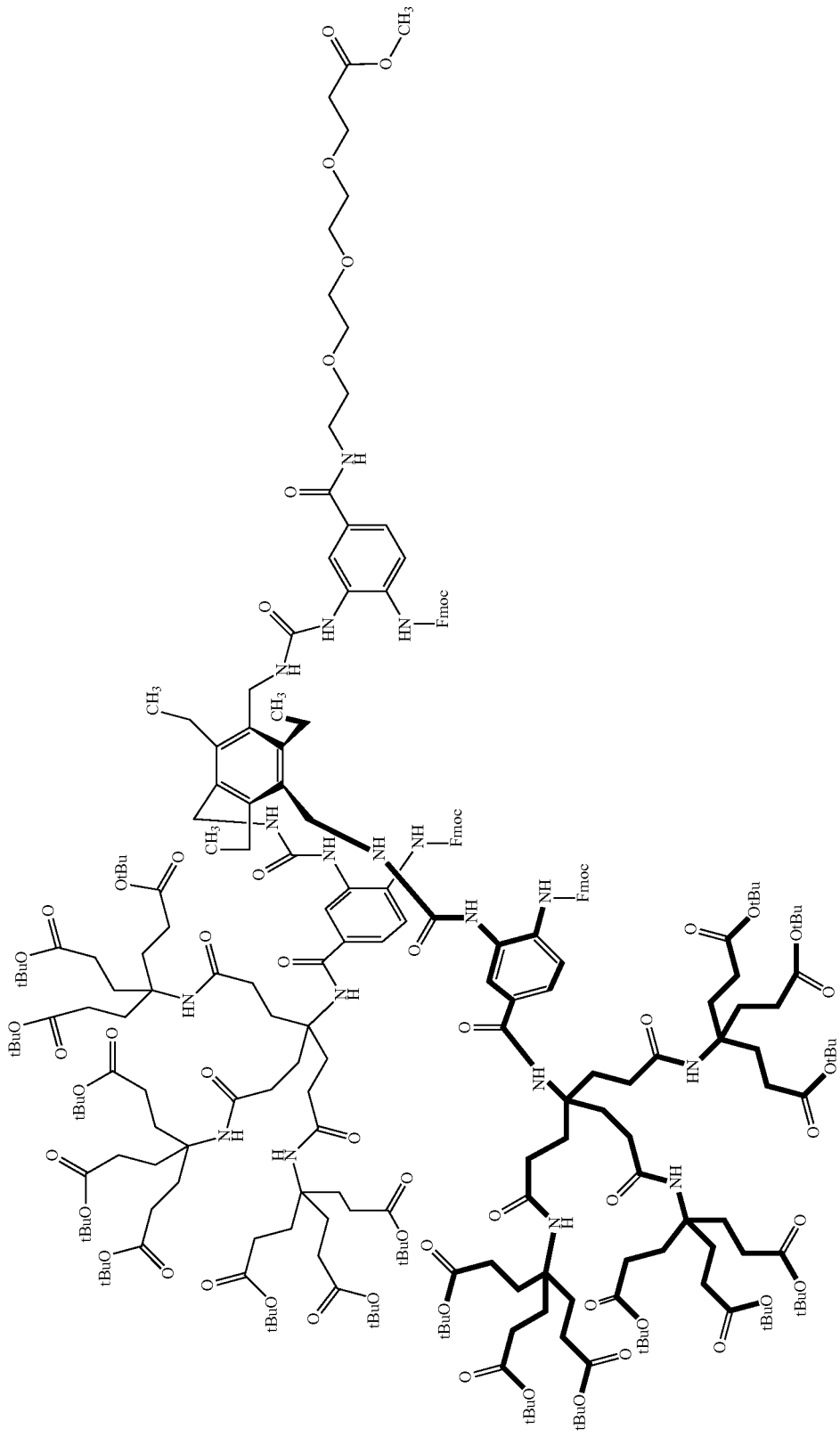

Compound 7a was prepared in an analogous fashion to compound 6a using compound 5b and compound 2b.

Preparation of Compound 7b

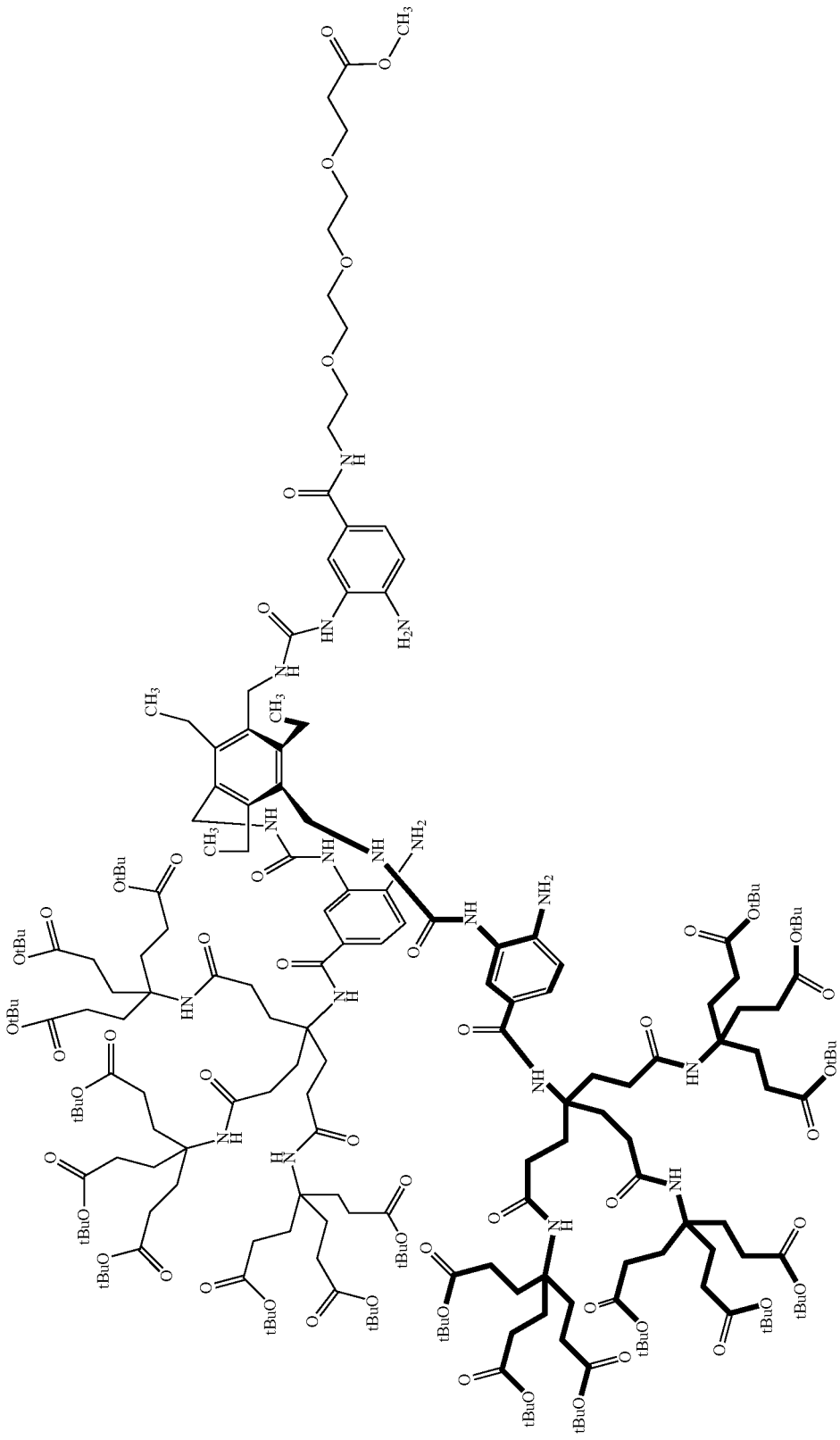

Compound 7b was prepared in an analogous fashion to Compound 6b using compound 7a.

Preparation of Compound 7c

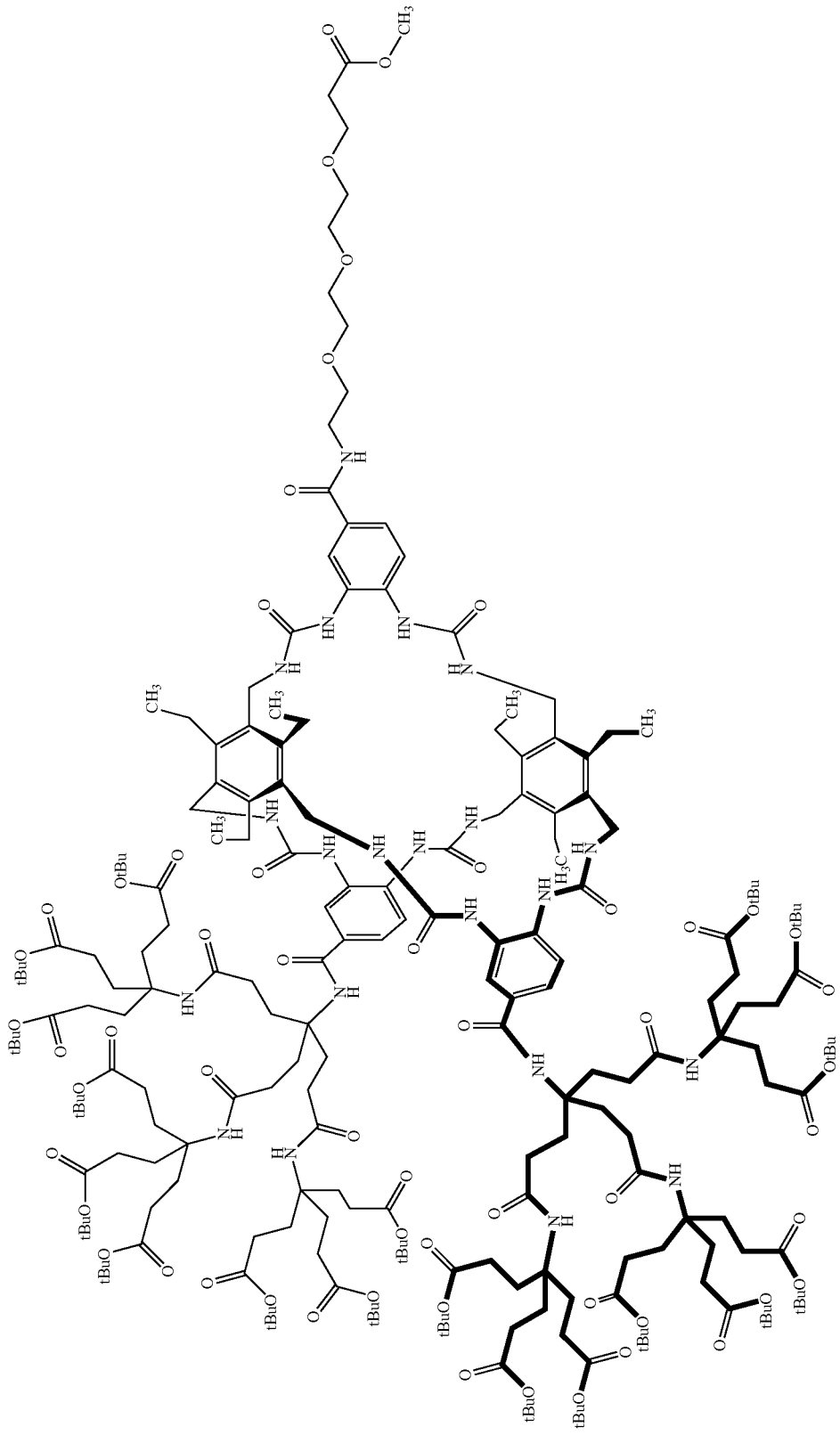

Compound 7c was prepared in an analogous fashion to Compound 6c using Compound 7b.

Preparation of Compound 7d

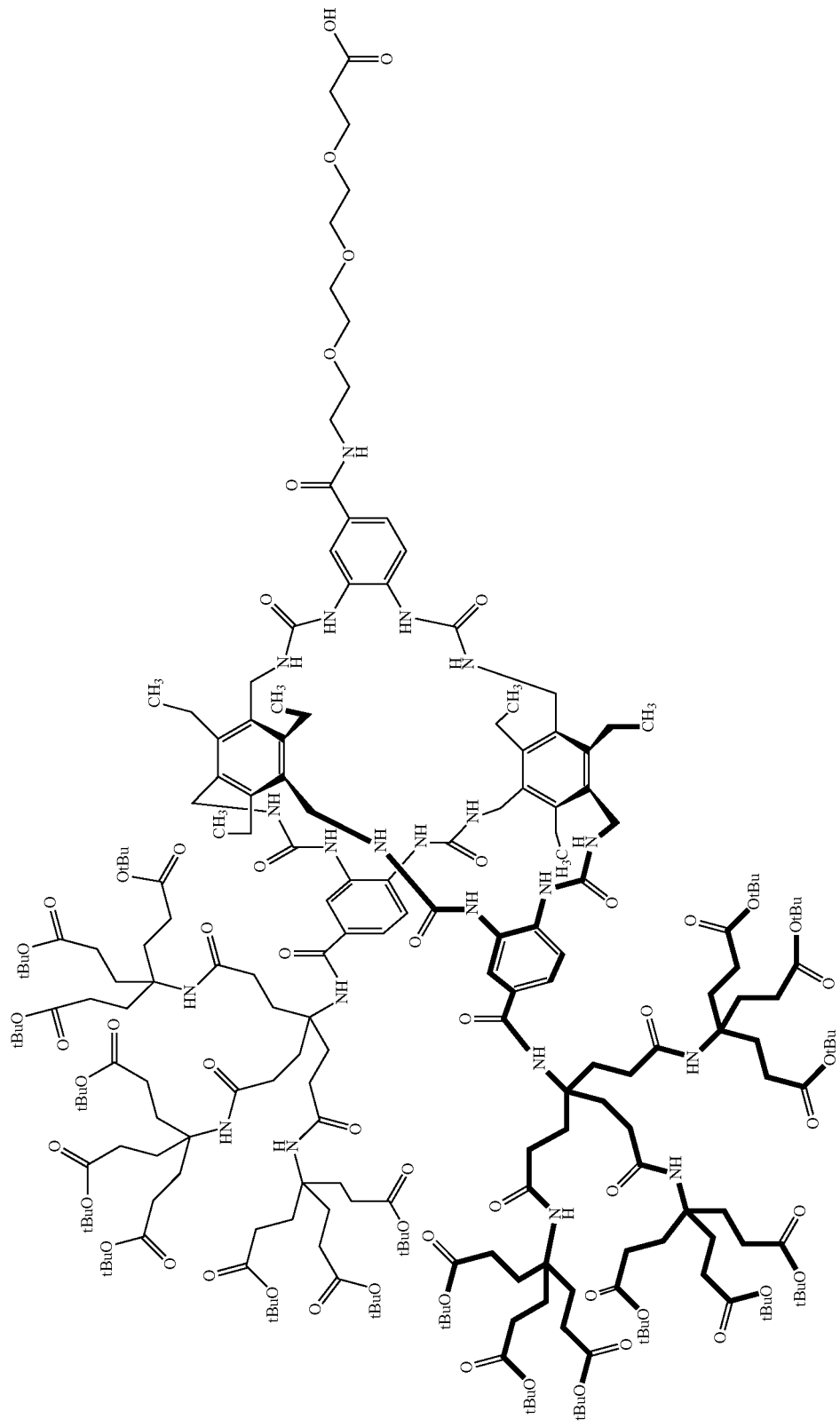

Compound 7c (421.6 mg 0.1 mmol) was dissolved in THF (10 mL) and 0.5 M NaOH (aq) (10 mL) and stirred for 2 hours. The THF was removed under reduced pressure and the resulting suspension was taken to pH using 0.1 M $HCl_{(aq)}$ then extracted with DCM (2×10 mL). The combined organic extracts were combined and dried over MgSO4 and then evaporated to dryness to give and off-white solid 7d (420.1 mg, 0.99 mmol, 99%).

Preparation of O-succinimidyl PEG-beta-D-glucopyranoside carboxylate 8

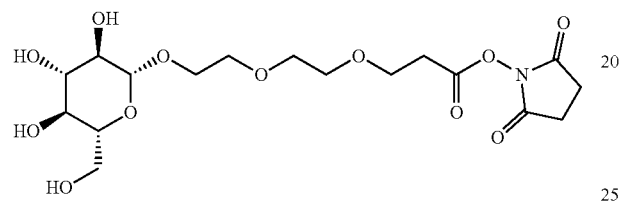

Succinimidyl ester beta-D-glucopyranoside PEG3 8 is prepared from the carboxylic acid (Sussex Research) dissolved in DMF, by transformation with N-hydroxysuccinimide (1 equivalent) and N,N-diisopropylcarbodiimide (1 equivalent).

Preparation of O-2,3,4,6-tetraacetyl-diethyleneglycol-beta-D-glucopyranoside 9

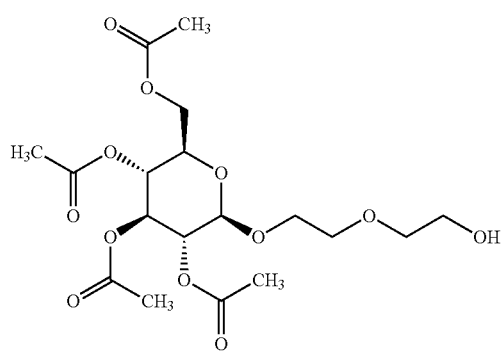

To O-peracetyl-alpha-bromo-D-glucopyranoside (3 g, 7.3 mmol) in 25 mL dichloroethane was added diethyleneglycol (8.9 g, 83.7 mmol) and 2 spoons of mol sieves then silver carbonate (3.6 g, 13.1 mmol) and the mixture stirred vigorously overnight. The mixture was diluted with 60 mL toluene and filtered through Celite to remove solids and the solution was then washed twice with brine and once with water, then dried over MgSO₄ and concentrated in vacuo. The oily crude residue was triturated with ether and white crystals formed. These were washed ×2 with diethyl ether and then dried in a dessicator to provide 9

Preparation of O-per-acetyl-diethyleneglycol-beta-glucopyranoside carboxylic acid 10

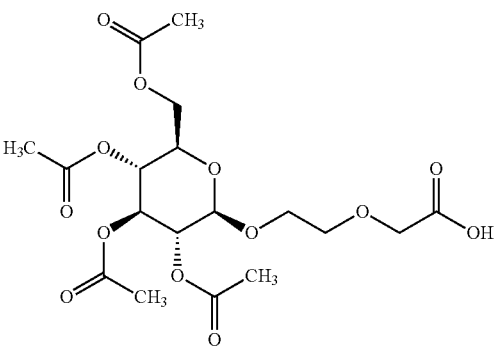

To a mixture of glucoside 9 (1.3 g, 2.979 mmol) in acetone (50 mL) was added saturated NaHCO₃ solution (10 mL) and the mixture was cooled in an ice bath. TEMPO (9.3 mg, 0.06 mmol) and NaBr 30.384 mg, 0.298 mmol) was then added followed by trichloroisocyanuric acid (1.38 g, 5.958 mmol) in small aliquots over about 20 mins. The reaction was then allowed to stir overnight (18 h). It was then partially concentrated in vacuo and acidified with HCl, then extracted with DCM 5 times (some salt added to aid phase separation) dried over MgSO₄ and concentrated to dryness to a white solid Preparation of O-succinimidyl O-per-acetyl-diethyleneglycol-beta-glucopyranoside carboxylate 11

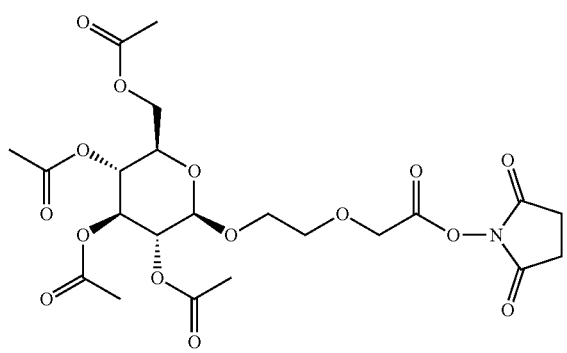

Carboxylic acid 10 (400 mg, 0.888 mmol) in THF (3 mL) was treated with N-hydroxysuccinimide (143 mg, 1.243 mmol) and DIC (179 mg, 1.421 mmol), stirred overnight and 11 was used in crude form for insulin acylations.

Preparation of D-glucopyranoside-1-PEG4-azide 12

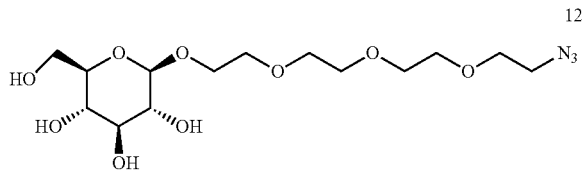 [SMILES: [N-]=[N+]=NCCOCCOCCOCCO[C@@H]1O[C@H](CO)[C@@H](O)[C@H](O)[C@H]1O]

D-glucopyranoside-1-PEG4-azide 12 was prepared as described in *J. Am. Chem. Soc.* 2017, 139, 3528.

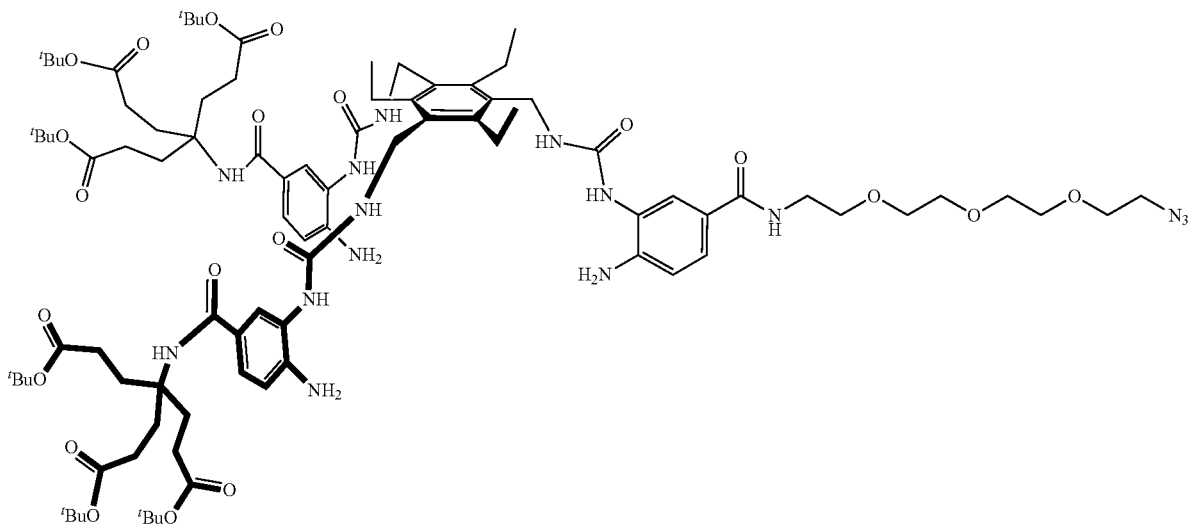

Preparation of Compound 13

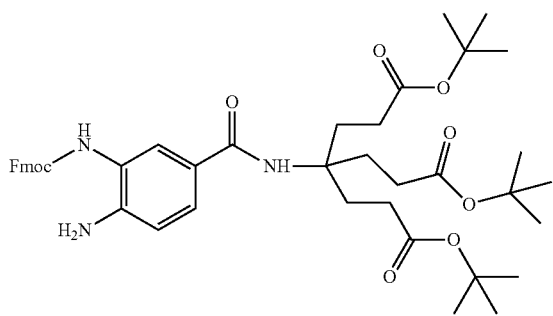

A 50 mL flask was charged with compound 1 (500 mg, 1.017 mmol), di-tert-butyl-4-amino-4-(3-(tert-butoxy)-3-oxopropyl)heptanedioate (Frontier Scientific—NTN1963, 560 mg, 1.35 mmol) and anhydrous toluene (10 mL). The slurry was evaporated to dryness and the residue re-dissolved in anhydrous pyridine (5 mL) and DCM (3 mL). The mixture was stirred at 50° C. for 16 hours. The solvent was removed to give a viscous brown oil, which was partitioned between EtOAc and 1M aq. HCl. The organic phase was washed with water then brine. The combined organic fractions were concentrated and then absorbed onto silica gel and purified by flash chromatograohy (EtOAc:DCM (20/50%) to give 13 (467 mg, 0.612 mmol, 60%). 1H NMR: (400 MHz, CDCl3) δ 7.79 (d, J=7.6 Hz, 2H, ArH), 7.64 (d, J=2.1 Hz, 1H, ArH), 7.43 (t, J=7.5 Hz, 2H, ArH), 7.34 (s, 3H, ArH), 6.78 (d, J=9.0 Hz, 1H, NH), 6.60 (s, 1H, ArH), 6.30 (s, 1H, ArH), 4.56 (s, 2H, Flu-CH2O), 4.28 (s, 1H, Flu-CH2), 4.08 (s, 2H), 2.30 (dd, J=8.8, 6.7 Hz, 6H, CH2C(O)), 2.16-2.04 (m, 6H, CCH2), 1.44 (s, 24H, C(CH3)3)

Preparation of Compound 14

Compound 13 (2.36 g, 3.06 mmol, 2.0 eq) and Compound 2b (0.50 g, 1.53 mmol, 1.0 eq) were dissolved in anhydrous THF (20.6 mL) and heated to 50° C. for 2 h. Compound 3 (1.32 g, 2.29 mmol, 1.5 eq) was then added as a solid and the reaction left overnight at 50° C. DBU (1.4 mL, 9.2 mmol, 6.0 eq) was added to the heterogenous reaction mixture. The solvent was removed and the residue dry loaded onto C18 using DCM and then loaded onto a 120 g C18 cartridge and purified by reverse phase flash chromatography (50 to 100% MeOH:water gradient). The product containing fractions were identified by TLC and concentrated under vacuum to give a light pink solid. The impure fractions were combined and re-purified to give 14 (859 mg, 32%).

$^1$H NMR (400 MHz, Methanol-$d_4$) δ 7.35 (d, J=8.3 Hz, 1H), 7.32 (d, J=8.3 Hz, 2H), 7.24 (d, J=2.1 Hz, 1H), 7.17 (d, J=2.0 Hz, 2H), 7.12 (dd, J=8.3, 2.1 Hz, 1H), 7.06 (dd, J=8.2, 2.1 Hz, 2H), 4.48 (s, 6H), 3.67-3.55 (m, 12H), 3.51 (t, J=5.4 Hz, 2H), 3.31 (t, J=5.2 Hz, 2H), 2.86 (q, J=7.4 Hz, 6H), 2.23 (dd, J=9.5, 6.5 Hz, 12H), 2.05 (dd, J=9.5, 6.5 Hz, 12H), 1.41 (s, 54H), 1.22 (t, J=7.4 Hz, 9H).

$^{13}$C NMR (101 MHz, Methanol-$d_4$) δ 174.6, 170.4, 170.3, 158.1, 145.2, 142.0, 133.9, 133.5, 129.5, 125.0, 125.0, 118.5, 118.4, 117.1, 81.8, 71.6, 71.5, 71.3, 71.1, 70.6, 59.3, 51.7, 49.8, 40.9, 40.3, 39.3, 30.8, 30.6, 28.4, 23.9, 16.9.

HRMS [M+2H]$^{2+}$ calculated for $C_{91}H_{141}N_{15}O_{21}$ requires: 890.0213, found: 890.0206

Preparation of Compound 15

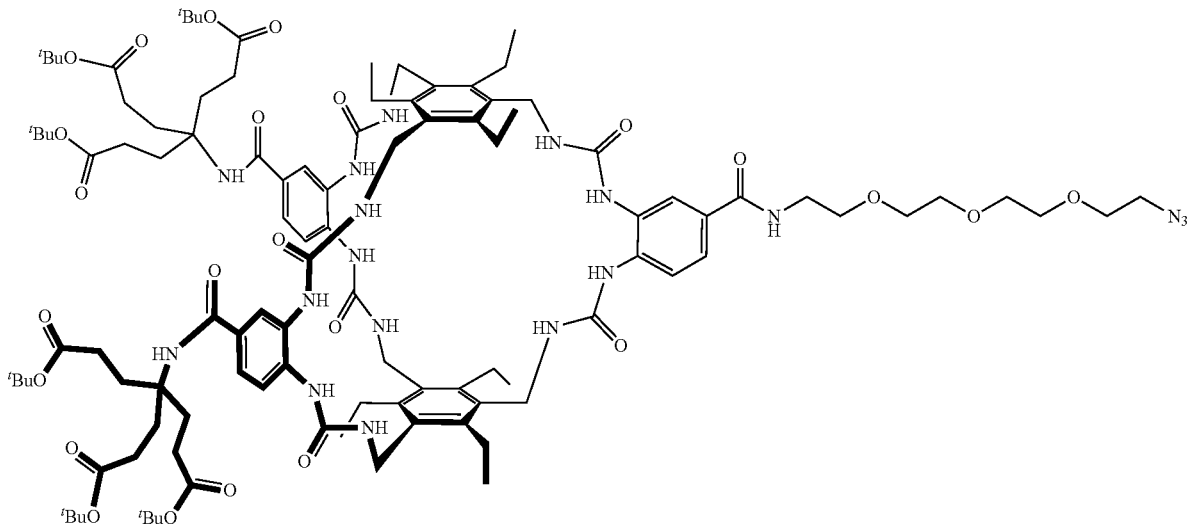

Compound 14 (0.820 g, 0.461 mmol, 1.0 eq) was dissolved in anhydrous pyridine (192 mL) and heated to 45° C. under nitrogen. In a separate pear-shaped vial compound 2b (0.181 g, 0.553 mmol, 1.2 eq) was dissolved in anhydrous $CH_2Cl_2$ (19.2 mL) and add to the solution of compound 14 via syringe pump (Rate: 2.0 mL/hr, 10 h addition). The reaction mixture was concentrated under vacuum to give an orange solid which was azeotroped with toluene (100 mL). The crude residue was dissolved in MeCN (2 mL) and loaded onto a C18 cartridge and purified by reverse phase flash chromatography (60 to 100% acetone:water gradient). The product containing fractions were identified by TLC and concentrated under vacuum to give an orange/pink solid (0.372 g, 38%).

$^1$H NMR (400 MHz, Methanol-$d_4$) δ 8.01 (d, J=2.1 Hz, 1H), 7.95 (d, J=8.6 Hz, 2H), 7.92 (d, J=8.7 Hz, 1H), 7.88 (d, J=2.0 Hz, 2H), 7.62 (s, 2H), 7.58-7.51 (m, 3H), 4.55-4.30 (m, 12H), 3.64-3.52 (m, 12H), 3.53-3.48 (m, 2H), 3.46-3.36 (m, 2H), 2.92-2.81 (m, 6H), 2.78-2.66 (m, 6H), 2.29-2.20 (m, 12H), 2.11-2.04 (m, 12H), 1.43 (s, 54H), 1.18 (t, J=7.1 Hz, 18H).

$^{13}$C NMR (101 MHz, Methanol-$d_4$) δ 174.6, 169.7, 158.4, 158.3, 157.2, 144.5, 136.8, 134.3, 133.9, 131.5, 130.2, 129.9, 129.5, 125.6, 125.5, 125.2, 122.3, 81.7, 71.7, 71.5, 71.4, 71.3, 71.1, 70.6, 59.5, 51.7, 40.9, 38.8, 38.7, 30.8, 30.6, 28.4, 24.2, 23.6, 16.6.

HRMS [M+2H]$^{2+}$ calculated for $C_{109}H_{162}N_{18}O_{24}$ requires: 1054.1021, found: 1054.1028.

Preparation of Compound 16

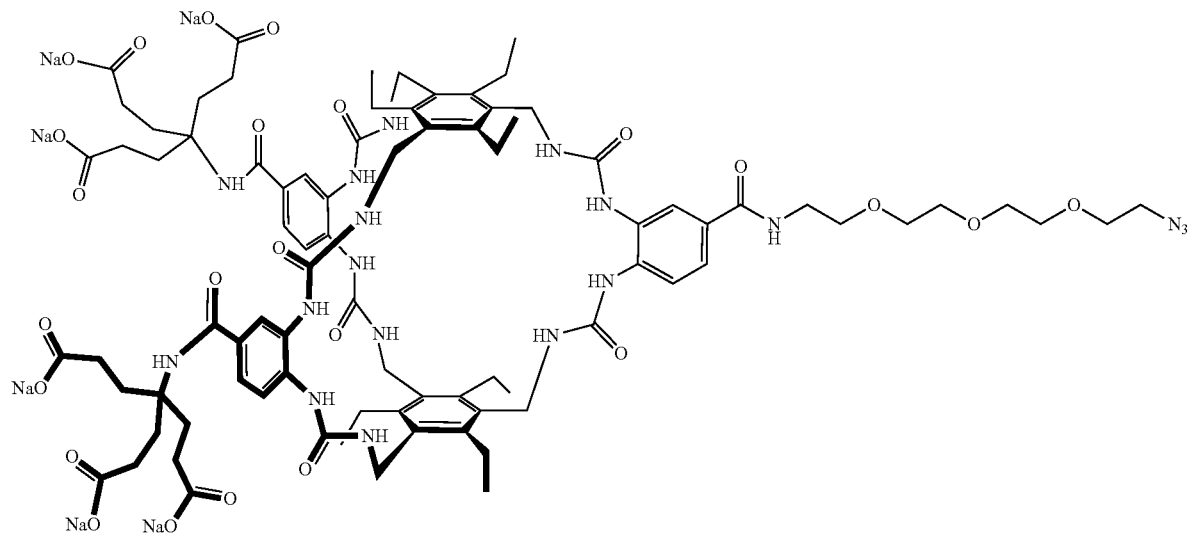

Compound 15 (190 mg, 0.090 mmol) was dissolved in $CH_2Cl_2$ (9 mL) and TFA (6.2 mL, 81 mmol) and stirred for 16 hours at room temperature. The reaction mixture was poured into water (90 mL) and the suspension bubbled with nitrogen for 30 min to remove any $CH_2Cl_2$. The resulting white solid was collected by centrifugation. The pellet was re-suspended in water (30 mL) and centrifuged. The supernatant was decanted, and the resulting solid was re-suspended in water (25 mL) and neutralised to pH 7.4 by the addition of aqueous NaOH. Sonication between additions was required to ensure all the material became fully soluble. Once homogenous at the desired pH the solution was passed through a 0.22 μm PES syringe filter and then lyophilized to give 16 (170 mg, 99%).

$^1$H NMR (400 MHz, $D_2O$ with 100 mM phosphate buffer and 2 mM DMF) δ 7.91-7.22 (m, 9H), 4.32 (br. s, 12H), 3.72-3.32 (m, 14H), 3.21 (s, 2H), 2.62 (br. s, 12H), 2.04 (br. s, 12H), 1.91 (br. s, 12H), 1.04 (br. s, 18H).

Preparation of Compound 17

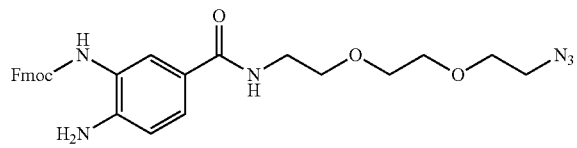

Prepared as for compound 3 using commercial 2-(2-(2-azidoethoxy)ethoxy)ethan-1-amine. White solid 17 (3.2 g, 71%).

$^1$H NMR (400 MHz, Methanol-$d_4$) δ 7.97 (t, J=5.6 Hz, 1H), 7.87-7.56 (m, 4H), 7.56-7.17 (m, 5H), 6.79 (d, J=8.4 Hz, 1H), 4.49 (s, 2H), 4.27 (s, 1H), 3.70-3.59 (m, 8H), 3.54 (q, J=5.2 Hz, 2H), 3.35-3.25 (m, 2H).

HRMS [M+H]$^+$ calculated for $C_{28}H_{31}N_6O_5$ requires: 531.2351, found: 531.2362.

Preparation of Compound 18

Prepared as described for compound 14 using compound 17, white solid 18 (0.78 g, 86%)

$^1$H NMR (400 MHz, Methanol-$d_4$+$CDCl_3$) δ 7.36-7.29 (m, 3H), 7.22 (d, J=2.1 Hz, 1H), 7.18 (d, J=2.1 Hz, 2H), 7.10 (dd, J=5.0, 2.0 Hz, 1H), 7.07 (dd, J=5.0, 2.1 Hz, 2H), 4.48 (s, 6H), 3.69-3.60 (m, 8H), 3.54 (t, J=5.4 Hz, 2H), 3.34 (t, J=5.0 Hz, 2H), 2.85 (q, J=7.2 Hz, 6H), 2.30-2.21 (m, 12H), 2.11-2.02 (m, 12H), 1.43 (s, 54H), 1.23 (t, J=7.2 Hz, 9H).

$^{13}$C NMR (101 MHz, Methanol-$d_4$+$CDCl_3$) δ 174.5, 170.1, 170.0, 169.9, 157.9, 157.8, 144.9, 141.6, 141.5, 133.6, 133.1, 133.0, 132.1, 129.5, 129.4, 125.0, 124.9, 118.5, 118.4, 116.9, 116.9, 81.8, 71.3, 71.2, 70.9, 70.5, 59.1, 59.0, 51.5, 40.7, 39.2, 30.8, 30.7, 30.5, 28.4, 23.7, 16.9

HRMS [M+2H]$^{2+}$ calculated for $C_{89}H_{137}N_{15}O_{20}$ requires: 868.0082, found: 868.0085

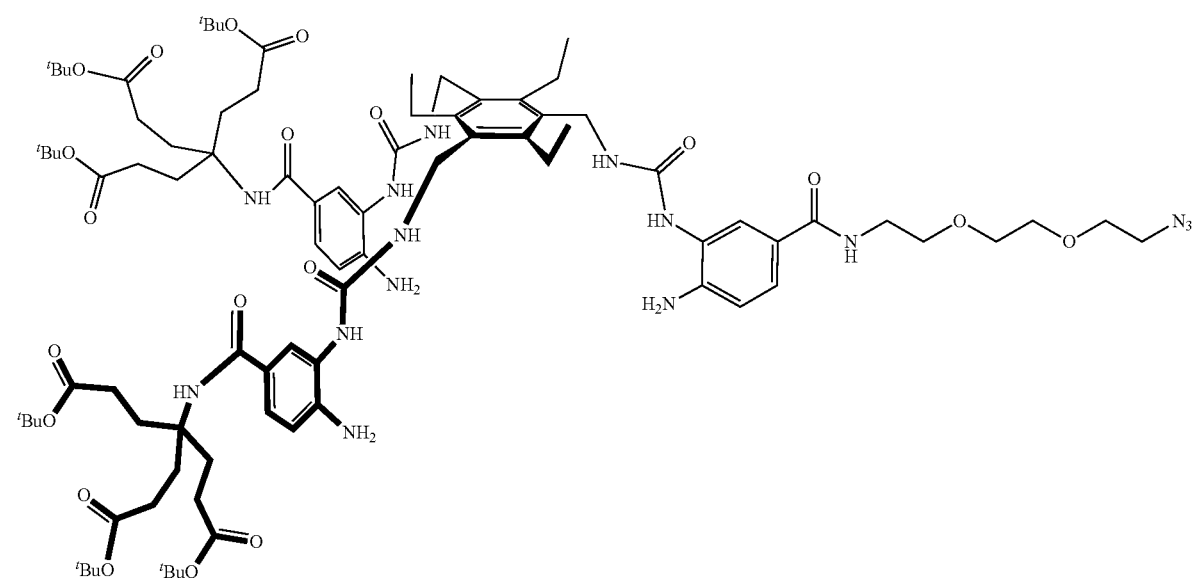

Preparation of Compound 19
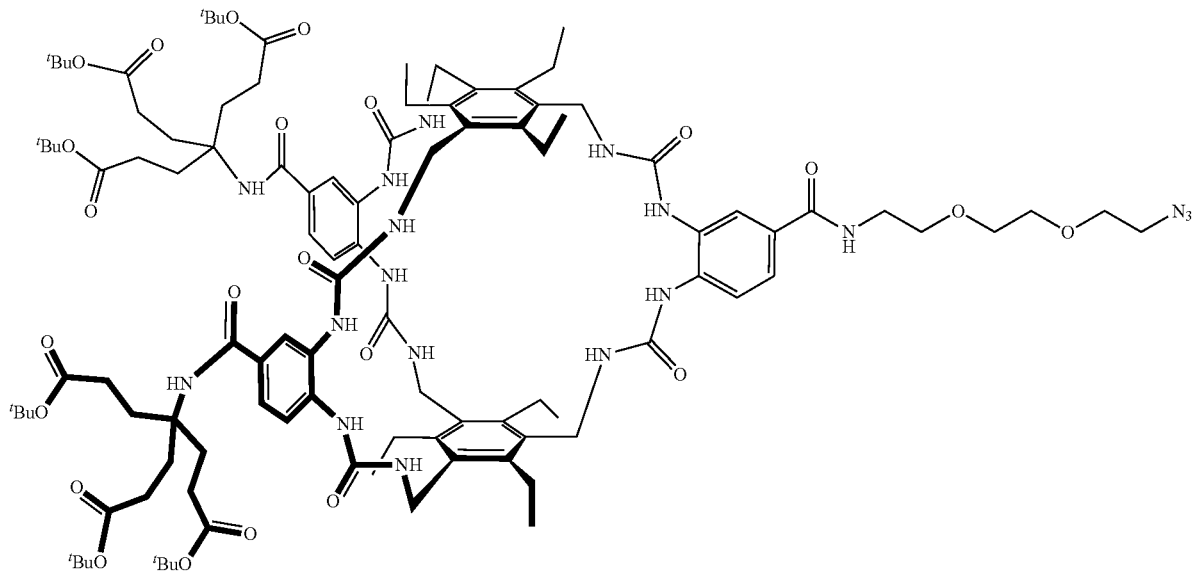
Prepared as described for compound 15 using compound 18. to give white solid 19 (449 mg, 48%).
$^1$H NMR (400 MHz, Methanol-$d_4$) δ 8.03 (d, J=2.1 Hz, 1H), 7.99-7.91 (m, 3H), 7.89 (d, J=2.1 Hz, 2H), 7.65 (s, 2H), 7.59 (dd, J=8.6, 2.1 Hz, 1H), 7.55 (dd, J=8.6, 2.1 Hz, 2H), 4.54-4.35 (m, 12H), 3.68-3.62 (m, 6H), 3.60 (t, J=5.2 Hz, 2H), 3.49 (t, J=5.6 Hz, 2H), 3.35 (t, J=4.9 Hz, 2H), 2.94-2.83 (m, 6H), 2.83-2.71 (m, 6H), 2.33-2.23 (m, 12H), 2.12-2.06 (m, 12H), 1.45 (s, 54H), 1.23-1.16 (m, 18H).
$^{13}$C NMR (101 MHz, Methanol-$d_4$) δ 174.6, 169.8, 169.7, 158.4, 158.3, 157.3, 144.5, 136.9, 134.3, 133.9, 133.9, 131.5, 130.4, 130.0, 129.6, 125.6, 125.5, 122.6, 122.4, 81.7, 71.5, 71.5, 71.1, 70.7, 59.5, 51.7, 40.9, 38.8, 38.7, 30.8, 30.6, 28.4, 23.6, 16.6, 16.6.
HRMS [M+2H]$^{2+}$ calculated for $C_{107}H_{158}N_{18}O_{23}$ requires: 1031.5874, found: 1031.5889
Preparation of Compound 20
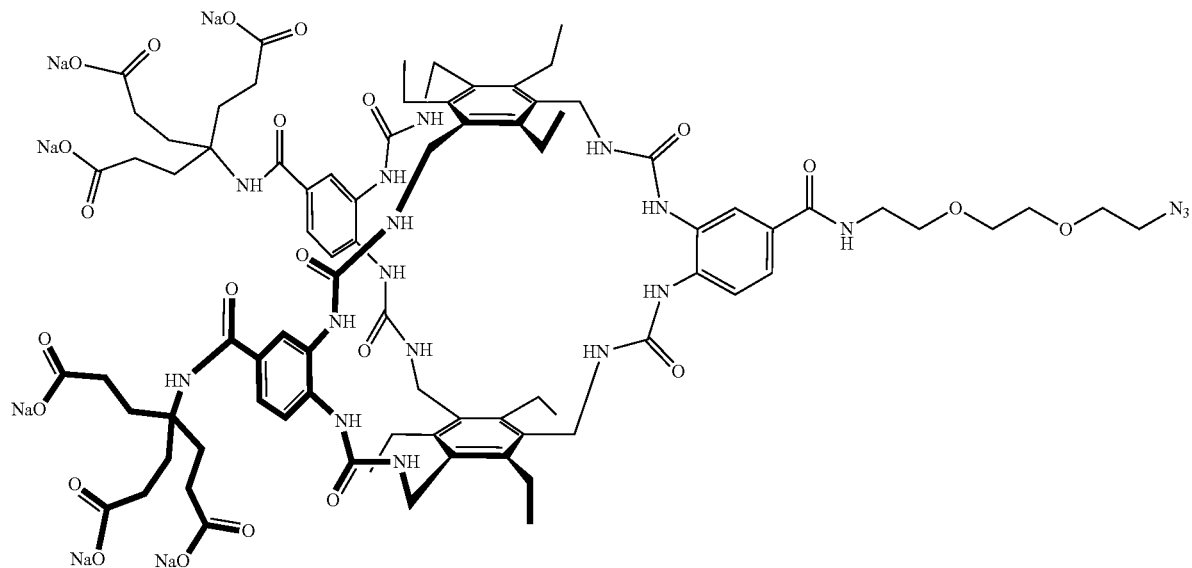

Prepared as described for compound 16 using compound 19, to give white solid 20 (380 mg, 94%). The purity assayed at ca. 75% by weight by relative integration to a DMF internal standard using $^1$H NMR spectroscopy.

$^1$H NMR (400 MHz, D$_2$O with 100 mM phosphate buffer and 2 mM DMF) δ 8.07-7.20 (m, 9H), 4.27 (s, 12H), 3.61-3.33 (m, 10H), 3.19 (s, 2H), 2.55 (s, 12H), 2.03 (s, 12H), 1.90 (s, 12H), 1.00 (s, 18H).

Preparation of Compound 21, G1 Macrocycle Propyl Azide

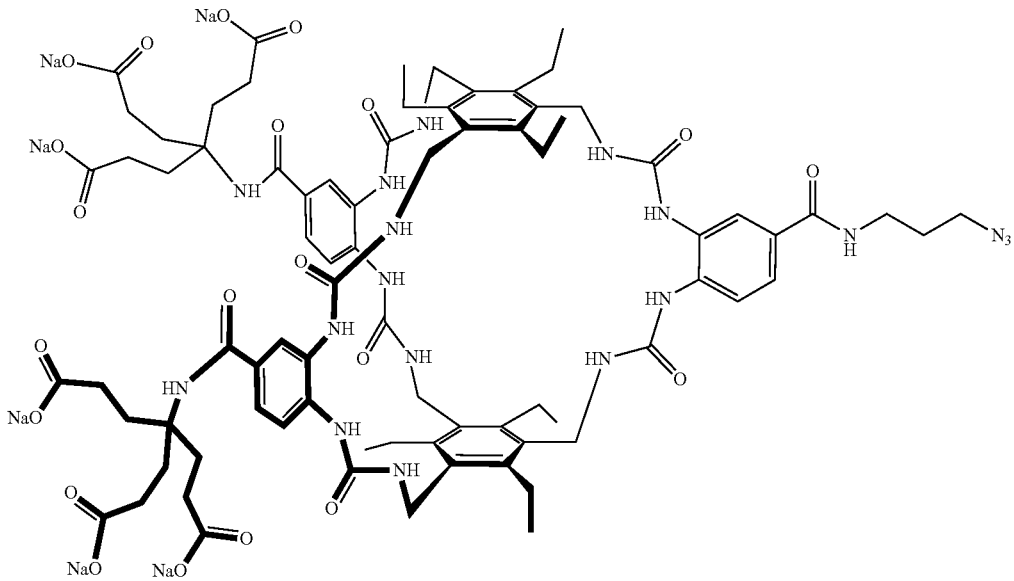

Step 1: Preparation of Compound 21a

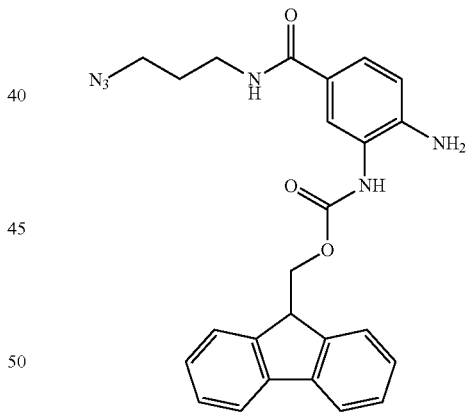

Compound 1 was dissolved in anhydrous THF (110.5 mL) and stirred while DIPEA (4.1 mL, 23.731 mmol) was added. 3-Azidopropylamine (0.750 g, 6.742 mmol) was added and the homogenous solution was allowed to stir overnight. The solvent was removed to dryness to give a pink solid which was suspended in DCM (10 mL) and MeOH (ca 10 mL) and warmed to give a solution. The solution was concentrated on a rotary evaporator which caused a white solid to precipitate. The precipitate was collected and washed with DCM (2×3 mL) and then petrol (2×5 mL) and then dried under high vacuum to give an off white solid 21a (1.8 g, 3.94 mmol, 59%). $^1$H NMR (400 MHz, methanol-d$_4$) δ 8.57 (d, J=7.6 Hz, 2H), 8.48-8.40 (m, 2H), 8.21 (s, 1H), 8.13 (t, J=7.4 Hz, 2H), 8.06 (s, 1H), 7.47 (d, J=8.4 Hz, 1H), 5.22-5.14 (m, 2H), 5.05-4.95 (m, 2H), 4.08 (dt, J=10.3, 6.8 Hz, 4H), 4.00-3.91 (m, 1H), 2.52 (p, J=6.8 Hz, 2H).

Step 2: Preparation of Compound 21b

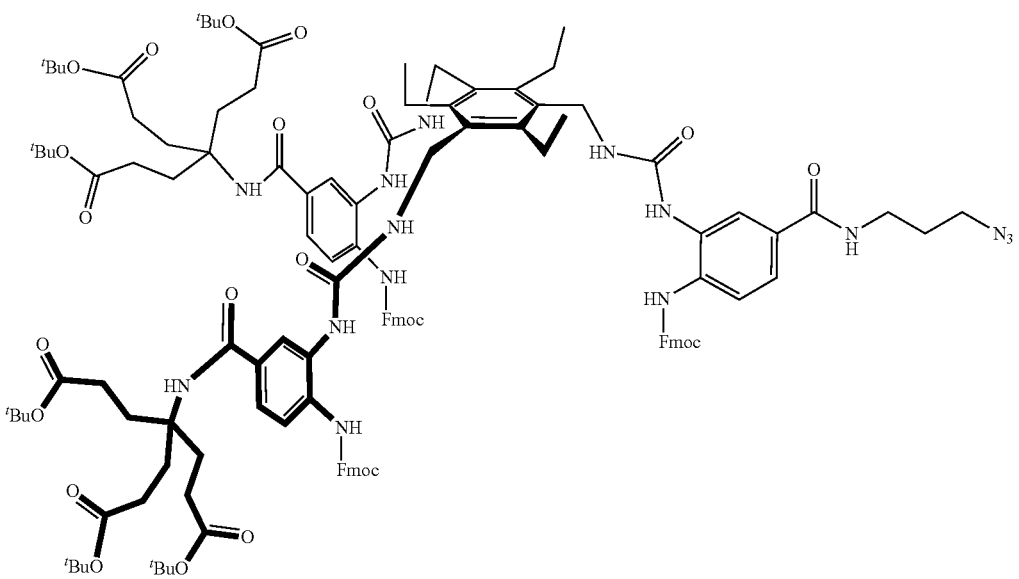

Made from compound 4 (2.358 g, 3.055 mmol), 21a (1.046 g, 2.291 mmol) and 2b (500 mg, 1.527 mmol) as per compound 6a. The product isolated as an off-white amorphous solid 21b (1.17 g, 0.503 mmol, 33%). $^1$H NMR (400 MHz, Methanol-d$_4$) δ 8.31-7.00 (m, 33H), 4.43-3.97 (m, 15H), 3.37 (t, J=6 Hz, 2H), 3.30 (m, 2H), 2.76 (br. s, 6H), 2.25-2.19 (m, 12H), 2.10-2.03 (m, 12H), 1.79 (p, J=6 Hz, 2H) 1.39 (s, 54H), 1.18-1.12 (m, 9H).

Step 3: Preparation of Compound 21c

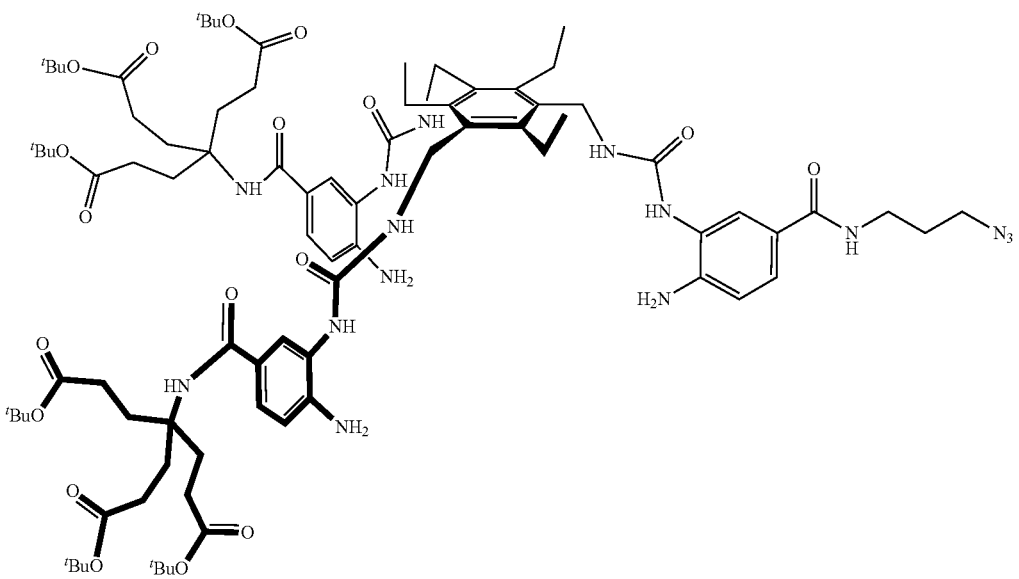

Made from compound 21b (1.17 g, 0.503 mmol) as per compound 6b. The product isolated as an off-white amorphous solid compound 21c (0.702 g, 0.423 mmol, 84%). $^1$H NMR (400 MHz, Methanol-d$_4$) δ 7.36 (d, J=8.4 Hz, 1H), 7.34 (d, J=8.3 Hz, 2H), 7.25 (d, J=2.1 Hz, 1H), 7.19 (d, J=2.1 Hz, 2H), 7.12 (dd, J=8.3, 2.1 Hz, 1H), 7.08 (dd, J=8.2, 2.1 Hz, 2H), 4.50 (s, 6H), 3.42 (t, J=6.8 Hz, 2H), 3.39 (t, J=6.7 Hz, 2H), 2.88 (q, J=7.0 Hz, 6H), 2.31-2.20 (m, 12H), 2.12-2.01 (m, 12H), 1.85 (p, J=6.7 Hz, 2H), 1.43 (s, 54H), 1.24 (t, J=7.4 Hz, 9H). $^{13}$C NMR (101 MHz, Methanol-d$_4$) δ 174.6, 170.4, 170.4, 158.1, 158.1, 145.1, 142.0, 141.9, 133.9, 133.5, 132.4, 129.7, 129.5, 125.0, 125.0, 118.5, 118.3, 117.0, 81.8, 59.3, 50.2, 39.3, 38.3, 30.8, 30.6, 29.8, 28.3, 23.9, 16.9. HRMS ([M+H]$^+$ calculated for C$_{86}$H$_{130}$N$_{15}$O$_{18}$ requires: 1660.9718, found: 1660.9723.

Step 4: Preparation of Compound 21d

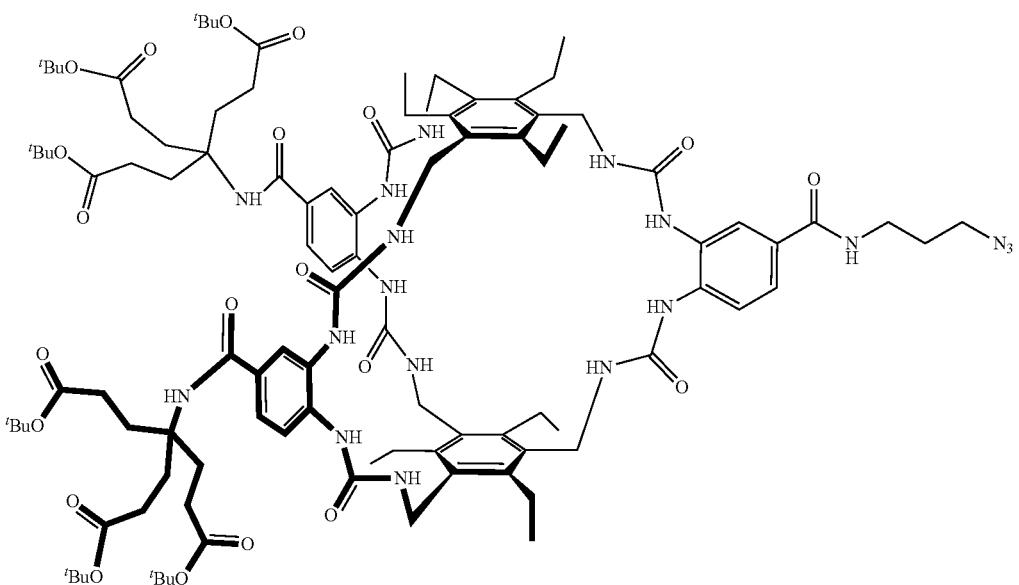

Made from compound 21c (740 mg, 0.445 mmol) and 2b (175 mg, 0.535 mmol) as per compound 6c, with the addition of 20% DMF to the solvent, heated to 45° C. The product isolated as a white amorphous solid compound 21d (0.254 g, 0.128 mmol, 29%). $^1$H NMR (400 MHz, Methanol-$d_4$) δ 8.05 (d, J=2.1 Hz, 1H), 7.96 (d, J=8.6 Hz, 2H), 7.95 (d, J=8.5 Hz, 1H), 7.91 (d, J=2.1 Hz, 2H), 7.57 (dd, J=8.6, 2.2 Hz, 1H), 7.53 (dd, J=8.6, 2.1 Hz, 2H), 4.47 (s, 6H), 4.42 (s, 6H), 3.48-3.39 (m, 4H), 2.94-2.80 (m, 6H), 2.80-2.71 (m, 6H), 2.33-2.23 (m, 12H), 2.13-2.05 (m, 12H), 1.88 (p, J=6.7 Hz, 2H), 1.45 (s, 54H), 1.20 (t, J=7.3 Hz, 18H). $^{13}$C NMR (101 MHz, Methanol-$d_4$) δ 174.6, 169.8, 169.7, 158.3, 158.2, 157.3, 157.2, 144.5, 144.5, 136.5, 136.3, 134.2, 134.1, 133.8, 133.8, 131.3, 130.4, 130.0, 129.5, 125.4, 125.1, 124.9, 122.6, 122.4, 81.7, 59.4, 50.2, 38.8, 38.4, 30.8, 30.7, 30.6, 29.8, 28.4, 23.6, 16.6, 16.6. HRMS [M+2H]$^{2+}$ calc. $C_{104}H_{150}N_{18}O_{21}$ requires: 994.5690, found: 994.5684

Step 5: Preparation of Compound 21, G1 Macrocycle Propyl Azide

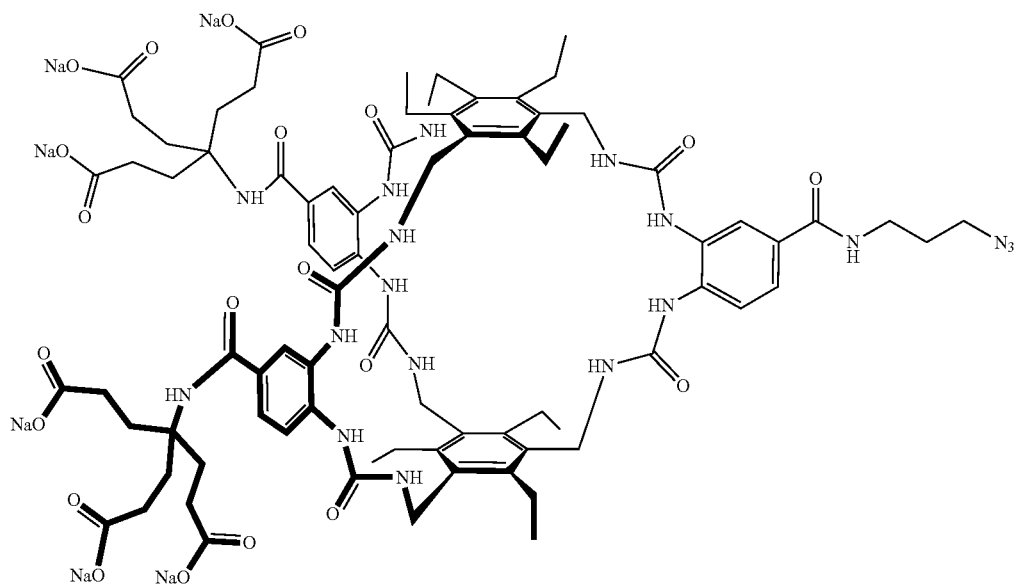

21

Made from compound 21d (240 mg, 0.121 mmol) as per compound 6d. The product isolated after neutralisation to pH 7.5 with NaOH and lyophilized as a white amorphous solid 21 (187 mg, 0.105 mmol, 87%). $^1$H NMR (400 MHz, deuterated phosphate buffer in D$_2$O) δ 8.12-7.12 (m, 9H), 4.41-3.92 (m, 12H), 3.33 (m, 4H), 2.66-2.26 (m, 12H), 2.20-1.52 (m, 26H), 1.31-0.74 (m, 18H).

Preparation of Compound 22, G2 Macrocycle PEG3 Azide:

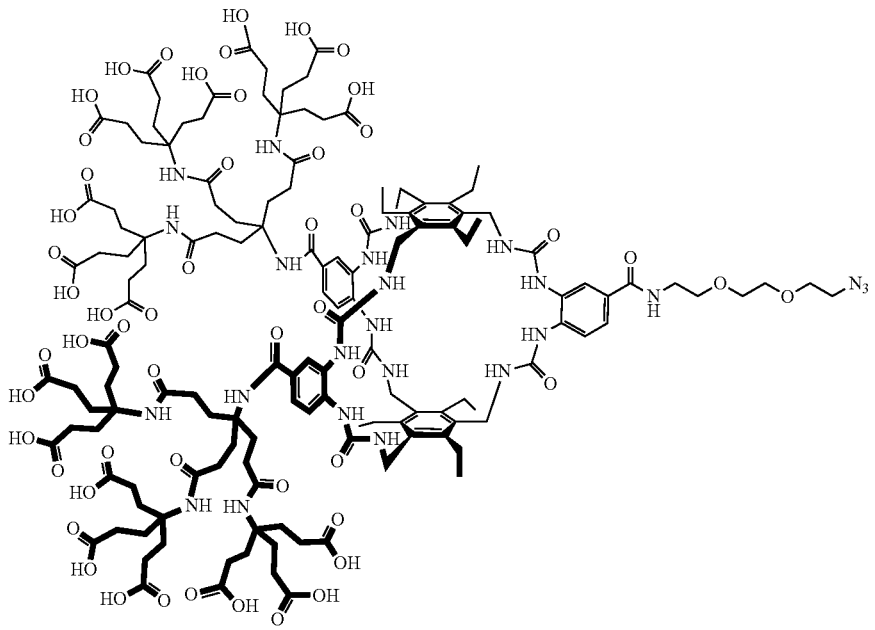

Step 1: Preparation of Compound 22a

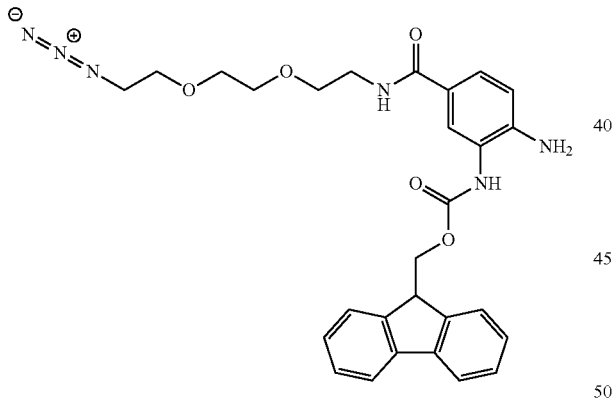

Dissolve compound 1 (7.00 g, 8.55 mmol, 1.0 eq) in anhydrous THF (85.5 mL) and add DIPEA (3.0 mL, 17 mmol, 2.0 eq). Add N3-(PEG)$_2$-NH2 (1.94 g, 11.1 mmol, 1.3 eq) and stir at RT. Concentrated the reaction mixture under vacuum and then dissolved in MeCN for RP MPLC. Product containing fractions were combined and concentrated under vacuum. Dry loaded onto silica gel with EtOAc/MeOH and then purified by NP MPLC. Product containing fractions combined and concentrated under vacuum to give an orange oil. Addition of petrol/CH$_2$Cl$_2$ and then EtOAc caused a precipitation to occur. Precipitate collected by filtration, washing with petrol to give an off white solid compound 22a (3.210 g, 6.050 mmol, 71%). $^1$H NMR (400 MHz, Methanol-d$_4$) δ 7.97 (t, J=5.6 Hz, 1H), 7.87-7.56 (m, 5H), 7.56-7.17 (m, 5H), 6.79 (d, J=8.4 Hz, 1H), 4.49 (s, 2H), 4.27 (s, 1H), 3.70-3.59 (m, 8H), 3.54 (q, J=5.2 Hz, 2H), 3.35-3.25 (m, 2H). HRMS [m+H]$^+$ calculated for C$_{28}$H$_{31}$N$_6$O$_5$ requires: 531.2351, found: 531.2362.

Step 2: Preparation of Compound 22b
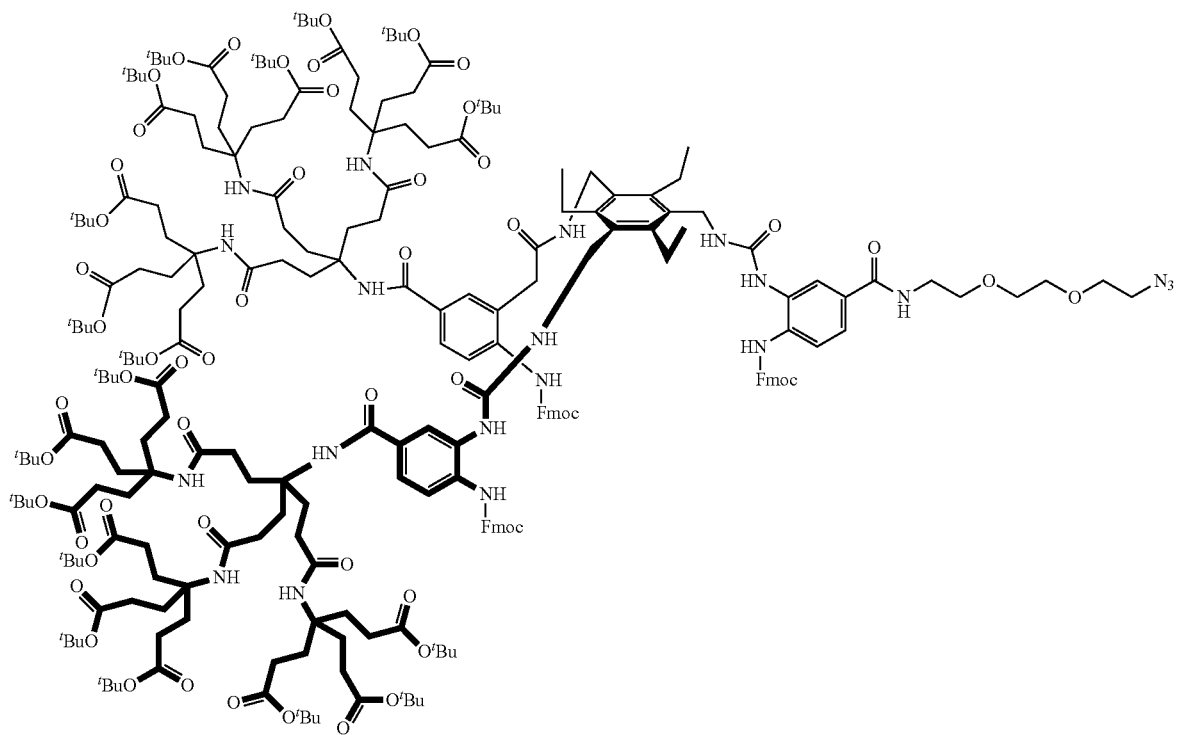
Made similarly to compound 6a from compound 21a and compound 4. $^1$H NMR (400 MHz, Methanol-$d_4$) δ 7.99-7.44 (m, 17H), 7.44-7.14 (m, 16H), 4.44 (s, 6H), 4.33 (br. s, 6H), 4.13 (br. s, 3H), 3.63-3.55 (m, 8H), 3.51 (t, J=5.1 Hz, 2H), 3.25 (t, J=5.0 Hz, 2H), 2.81 (br. s, 6H), 2.24-2.03 (m, 60H), 1.94-1.82 (m, 36H), 1.38 (s, 162H), 1.19-1.10 (m, 9H).
Step 3: Preparation of Compound 22c
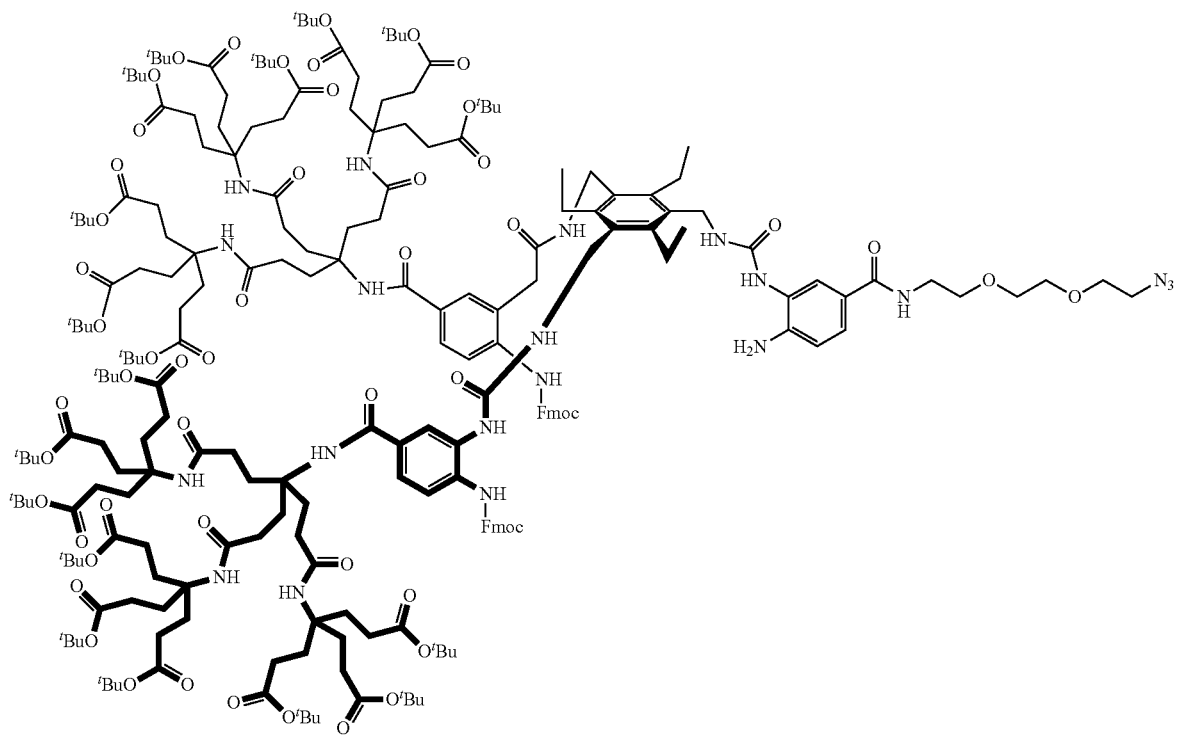

Made from compound 22b (2.75 g, 0.62 mmol) as per compound 6b. The product isolated as an off-white amorphous solid compound 22c (1.52 g, 0.403 mmol, 65%).

$^1$H NMR (500 MHz, Methanol-$d_4$) δ 7.39 (d, J=8.3 Hz, 2H), 7.37 (d, J=8.3 Hz, 1H), 7.29 (d, J=2.1 Hz, 2H), 7.27 (d, J=2.1 Hz, 1H), 7.21 (dd, J=8.3, 2.1 Hz, 2H), 7.14 (dd, J=8.3, 2.1 Hz, 1H), 4.51 (s, 6H), 3.67-3.62 (m, 8H), 3.54 (t, J=5.5 Hz, 2H), 3.34 (t, J=5.3 Hz, 2H), 2.89 (q, J=7.5 Hz, 6H), 2.27-2.22 (m, 12H), 2.21-2.15 (m, 36H), 2.12-2.07 (m, 12H), 1.99-1.88 (m, 36H), 1.43 (s, 162H), 1.25 (t, J=7.5 Hz, 9H). $^{13}$C NMR (126 MHz, Methanol-$d_4$) δ 175.5, 174.4, 170.3, 170.1, 158.0, 158.0, 145.2, 141.9, 141.5, 133.9, 132.9, 132.4, 129.9, 129.7, 124.9, 124.5, 118.9, 118.4, 117.4, 117.1, 81.7, 71.5, 71.4, 71.1, 70.7, 59.4, 58.7, 51.7, 40.9, 39.3, 32.5, 32.2, 30.7, 30.5, 28.4, 23.9, 17.0. HRMS [M+3H]$^{3+}$ calculated for $C_{197}H_{324}N_{21}O_{50}$ requires: 1261.4485, found: 1261.4509.

Step 4: Preparation of Compound 22d

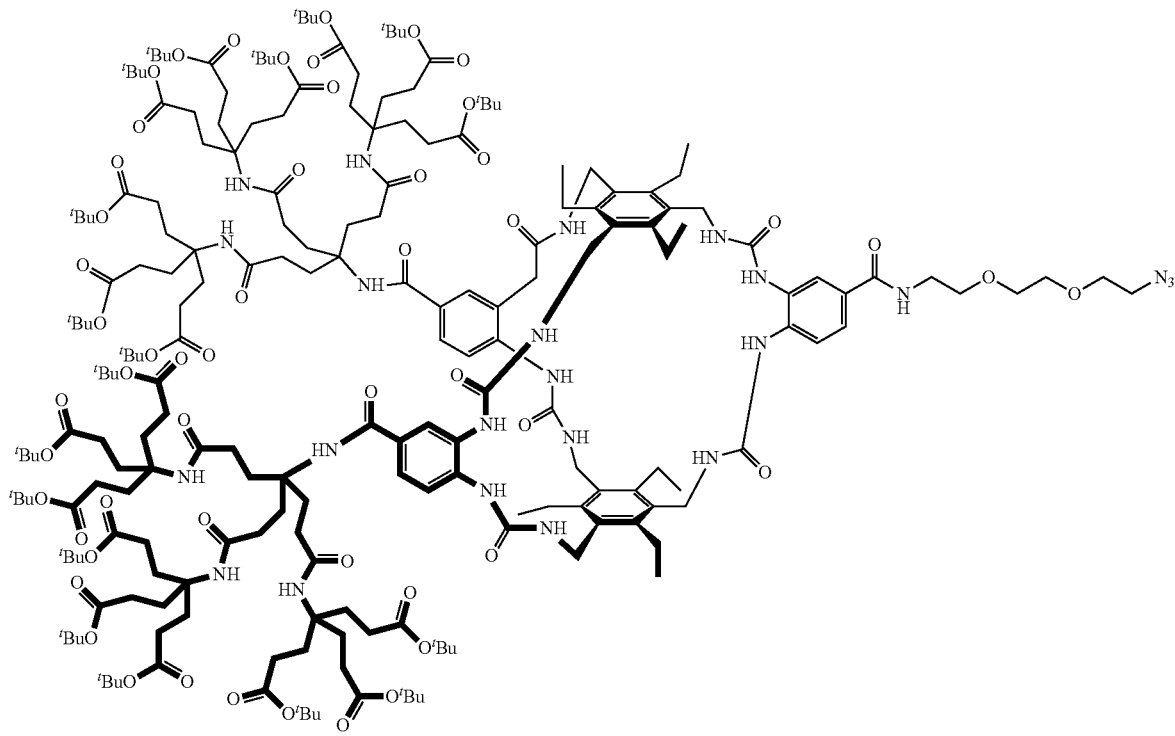

Made from compound 22c (1.50 g, 0.396 mmol) and 2b (156 mg, 0.476 mmol) as per compound 6c, with the addition of 20% DMF to the solvent, heated to 45° C. The product isolated as a white amorphous solid compound 22d (0.94 g, 0.229 mmol, 58%). $^1$H NMR (500 MHz, Methanol-$d_4$) δ 8.07 (s, 1H), 8.03 (d, J=2.1 Hz, 1H), 8.01-7.95 (m, 3H), 7.92 (d, J=8.6 Hz, 1H), 7.66 (dd, J=8.7, 2.0 Hz, 2H), 7.60 (dd, J=8.5, 2.1 Hz, 1H), 7.44 (s, 4H, NH signals slowly exchange so integration varies), 4.57-4.33 (m, 12H), 3.71-3.59 (m, 8H), 3.53 (t, J=5.5 Hz, 2H), 3.36 (t, J=5.2 Hz, 2H), 2.87 (br. s, 6H), 2.78 (br. s, 6H), 2.29-2.23 (m, 12H), 2.23-2.17 (m, 36H), 2.15-2.09 (m, 12H), 2.00-1.90 (m, 36H), 1.44 (s, 162H), 1.24-1.14 (m, 18H). $^{13}$C NMR (101 MHz, Methanol-$d_4$) δ 175.6, 175.5, 174.4, 169.7, 169.4, 169.3, 158.4, 158.3, 157.3, 157.2, 144.5, 144.5, 144.4, 137.1, 136.7, 134.3, 134.3, 134.0, 133.8, 131.2, 131.2, 130.5, 130.2, 129.4, 126.1, 125.9, 125.4, 125.2, 122.7, 122.2, 81.6, 71.5, 71.4, 71.1, 70.6, 59.5, 59.4, 58.8, 58.7, 51.7, 40.9, 38.9, 38.8, 38.7, 38.7, 32.4, 32.2, 30.7, 30.7, 30.4, 28.4, 23.6, 16.8, 16.7, 16.6. HRMS [M+3H]$^{3+}$ calculated for $C_{215}H_{345}N_{24}O_{53}$ requires: 1371.1700, found: 1371.1720.

Step 5: Preparation of Compound 22
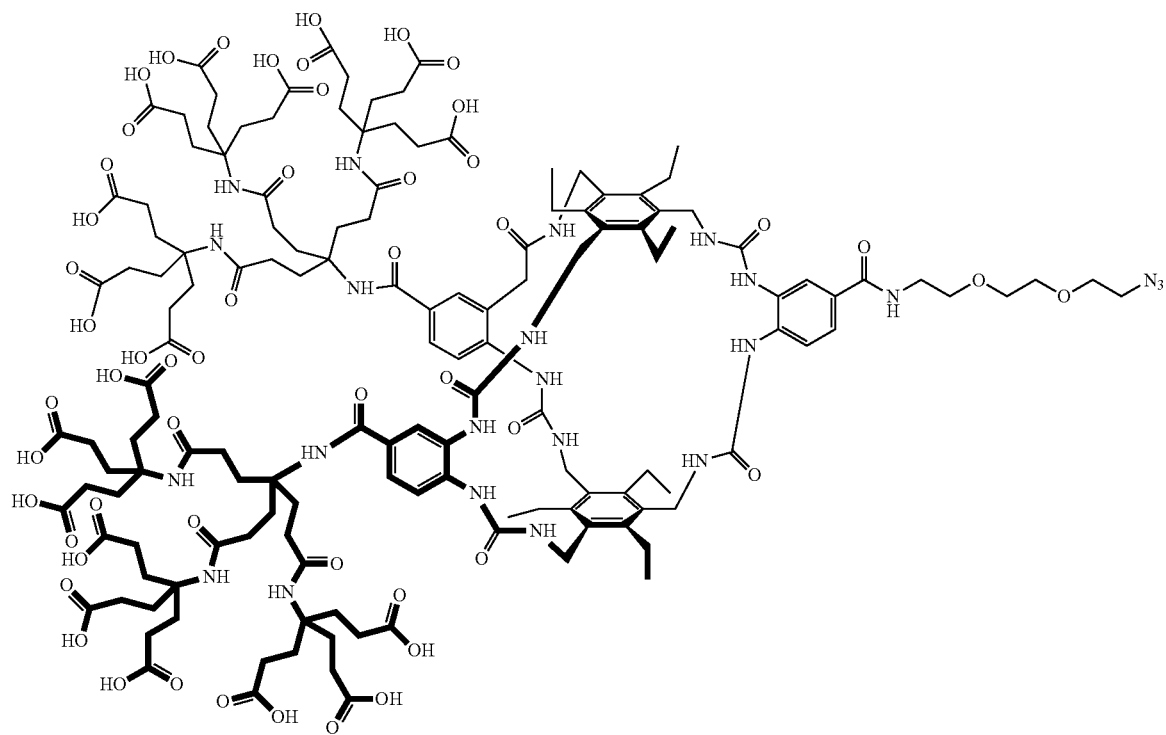
Made from compound 22d (500 mg, 0.122 mmol) as per compound 6d. The product isolated as a yellow amorphous solid compound 22 (376 mg, 0.122 mmol, 99%). $^1$H NMR (400 MHz, deuterated phosphate buffer in $D_2O$) δ 8.01-7.67 (m, 6H), 7.67-7.49 (m, 2H), 7.43 (s, 1H), 4.55-4.21 (m, 12H), 3.92-3.47 (m, 8H), 3.47-3.29 (m, 2H), 2.82-2.55 (m, 12H), 2.43-2.18 (m, 12H), 2.18-2.00 (m, 48H), 2.00-1.72 (m, 36H), 1.36-0.80 (m, 18H).
Preparation of Compound 23 G2 Macrocycle PEG5 Azide
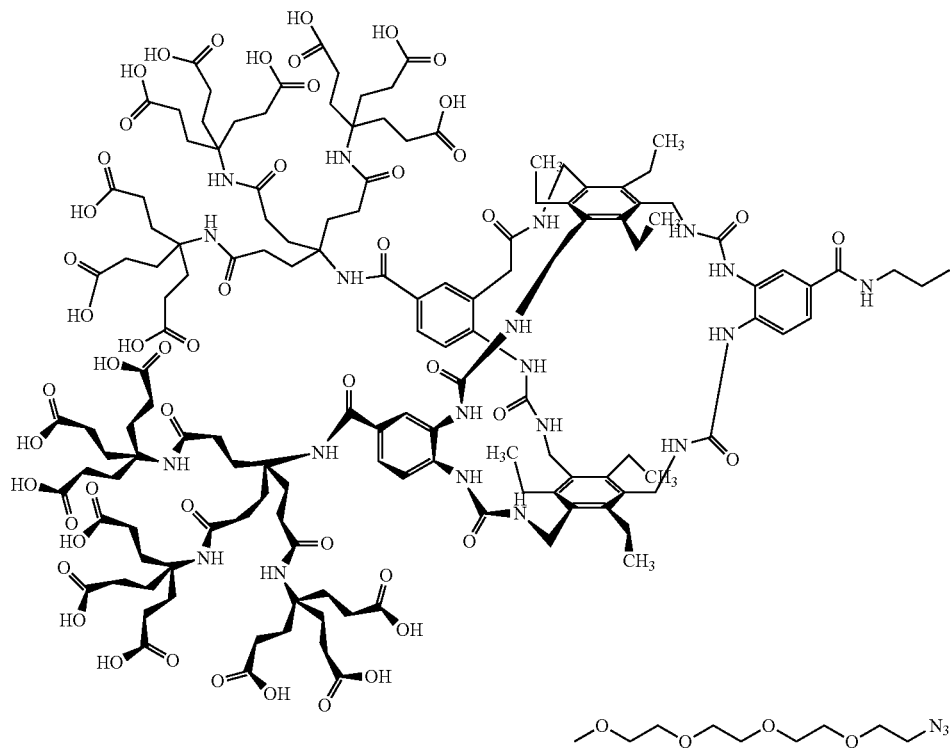

Step 1: Preparation of Compound 23a

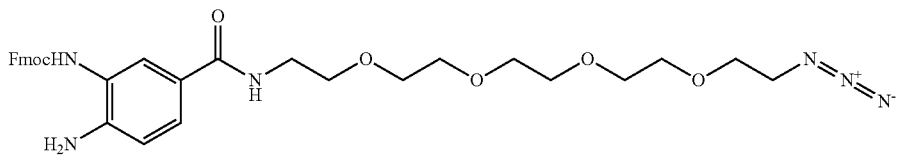

Made from compound 1 (3.975 g, 6.470 mmol) and 14-azido-3,6,9,12-tetraoxatetradecan-1-amine (2.546 g, 9.705 mmol) as per compound 3a. Isolated as a brown oil (3.933 g, 6.357 mmol, 98%). $^1$H NMR (400 MHz, CDCl$_3$) δ 7.75 (d, J=7.6 Hz, 2H, ArH), 7.67-7.55 (m, 2H, ArH), 7.50 (d, J=13.6 Hz, 1H, ArH), 7.39 (t, J=7.5 Hz, 2H, ArH), 7.34-7.27 (m, 2H, ArH), 7.15 (m, 1H, ArH), 6.89 (m, 1H, ArH), 6.69 (d, J=8.4 Hz, 1H, C(O)NHCH2), 4.52 (s, 1H, Flu-CH), 4.24 (s, 2H, Flu-OCH2), 3.70-3.46 (m, 16H, OCH2), 3.28 (t, J=5.1 Hz, 2H, (C(O)NHCH2), 1.37 (dd, J=11.8, 7.0 Hz, 2H, N3CH2). $^{13}$C NMR (101 MHz, CDCl$_3$) δ 167.26 (C(O)NH), 143.80, 141.45, 127.89, 127.26, 125.14, 120.10 (Ar), 77.36, 70.57, 70.49, 70.46, 70.43, 70.42, 70.22, 70.03, 69.92 (OCH2), 55.66 (Flu-OCH2), 50.66 (Flu-CH), 39.80 (N3CH2), 38.72 (NHCH2).

Step 2: Preparation of Compound 23b

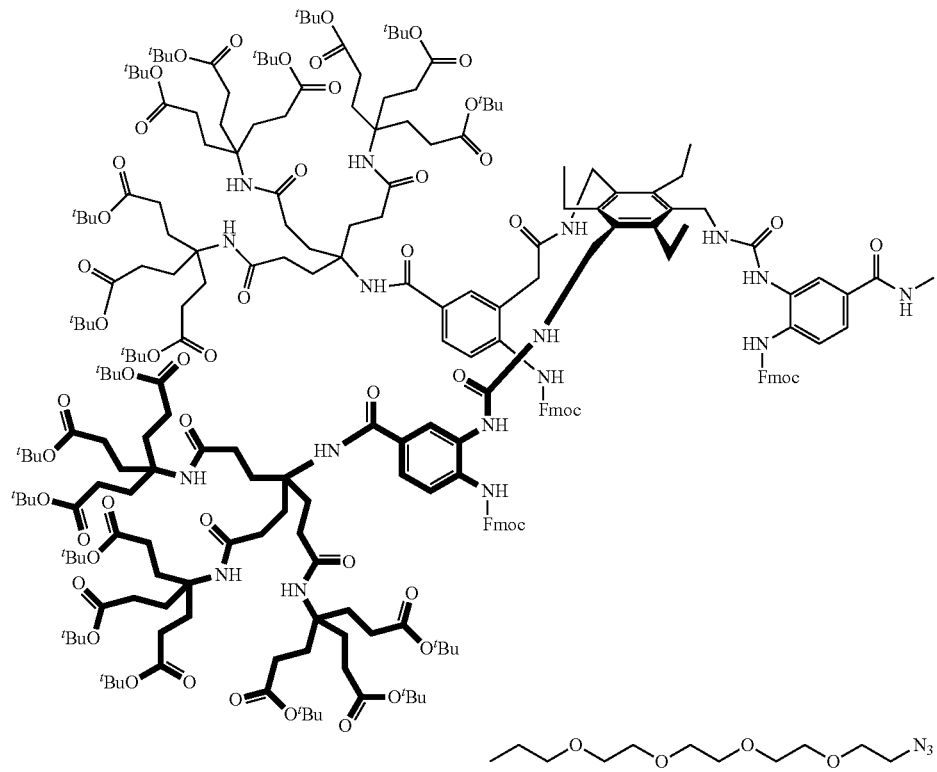

Made from compound 4a (3.24 g, 1.80 mmol), 23a (836 mg, 1.35 mmol) and 2b (295 mg, 0.90 mmol) as per compound 6a. The product isolated as an off-white amorphous solid 23b (1.77 g, 0.387 mmol, 43%). $^1$H NMR (400 MHz, Methanol-d$_4$) δ 8.02-7.48 (m, 18H), 7.46-7.11 (m, 15H), 4.46 (br. s, 6H), 4.34 (br. s, 6H), 4.15 (br. s, 3H), 3.54-3.44 (m, 18H), 3.25 (dd, J=5.6, 4.4, 2H), 2.80 (br. s, 6H), 2.35-2.04 (m, 60H), 2.04-1.80 (m, 36H), 1.41 (s, 162H), 1.25-1.11 (m, 9H).

Step 3: Preparation of Compound 23c
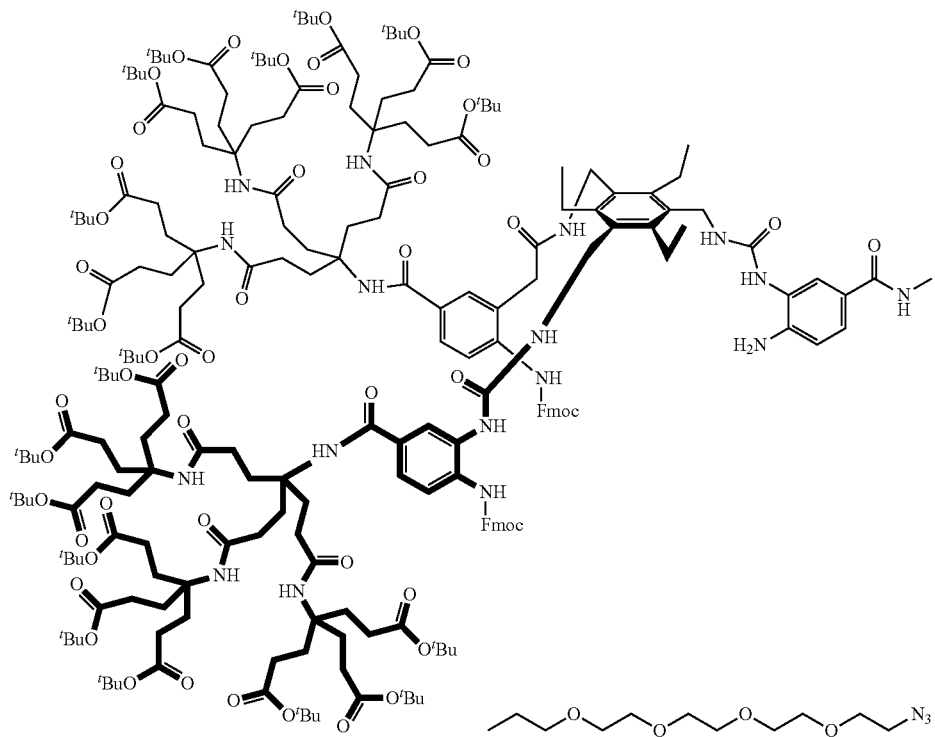
Made from compound 23b (1.76 g, 0.38 mmol) as per compound 6b. The product isolated as an off-white amorphous solid 23c (1.14 g, 0.29, 76%). $^1$H NMR (400 MHz, Methanol-$d_4$) δ 7.46-7.37 (m, 3H), 7.29 (d, J=2.1, 2H), 7.27 (d, J=2.0, 1H), 7.21 (dd, J=8.3, 2.1, 2H), 7.15 (dd, J=8.4, 2.0, 1H), 4.51 (s, 6H), 3.66-3.51 (m, 16H), 3.36-3.34 (m, 4H), 2.94-2.82 (m, 6H), 2.29-2.14 (m, 48H), 2.13-2.06 (m, 12H), 1.99-1.89 (m, 36H), 1.44 (s, 162H), 1.30-1.21 (m, 9H).
Step 4: Preparation of Compound 23d
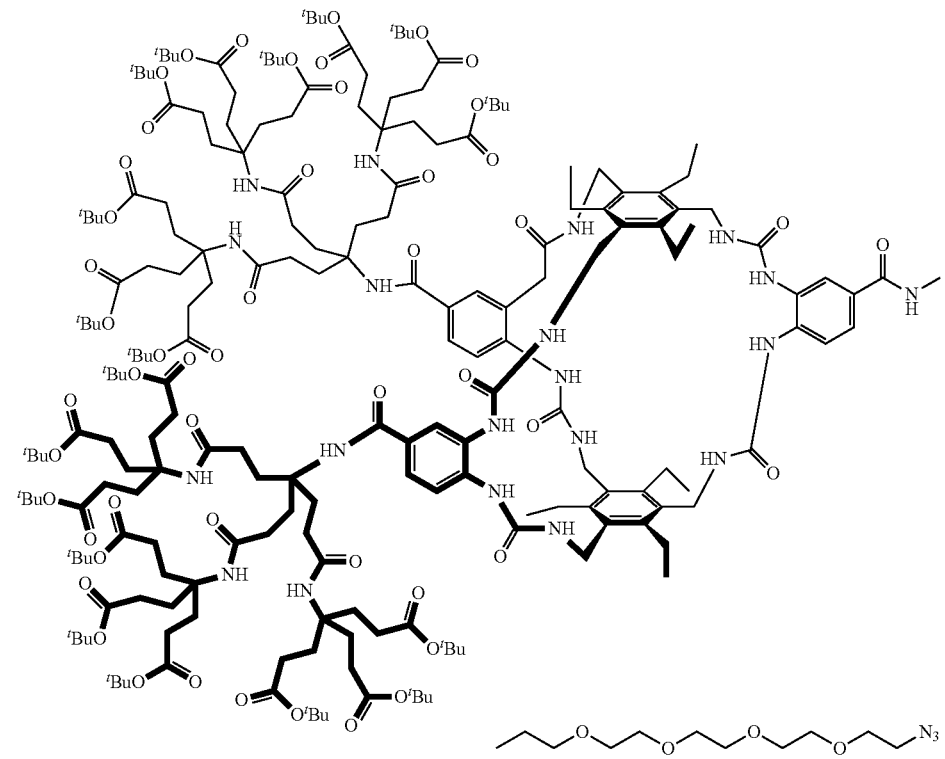

Made from compound 23c (500 mg, 0.27 mmol) and 2b (100 mg, 0.30 mmol) as per compound 6c, with the addition of 20% DMF to the solvent, only heated to 45° C. The product isolated as a white amorphous solid 23d (0.86 g, 0.19 mmol, 70%). $^1$H NMR (400 MHz, Methanol-$d_4$) δ 8.11-7.87 (m, 6H), 7.66 (d, J=8.5, 2H), 7.59 (d, J=8.4, 1H), 7.45 (s, 6H, NH signals slowly exchange so integration varies), 4.56-4.34 (m, 12H), 3.64-3.56 (m, 16H), 3.52-3.46 (m, 2H), 3.35-3.32 (m, 2H), 2.90 (br. s, 6H), 2.78 (br. s, 6H), 2.29-2.17 (m, 48H), 2.15-2.08 (m, 12H), 1.99-1.91 (m, 36H), 1.43 (s, 162H), 1.24-1.17 (m, 18H).

HRMS $[M+3H]^{3+}$ calculated for $C_{219}H_{350}N_{24}O_{55}$ requires: 1400.5209, found: 1400.5232.

Step 5: Preparation of Compound 23

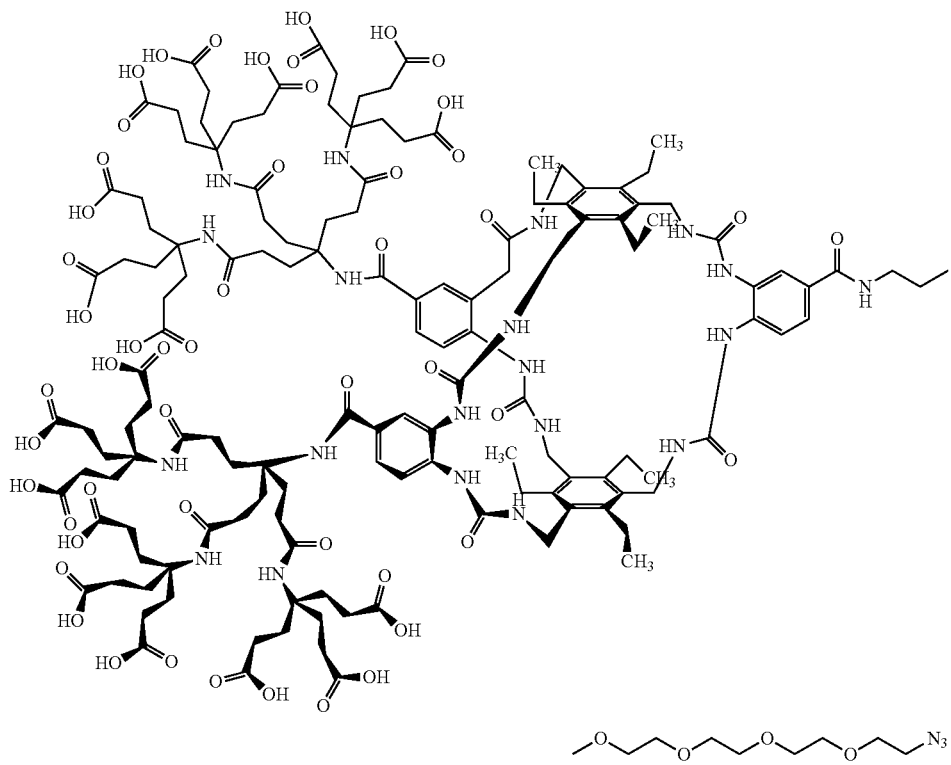

Made from compound 23d (750 mg, 0.179 mmol) as per compound 6d. The product isolated as a white amorphous solid 23 (570 mg, 0.179 mmol, 99%). $^1$H NMR (400 MHz, deuterated phosphate buffer in D20) δ 8.08-7.73 (m, 6H), 7.55 (d, J=8.6, 2H), 7.50-7.43 (m, 1H), 4.59-4.19 (m, 12H), 3.75-3.42 (m, 16H), 3.36-3.21 (m, 2H), 3.17-3.05 (m, 2H), 2.82-2.53 (m, 12H), 2.35-2.21 (m, 12H), 2.15-2.00 (m, 48H), 1.98-1.76 (m, 36H), 1.30-0.90 (m, 18H).

Preparation of Compound 24, G1 Macrocycle PEG5 Azide

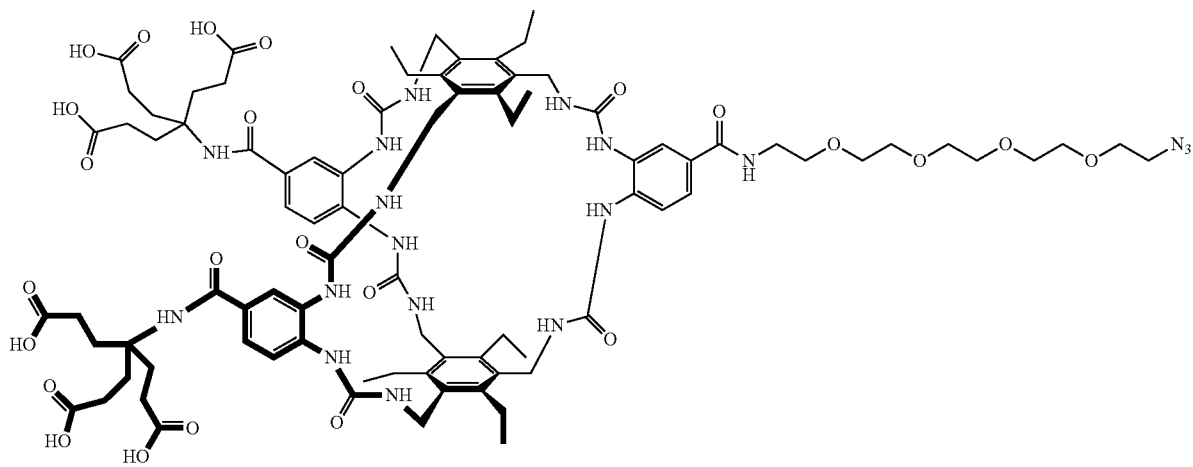

Step 1: Preparation of Compound 24a

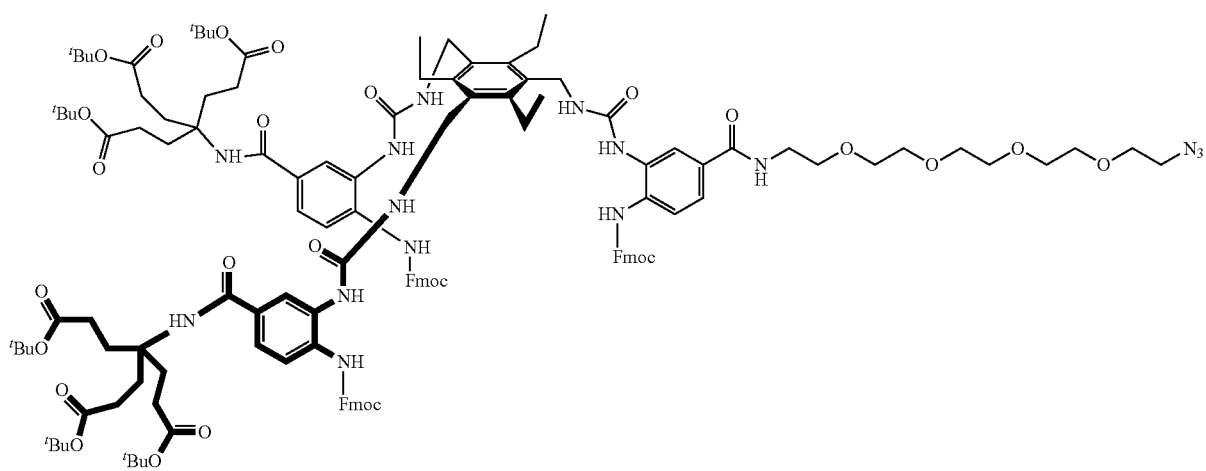

Made from compound 23a (2.36 g, 3.06 mmol), G1 dendrimer amine=di-tert-butyl-4-amino-4-(3-(tert-butoxy)-3-oxopropyl)heptanedioate, Frontier Scientific—NTN1963 (1.42 g, 2.29 mmol) and 2b (500 mg, 1.53 mmol) as per compound 6a. The product was isolated as an off-white amorphous solid (1.58 g, 0.64 mmol, 42%). $^1$H NMR (400 MHz, Methanol-$d_4$) δ 8.01-7.40 (m, 21H), 7.30 (t, J=7.5, 7H), 7.26-7.1 (m, 7H), 4.56-4.24 (m, 12H), 4.19-4.02 (m, 3H), 3.67-3.39 (m, 18H), 3.29-3.20 (m, 2H), 2.80 (d, J=9.0, 6H), 2.24 (dd, J=9.4, 6.4, 12H), 2.13-1.97 (m, 12H), 1.40 (s, 54H), 1.15 (t, J=7.3, 9H).

Step 2: Preparation of Compound 24b

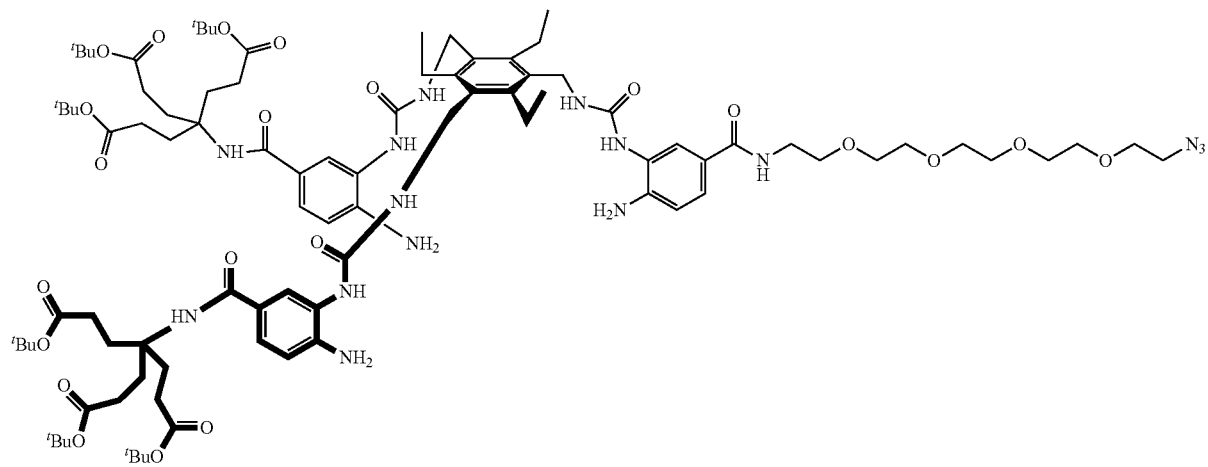

Made from compound 24a (1.55 g, 0.62 mmol) as per compound 6b. The product was isolated as an off-white amorphous solid 24b (1.11 g, 0.61, 98%). $^1$H NMR (400 MHz, Methanol-$d_4$) δ 7.39 (s, 1H (partly exchanged NH)), 7.33 (d, J=8.3, 3H), 7.23 (d, J=2.0, 1H), 7.18 (d, J=2.0, 2H), 7.07 (ddd, J=8.1, 4.1, 1.9, 3H), 4.49 (s, 6H), 3.70-3.54 (m, 16H), 3.51 (d, J=5.5, 2H), 3.35-3.25 (m, 2H), 2.99-2.72 (m, 6H), 2.39-2.16 (m, 12H), 2.08 (dd, J=9.5, 6.1, 12H), 1.44 (s, 54H), 1.24 (t, J=7.3, 9H).

Step 3: Preparation of Compound 24b

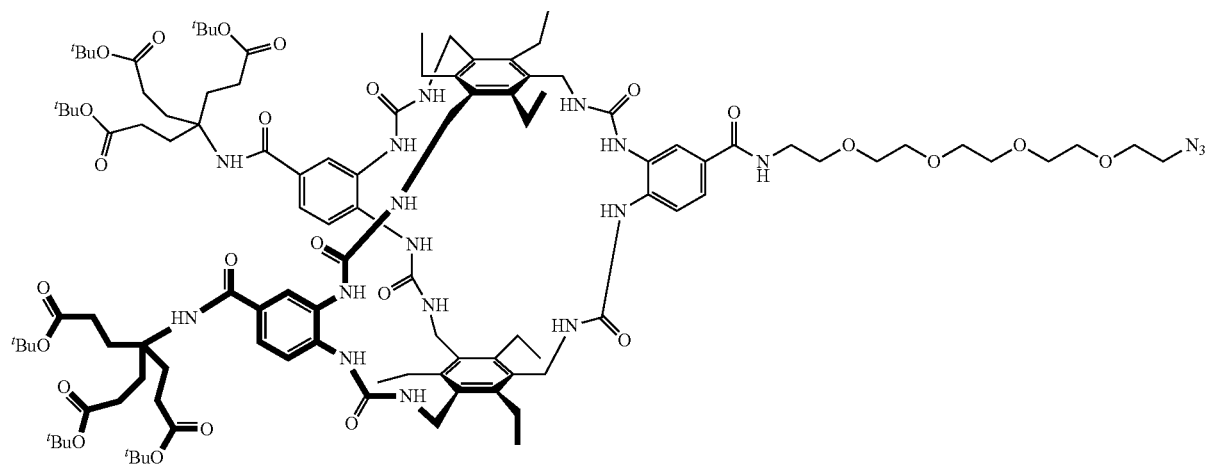

Made from compound 24a (500 mg, 0.27 mmol) and 2b (100 mg, 0.30 mmol) as per compound 6c, with the addition of 20% DMF to the solvent, heated to 45° C. The product isolated as a white amorphous solid 24b (0.33 g, 0.153 mmol, 58%). $^1$H NMR (400 MHz, Methanol-$d_4$) δ 8.03-7.94 (m, 3H), 7.94-7.87 (m, 3H), 7.62 (s, 1H), 7.56 (dd, J=8.7, 2.1, 3H), 4.48 (s, 4H), 4.43 (s, 8H), 3.60-3.33 (m, 18H), 3.30-3.28 (m, 2H), 2.96-2.83 (m, 6H), 2.77 (d, J=7.8, 6H), 2.32-2.23 (m, 12H), 2.10 (td, J=7.5, 4.7, 12H), 1.45 (s, 54H), 1.25-1.14 (m, 18H). HRMS [m+H]$^+$ calculated for $C_{111}H_{164}N_{18}O_{25}$ requires: 2151.5, found: 2151.5.

Step 4: Preparation of Compound 24, G1 Macrocycle PEG5 Azide
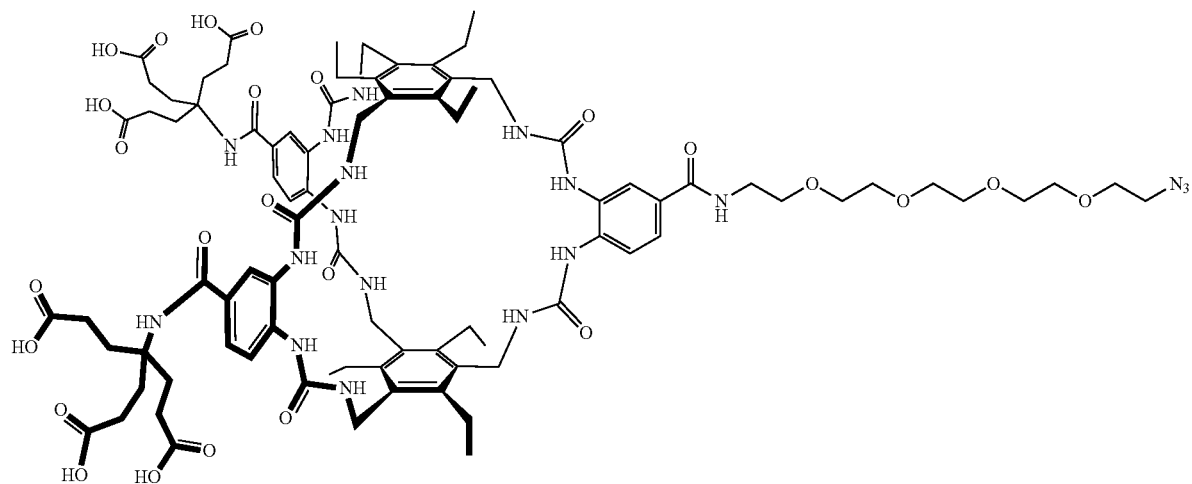
Made from compound 24b (330 mg, 0.153 mmol) as per compound 6d. The product isolated as a white amorphous solid 24 (281 mg, 0.153 mmol, 99%). $^1$H NMR (400 MHz, deuterated phosphate buffer in $D_2O$) δ 7.90-7.56 (m, 6H), 7.45-7.25 (m, 3H), 4.48-4.07 (m, 12H), 3.71-3.13 (m, 18H), 3.13-3.01 (m, 2H), 2.70-2.44 (m, 12H), 2.35-2.21 (m, 12H), 2.08-2.01 (m, 12H), 2.01-1.84 (m, 12H), 1.12-0.91 (m, 18H).
Preparation of Compound 25, G0 Macrocycle PEG4 Azide
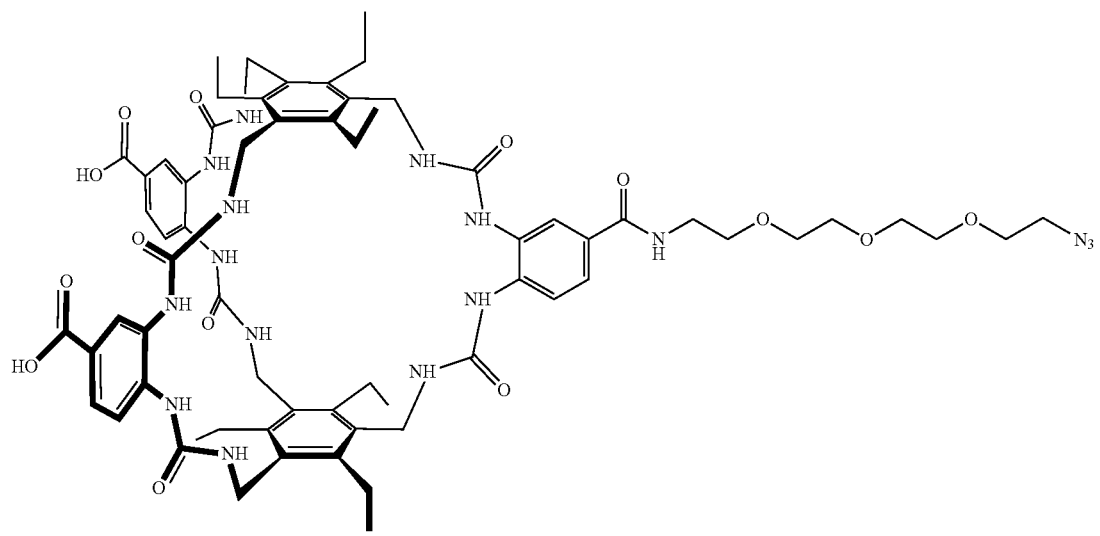

Step 1: Preparation of Compound 25a

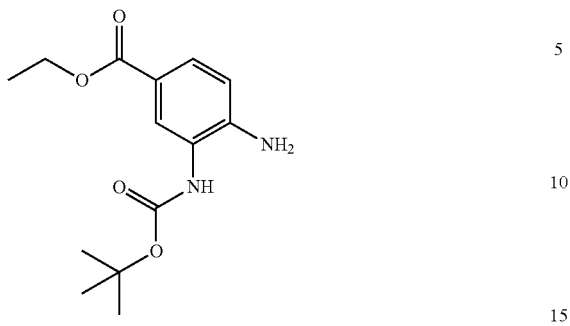

Ethyl 3,4-diaminobenzoate (25.0 g, 0.139 mol) was dissolved in THF (280 mL). Triethylamine (23.2 mL, 0.166 mol) and Boc$_2$O (33.3 g, 0.153 mol, 1.1 eq) were added. Stirred at room temperature for 16 h. The solvent was removed under vacuum and the crude solid triturated in hot diethyl ether/petrol 40-60 (5:95, 500 mL), filtered, washed with petrol 40-60 (100 mL) and dried under high vacuum to yield the product as a light brown solid (34.8 g, 89.5%).

$^1$H NMR (400 MHz, chloroform-d) δ 7.83 (d, J=1.9 Hz, 1H), 7.72 (dd, J=8.4, 2.0 Hz, 1H), 6.73 (d, J=8.4 Hz, 1H), 6.15 (s, 1H), 4.30 (q, J=7.1 Hz, 3H), 4.26 (s, 2H), 1.50 (s, 10H), 1.35 (t, J=7.2 Hz, 4H).

Step 2: Preparation of Compound 25b

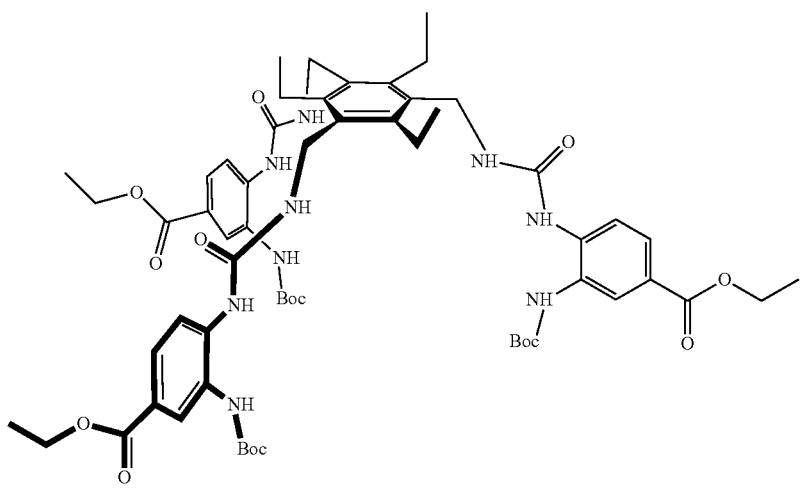

Under a N$_2$ atmosphere, 25a (17.0 g, 60 mmol) and 2b (3.3 g, 10 mmol) were dissolved in anhydrous DCM (100 mL) and anhydrous DMF (9.9 mL). Anhydrous pyridine (7.3 mL, 91 mmol, 9 eq) was added and the reaction stirred at 40° C. for 18 h. The reaction was cooled to room temperature and the solvent removed under vacuum. The crude oil was then precipitated with 1M aqueous HCl (1000 mL), filtered, washed with Et$_2$O and dried under high vacuum to yield the product 25b (11.7 g, 10 mmol, 99%) as a light brown solid.

$^1$H NMR (400 MHz, DMSO-d$_6$) δ 8.44 (s, 3H), 8.21 (d, J=8.7 Hz, 3H), 8.18 (s, 3H), 7.74 (s, 3H), 7.70 (dd, J=8.7, 2.1 Hz, 3H), 7.07 (t, J=3.7 Hz, 3H), 4.37 (br.s, 6H), 4.27 (q, J=7.1 Hz, 6H), 2.80 (q, J=7.5 Hz, 6H), 1.39 (s, 27H), 1.29 (t, J=7.1 Hz, 9H), 1.18 (t, J=7.3 Hz, 9H).

Step 3: Preparation of Compound 25c

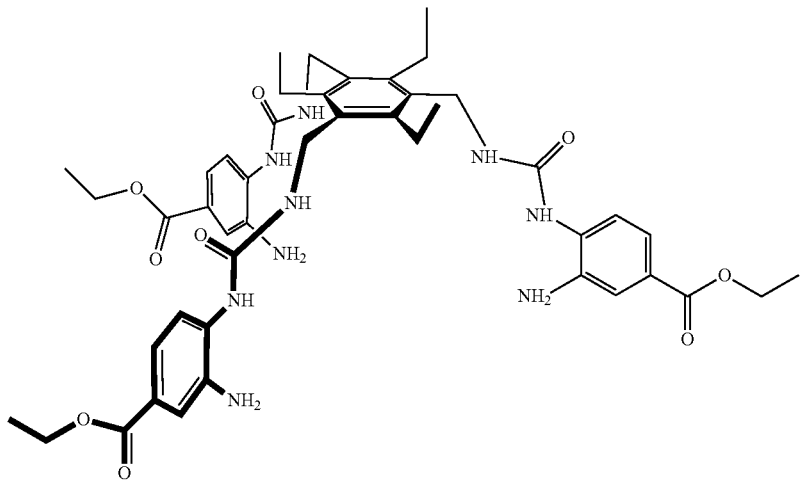

25b (11.1 g, 9.50 mmol) was dissolved in CH$_2$Cl$_2$ (62 mL) and DMF (15 mL). Trifluoroacetic acid (77.1 mL, 1.0 mol) was added over 5 minutes and the reaction stirred for 3 h at room temperature. The reaction mixture was concentrated under a flow of nitrogen and the crude oil precipitated with aqueous saturated Na$_2$CO$_3$ (1500 mL), filtered, washed with water. The crude solid was then washed with Et$_2$O and dried under high vacuum to afford the product 25c (8.0 g, 9.2 mmol, 97%) as an off white solid. $^1$H NMR (400 MHz, DMSO-d$_6$) δ 7.82-7.68 (m, 6H), 7.31 (d, J=2.0 Hz, 3H), 7.18 (dd, J=8.5, 2.0 Hz, 3H), 6.47 (s, 3H), 4.79 (s, 6H), 4.39-4.27 (m, 6H), 4.20 (q, J=7.1 Hz, 6H), 2.87-2.66 (m, 6H), 1.24 (t, J=7.1 Hz, 9H), 1.15 (t, J=7.4 Hz, 9H). MS [M+H]$^+$ calculated for C$_{45}$H$_{58}$N$_9$O$_9$$^+$ requires: 868.4, found: 868.4.

Step 4: Preparation of Compound 25d

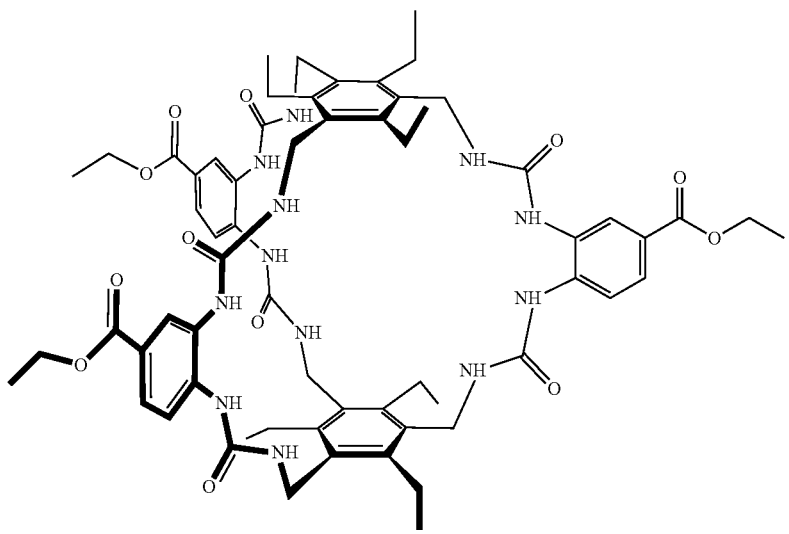

Under an N$_2$ atmosphere, 25c (5.00 g, 6 mmol, 1 eq) was dissolved in anhydrous DMF (417 mL) and anhydrous pyridine (960 mL) and heated to 45° C. 2b (2.26 g, 7 mmol, 1.2 eq) was then added as a solution in anhydrous CH$_2$Cl$_2$ (41 mL) over 10 h and the reaction mixture left to stir at 45° C. for a further 6 h. The reaction mixture was then concentrated under vacuum and the crude residue precipitated with 1M aqueous HCl (1000 mL), filtered, washed with water and dried. The crude solid was then dissolved in MeOH/CH$_2$Cl$_2$, dry loaded onto C18 and purified by reverse phase flash chromatography (45%-80% MeCN:water with 0.1% formic acid). Fractions containing the product were combined and concentrated under vacuum to yield the product (4.2 g, 4 mmol, 61%) as an off white solid. $^1$H NMR (400 MHz, DMSO-$d_6$) δ 8.22 (d, J=2.1 Hz, 3H), 8.08 (d, J=8.7 Hz, 3H), 7.89 (s, 3H), 7.60 (dd, J=8.6, 2.1 Hz, 3H), 7.53 (s, 3H), 6.49 (t, J=5.1 Hz, 3H), 6.35 (t, J=5.4 Hz, 3H), 4.36-4.24 (m, 18H), 2.80 (d, J=7.7 Hz, 6H), 2.67 (d, J=7.8 Hz, 6H), 1.31 (t, J=7.1 Hz, 9H), 1.19-1.10 (m, 18H). MS [M+H]$^+$ calculated for $C_{63}H_{79}N_{12}O_{12}^+$ requires: 1195.5, found: 1195.5.

$^1$H NMR (400 MHz, DMSO-$d_6$) δ 8.18 (d, J=2.1 Hz, 2H), 8.17 (d, J=2.1 Hz, 1H), 8.04 (d, J=8.7 Hz, 2H), 8.01 (d, J=8.6 Hz, 1H), 7.86 (s, 2H), 7.83 (s, 1H), 7.59-7.52 (m, 3H), 7.50 (s, 2H), 7.46 (s, 1H), 6.48-6.42 (m, 3H), 6.36-6.27 (m, 3H), 4.33-4.21 (m, 16H), 2.83-2.71 (m, 6H), 2.68-2.58 (m, 6H), 1.28 (t, J=7.1 Hz, 6H), 1.11 (td, J=7.3, 6.9, 2.4 Hz, 18H). MS [M+H]$^+$ calculated for $C_{59}H_{71}N_{12}O_{12}^+$ requires: 1139.5, found: 1139.5.

Step 6: Preparation of Compound 25f

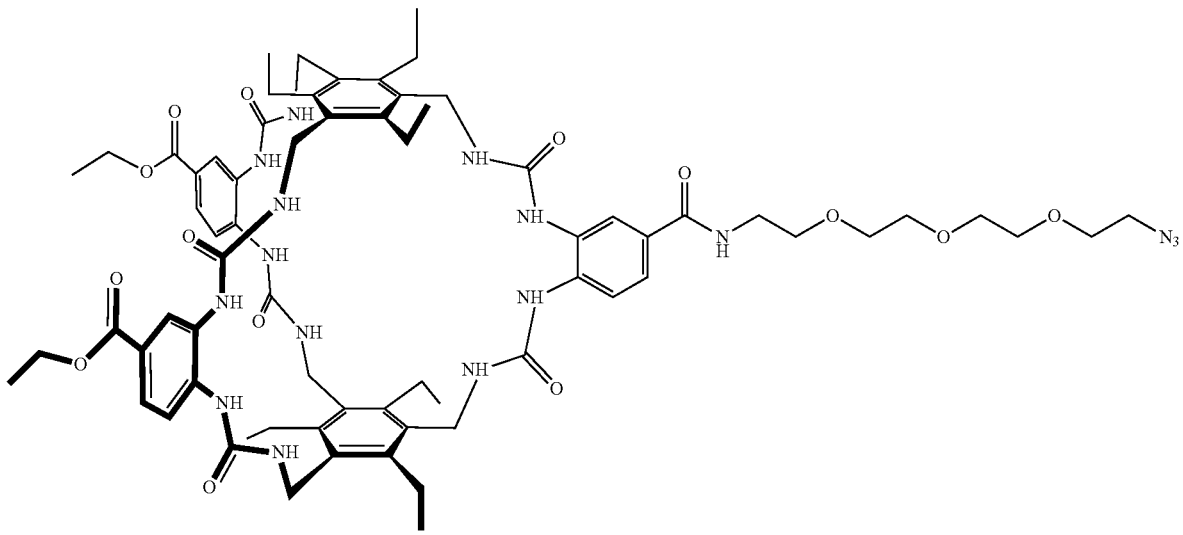

Step 5: Preparation of Compound 25e

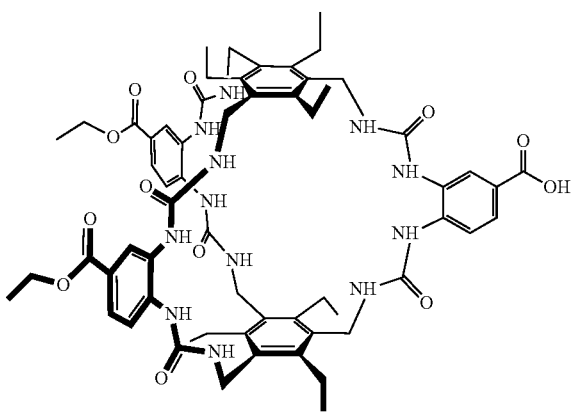

25d (4.9 g, 4.10 mmol, 1 eq) was suspended in ethanol (50 mL) and water (50 mL) and heated to 40° C. Sodium hydroxide (0.246 g, 6.15 mmol, 1.5 eq) was added and the reaction stirred at 40° C. for 16 hours. The reaction was cooled to room temperature and the organic solvent removed under vacuum. The crude product was then precipitated with 1M aqueous HCl (400 mL), filtered, washed with 1M aqueous HCl and dried. The crude solid was then dissolved in acetone/water, dry loaded onto C18 and purified by reverse phase flash chromatography. The fractions containing the product were combined and the solvent removed under vacuum to yield the product 25e (1.7 g, 1.46 mmol, 36%) as a white solid.

Under an N$_2$ atmosphere, 25e (300 mg, 0.231 mmol, 1.0 eq), HBTU (97 mg, 0.254 mmol, 1.1 eq) and HOBt.H$_2$O (39 mg, 0.254 mmol, 1.1 eq) were dissolved in anhydrous DMF (8.5 mL). DIPEA (80 µL, 0.460 mmol, 2 eq) was added and the reaction mixture stirred at room temperature for 15 minutes. 11-Azido-3,6,9-trioxanundecan-1-amine (100 µL, 0.463 mmol, 2 eq) was added and the reaction stirred at room temperature for 16 h. The reaction mixture was poured into water, the precipitate filtered, washed with water and transferred to an RBF with acetone. The solvent was removed under vacuum and the crude residue loaded onto a 30 g SNAP Ultra C18 cartridge in acetone/water and purified by reverse phase flash chromatography (50 to 100% acetone: water gradient). The product containing fractions were combined and the solvent removed under vacuum to give a white solid that was further dried under vacuum to yield the product 25f (240 mg, 0.175 mmol, 76%) as a white solid. $^1$H NMR (400 MHz, Methanol-$d_4$) δ 8.23 (d, J=2.0 Hz, 2H), 8.04 (d, J=2.1 Hz, 1H), 8.01 (d, J=8.6 Hz, 2H), 7.94 (d, J=8.6 Hz, 1H), 7.79 (dd, J=8.7, 2.0 Hz, 2H), 7.60 (dd, J=8.6, 2.1 Hz, 1H), 4.49-4.40 (m, 12H), 4.35 (q, J=7.1 Hz, 4H), 3.67-3.58 (m, 12H), 3.52 (t, J=5.4 Hz, 2H), 2.91-2.71 (m, 12H), 1.39 (t, J=7.1 Hz, 6H), 1.20 (t, J=7.6 Hz, 18H).

Step 7: Preparation of Compound 25, G0 Macrocycle PEG4 Azide

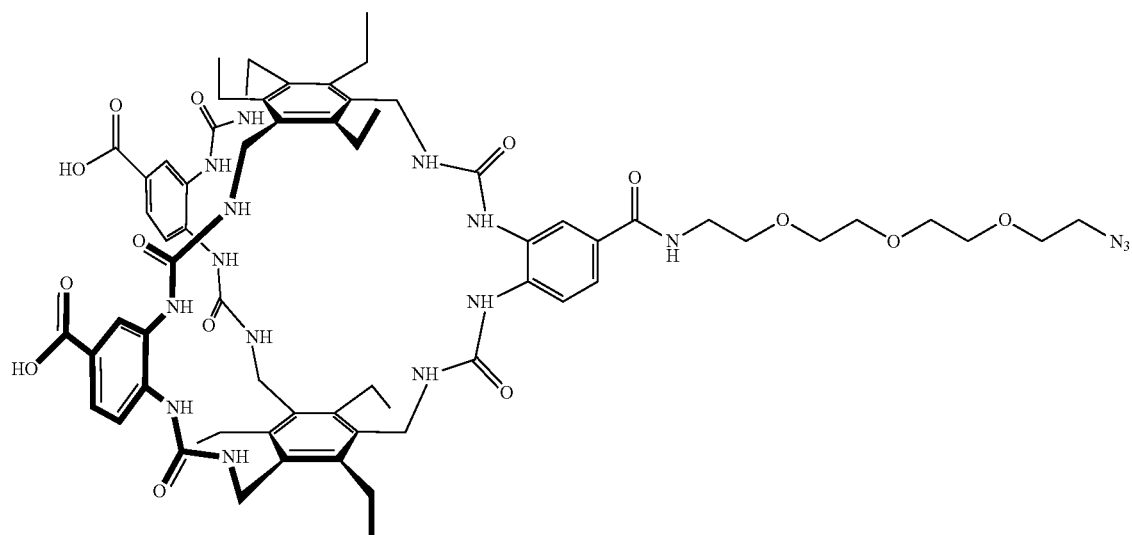

Dissolved 25f (0.22 g, 0.161 mmol, 1.0 eq) in ethanol (5 mL) and methanol (0.5 mL). Added 1M aqueous sodium hydroxide (5.5 mL) and stirred at 40° C. for 3 h. Removed organic solvent under vacuum to give aqueous solution, which was then poured in 1M aqueous hydrochloric acid. The resultant suspension was centrifuged, the water decanted and solid washed with water. The solid was then centrifuged again, the water decanted and solid transferred to an RBF with acetone. The solvent was removed under vacuum and dried under high vacuum to yield 25 (190 mg, 0.111 mmol, 90%) as a white solid. $^1$H NMR (400 MHz, DMSO-$d_6$) δ 8.41 (s, 2H), 8.37 (d, J=2.0 Hz, 2H), 8.31-8.23 (m, 2H), 8.21 (d, J=2.1 Hz, 1H), 8.13 (s, 2H), 8.11 (d, J=8.6 Hz, 2H), 8.01 (d, J=8.7 Hz, 2H), 7.52 (dd, J=8.6, 2.1 Hz, 2H), 7.43 (dd, J=8.6, 2.1 Hz, 1H), 6.58-6.42 (m, 3H), 6.29 (d, J=5.4 Hz, 3H), 4.32 (s, 12H), 3.60-3.49 (m, 11H), 2.81-2.54 (m, 12H), 1.16 (dd, J=9.2, 4.3 Hz, 18H). MS [M+H]$^+$ calculated for $C_{65}H_{83}N_{16}O_{14}^+$ requires: 1311.6, found: 1311.6.

Preparation of Insulin Derivatives of the Invention

Example 1: Preparation of B1-Benzyl-4-Triazolyl-PEG4-G2macrocycle B29-PEG3-Glycoside desB30 Human Insulin INS1

INS1

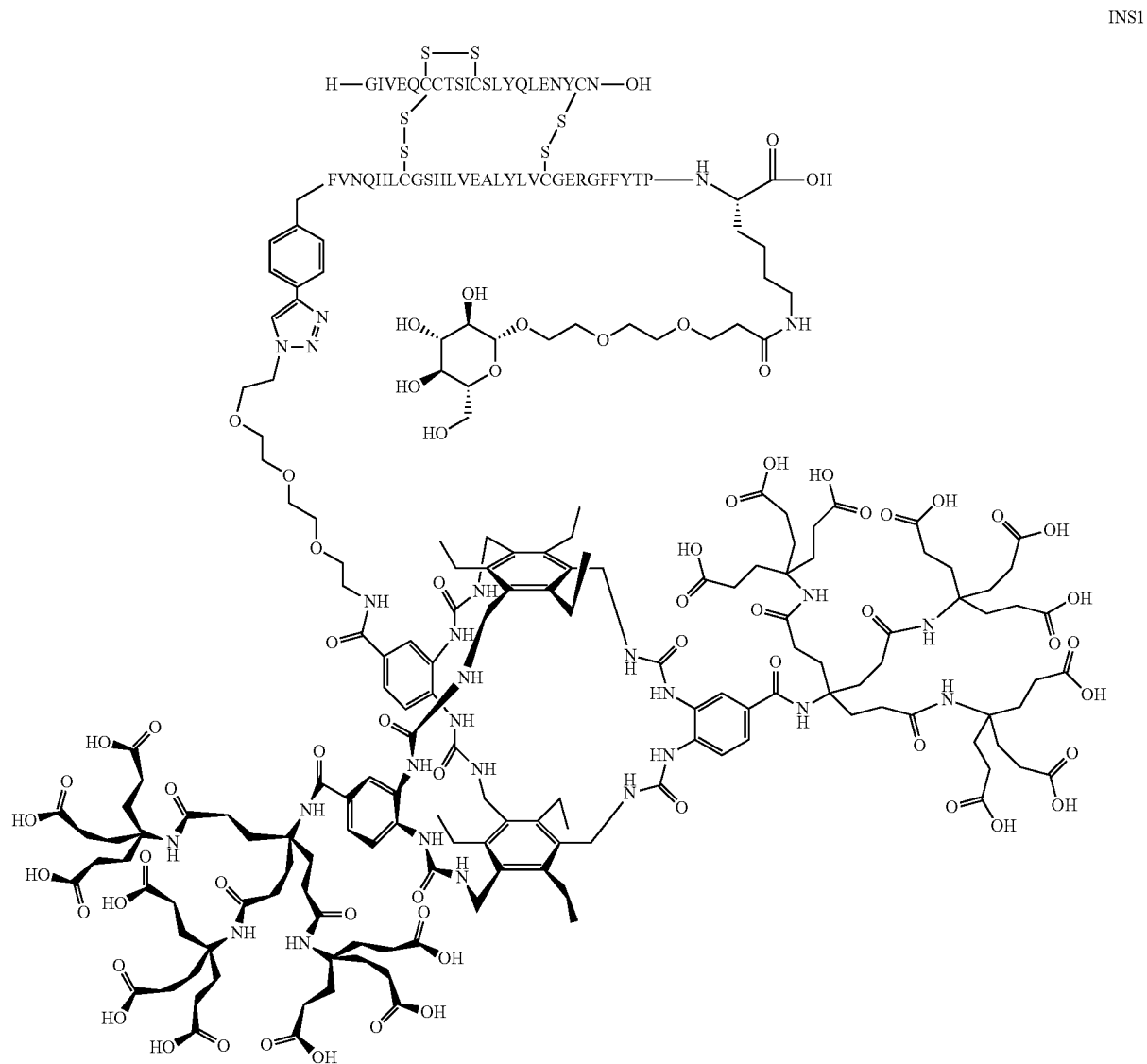

The insulin derivative INS1 of example 1 is prepared as described below.

Step 1: Preparation of B1-4-Ethynyl-Benzyl desB30 Human Insulin INS2 (Scheme 1)

Scheme 1

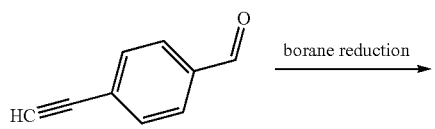

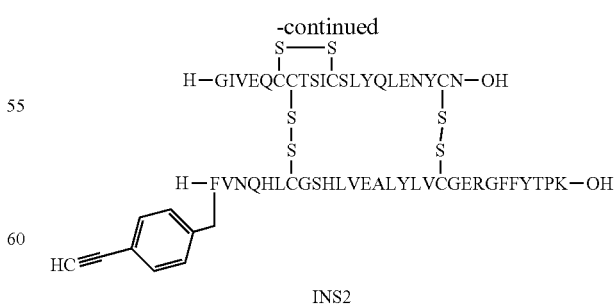

INS2

DesB30 human insulin is dissolved in 0.1 M acetic acid, and pH is adjusted to 4 using 8 M acetic acid. 4-ethynyl-benzaldehyde (1.5 equivalent) in N-methyl-pyrrolidone (NMP) is added, and the mixture is stirred 30 minutes. Alpha-picoline borane (6 equivalents) in NMP is added and the mixture is stirred 2 hours, while pH is kept near 4 by additions of 8 M acetic acid. LCMS shows formation of the desired product. pH is adjusted to 2, and the product is purified by reverse-phase HPLC (RP-HPLC) on C18 column using 0.1% TFA in water as buffer A and 0.1% TFA in acetonitrile as buffer B. The product (INS2 (Scheme 1)) is isolated by lyophilisation.

Step 2: Preparation of INS3 (Scheme 2)

Scheme 2

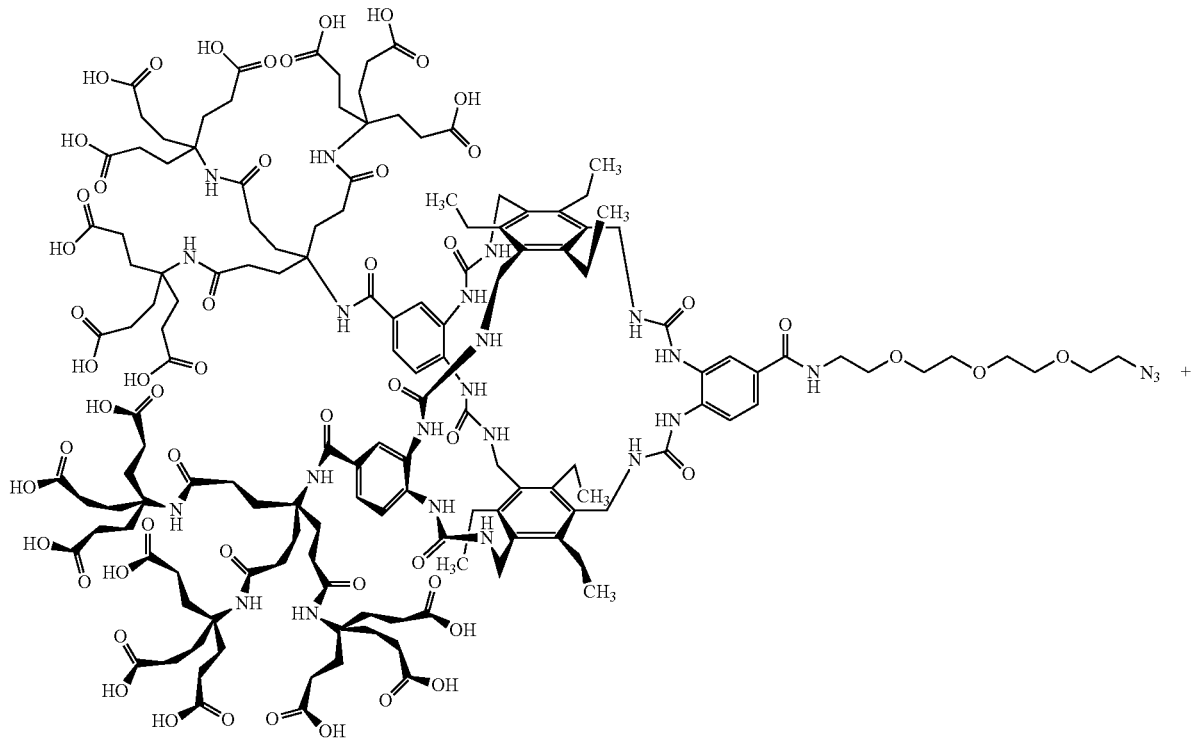

6d

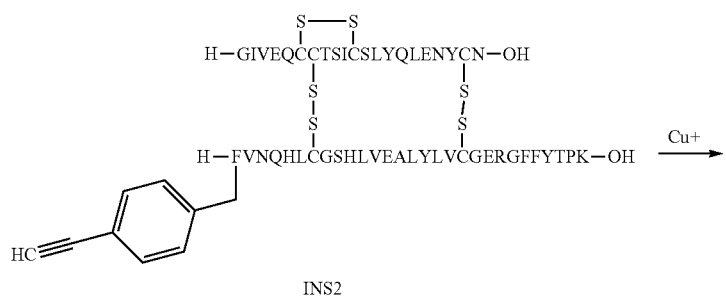

INS2

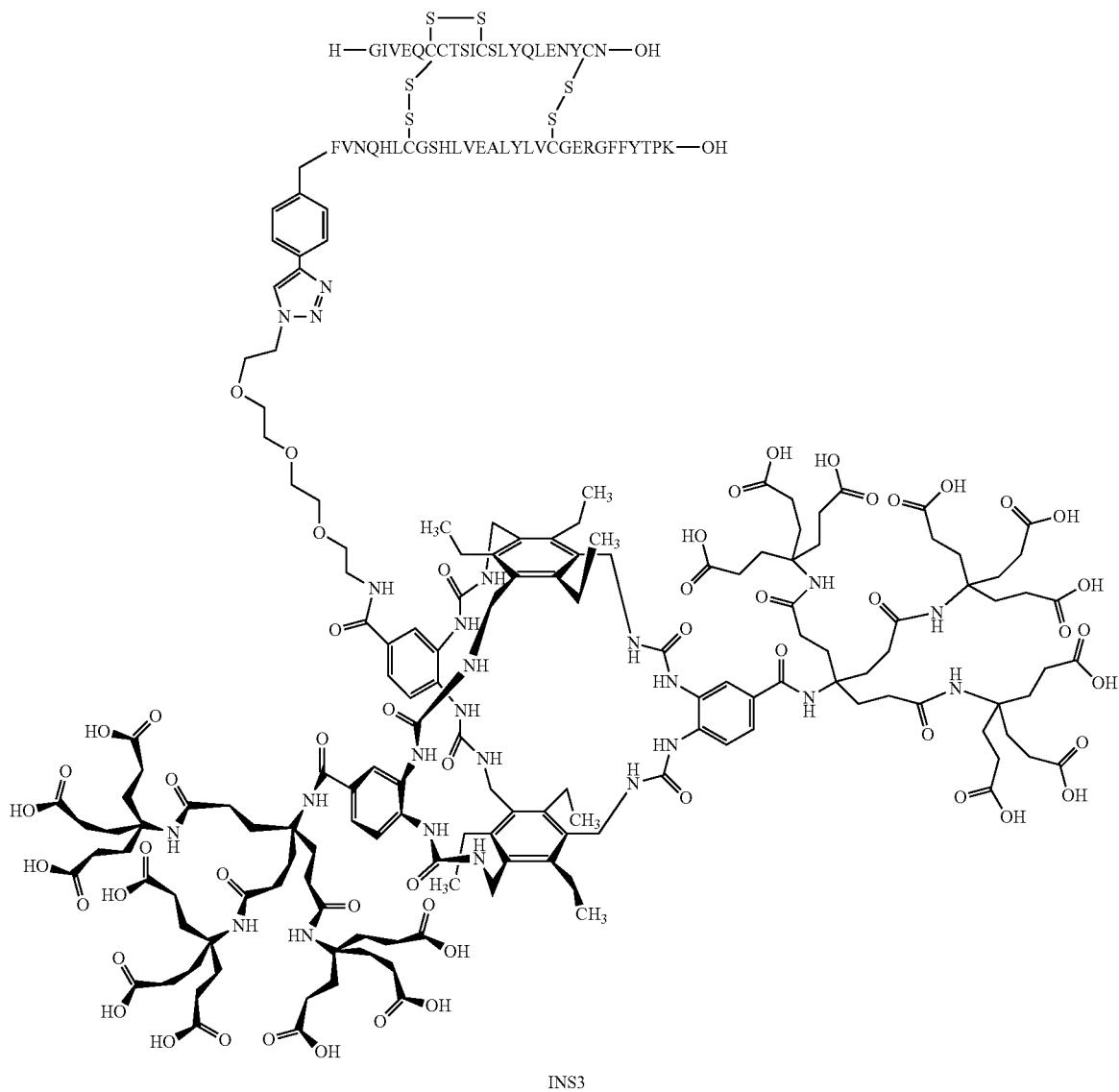

INS3

Macrocycle-PEG-azide 6d as prepared above is dissolved in N,N-dimethylformamide (DMF) and reacted under inert atmosphere (nitrogen) with alkyne insulin INS2 (chem. 1, 1 equivalent) dissolved in 2 M triethylamine adjusted to pH 7.8 using acetic acid, with CuI as catalyst (0.1 equivalent) and tris(3-hydroxypropyltriazolylmethyl)amine (THPTA, 2 equivalents) as ligand. The reaction is followed by LCMS, and the product INS3 (Scheme 2) is isolated using RP-HPLC as described Example 1, Step 1.

Step 3: Preparation of Compound INS1
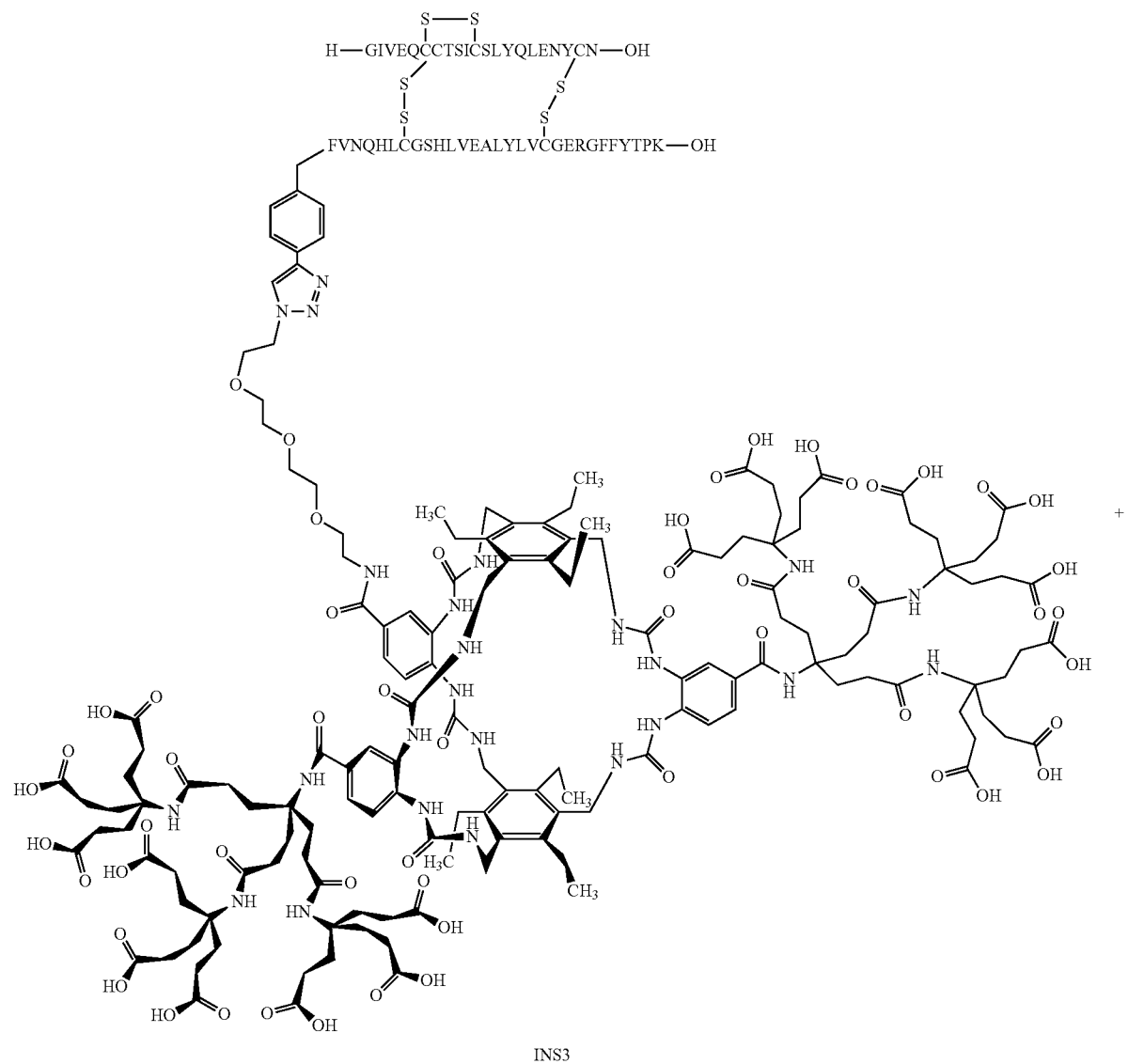
Scheme 3
INS3
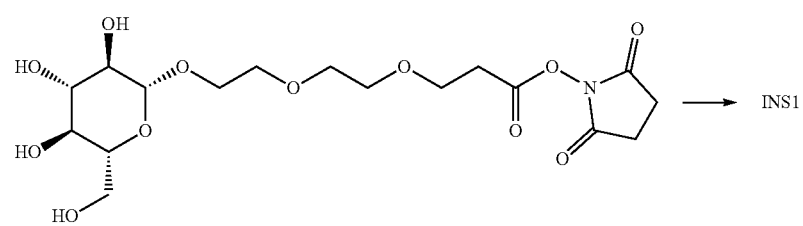
→ INS1

The active ester 8 (1.2 equivalents) is reacted with B1-macrocycle-insulin INS3 (Scheme 2) dissolved in 0.2 M sodium carbonate at pH 10.5. The reaction is followed by LCMS, and the B1-macrocycle B29-glycoside INS1 of example 1 is isolated using RP-HPLC as described in Example 1, Step 1. LCMS measured 1858.5 [M+5H]5+, calculated 1858.6.

Example 2: Preparation of
B1-benzyl-4-triazolyl-PEG4-G2macrocycle
A1-PEG3-glycoside desB30 human insulin INS4

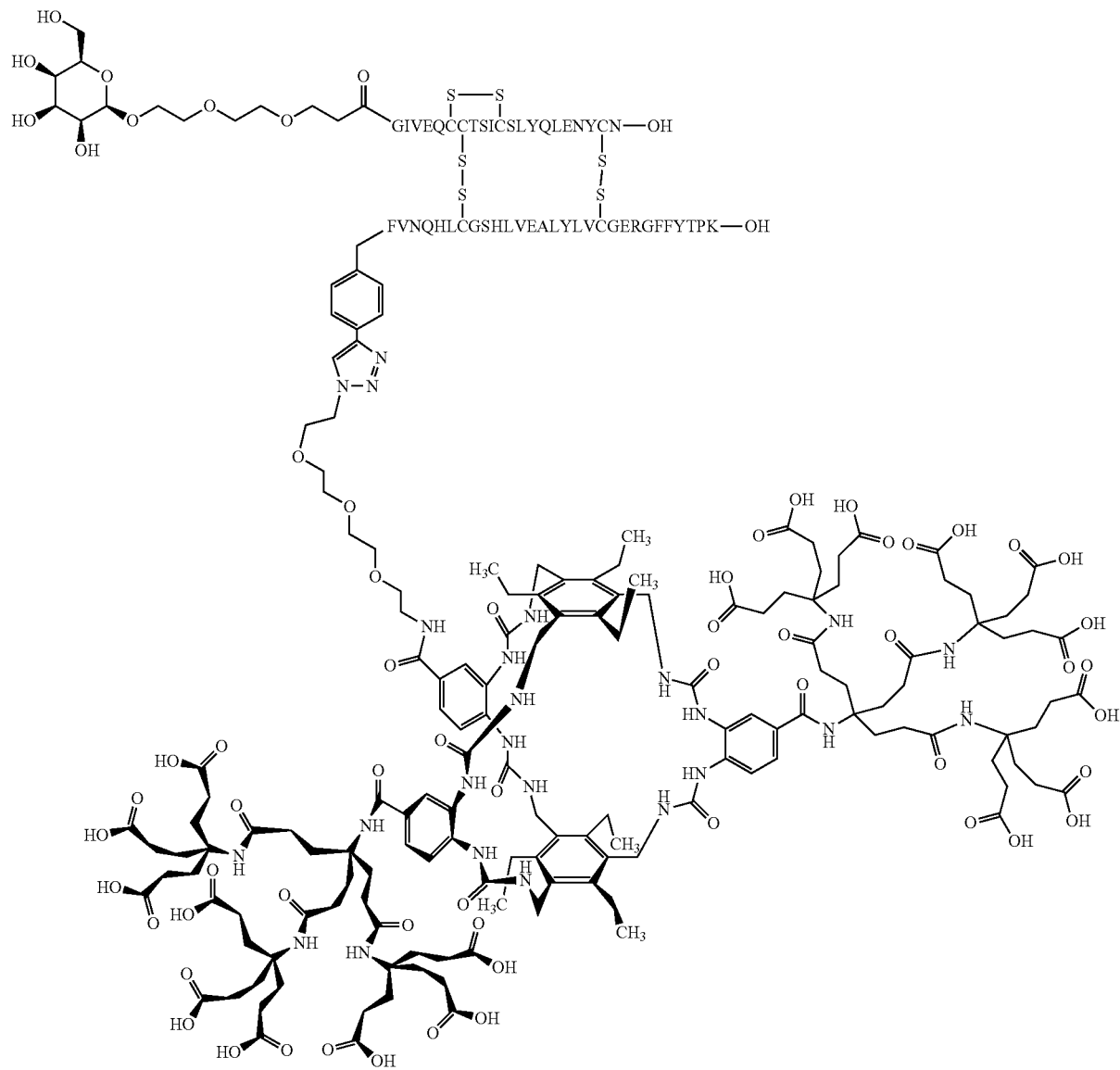

INS4

B1-macrocycle-insulin INS3 (Scheme 2, prepared as in Example 1, Step 2) in 0.1 M sodium bicarbonate at pH 7.5 is reacted with glucoside active ester 8. The reaction is followed by LCMS, and the B1-macrocycle A1-glucoside INS4 of example 2 is isolated using RP-HPLC as described in Example 1, Step 1.

Example 3: Preparation of
B29-PEG4-G2macrocycle A1-PEG3-Glycoside
desB30 Human Insulin INS5

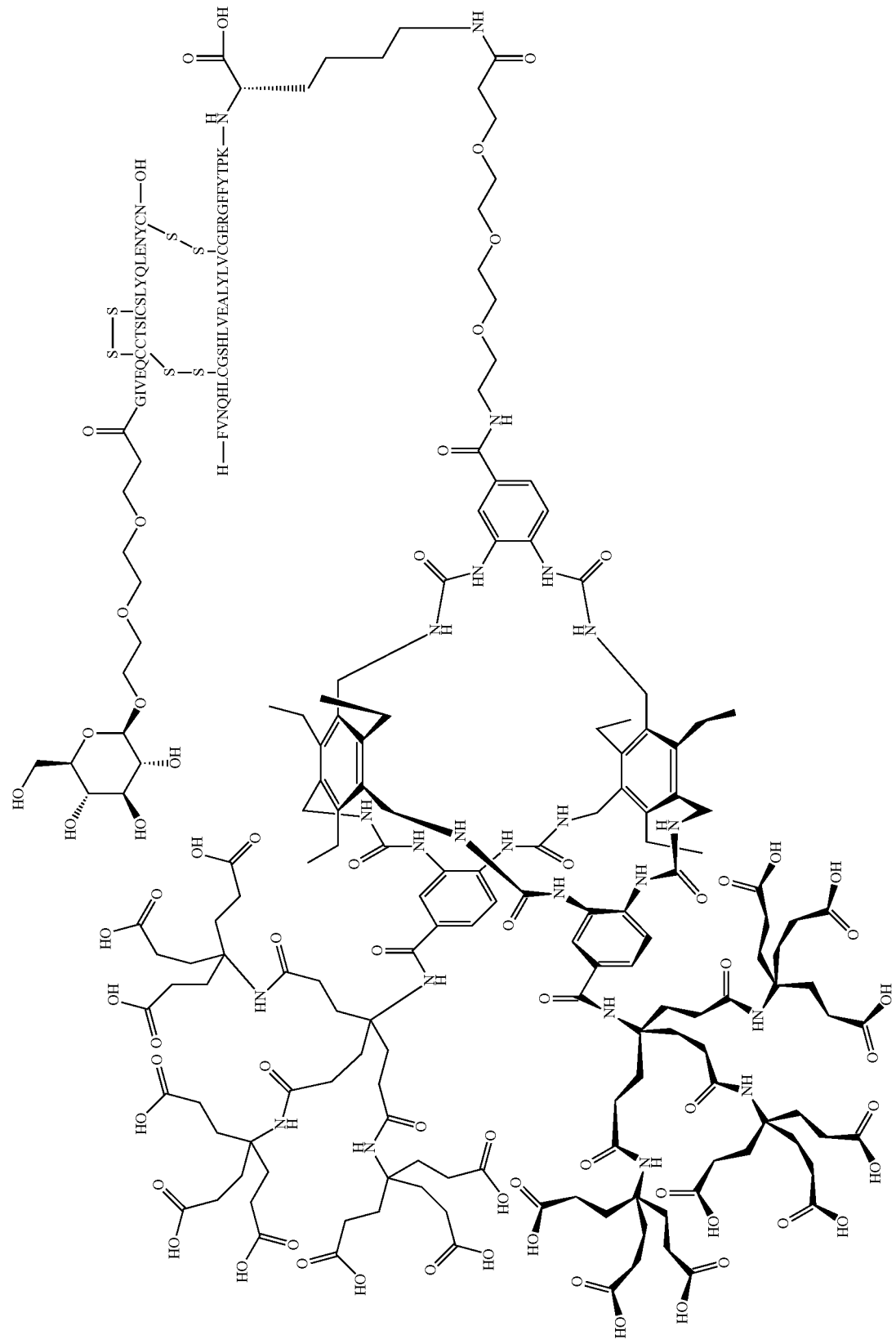

The carboxy macrocycle PEG 7d as prepared above is activated as succinimidyl ester as described for glucoside 8 and reacted with desB30 human insulin at pH 10.5 as described in example 1. The reaction is followed by LCMS, and the B29-macrocycle derivative is isolated using RP-HPLC as described above. The B29-macrocycle derivative is reacted with beta-glycoside active ester 8 at pH 7.5 as described in Example 3. The reaction is followed by LCMS, and the crude product is deprotected by treatment with 95% TFA 30 mins. The B29-macrocycle A1-glucoside INS5 of example 3 is isolated using RP-HPLC as described in Example 1, Step 1.

Example 4: Preparation of B1-Benzyl-3,5-Bis-Triazolyl-PEG4-G2macrocycle B29-Benzoyl-3,5-Methylamino-Bis-PEG3-Glycoside desB30 Human Insulin INS6

INS6

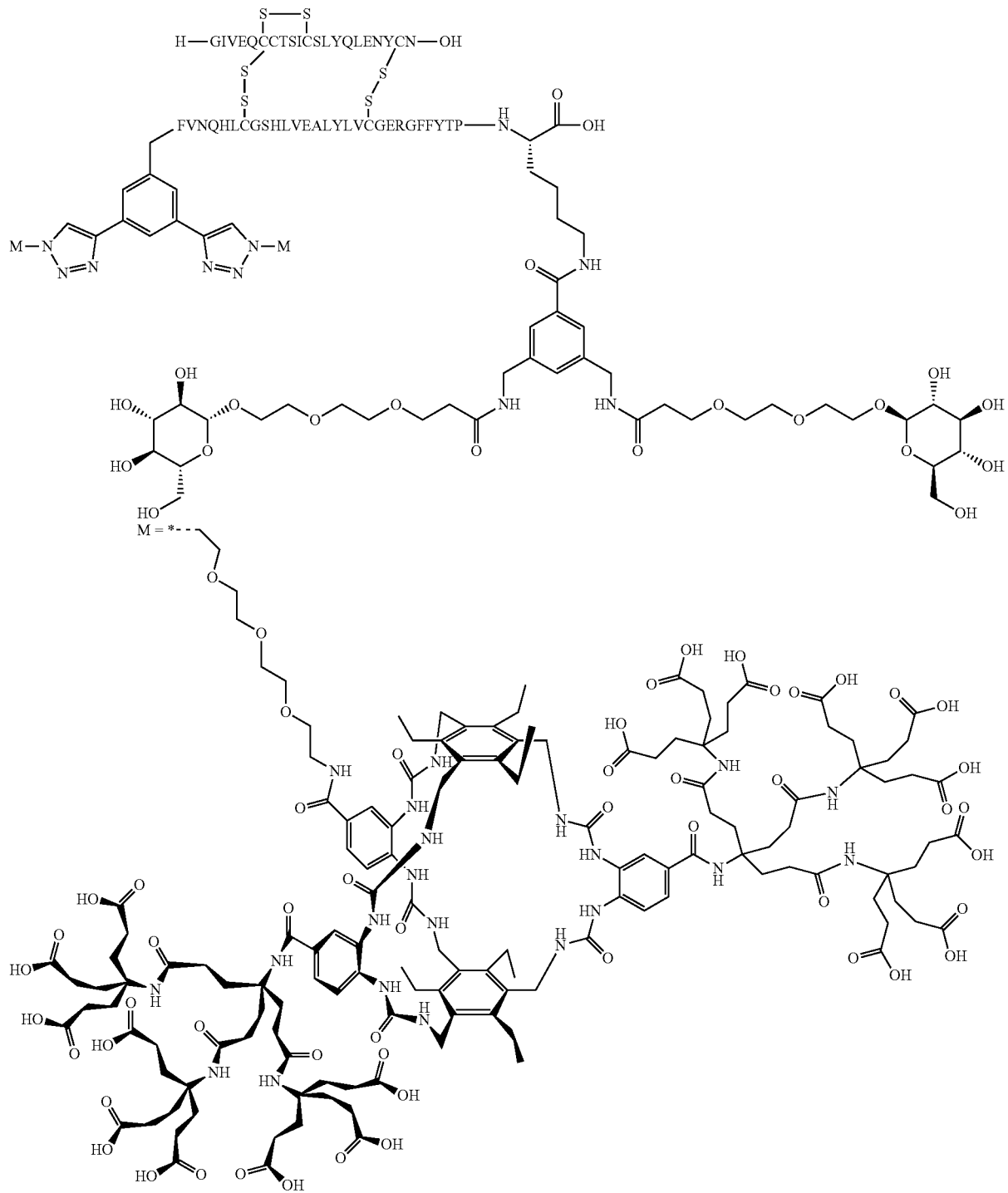

Point of attachments for M on insulin INS6 = *

Scheme 4
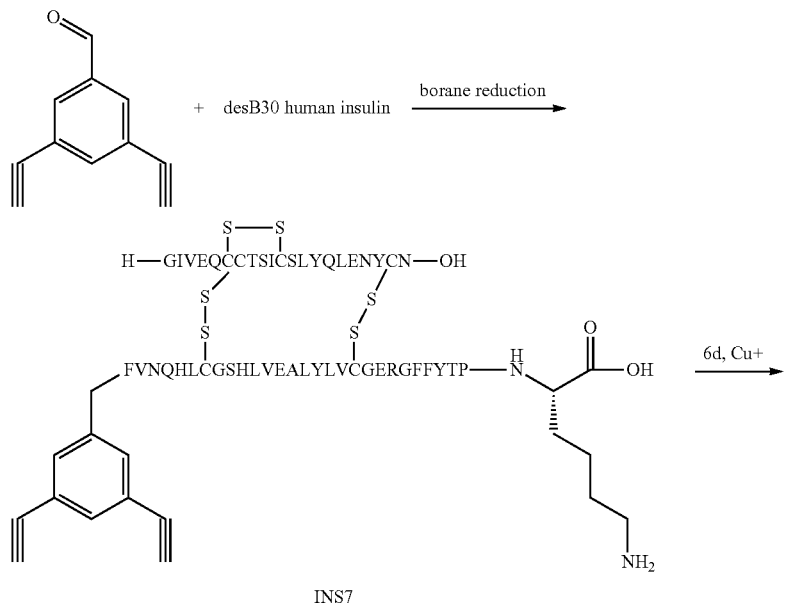
INS7
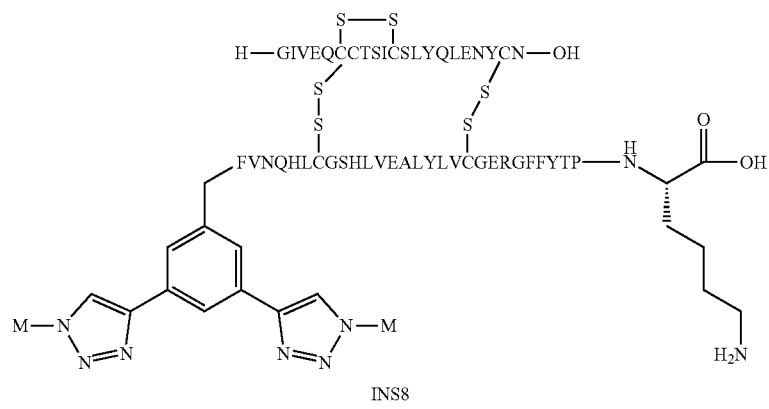
INS8

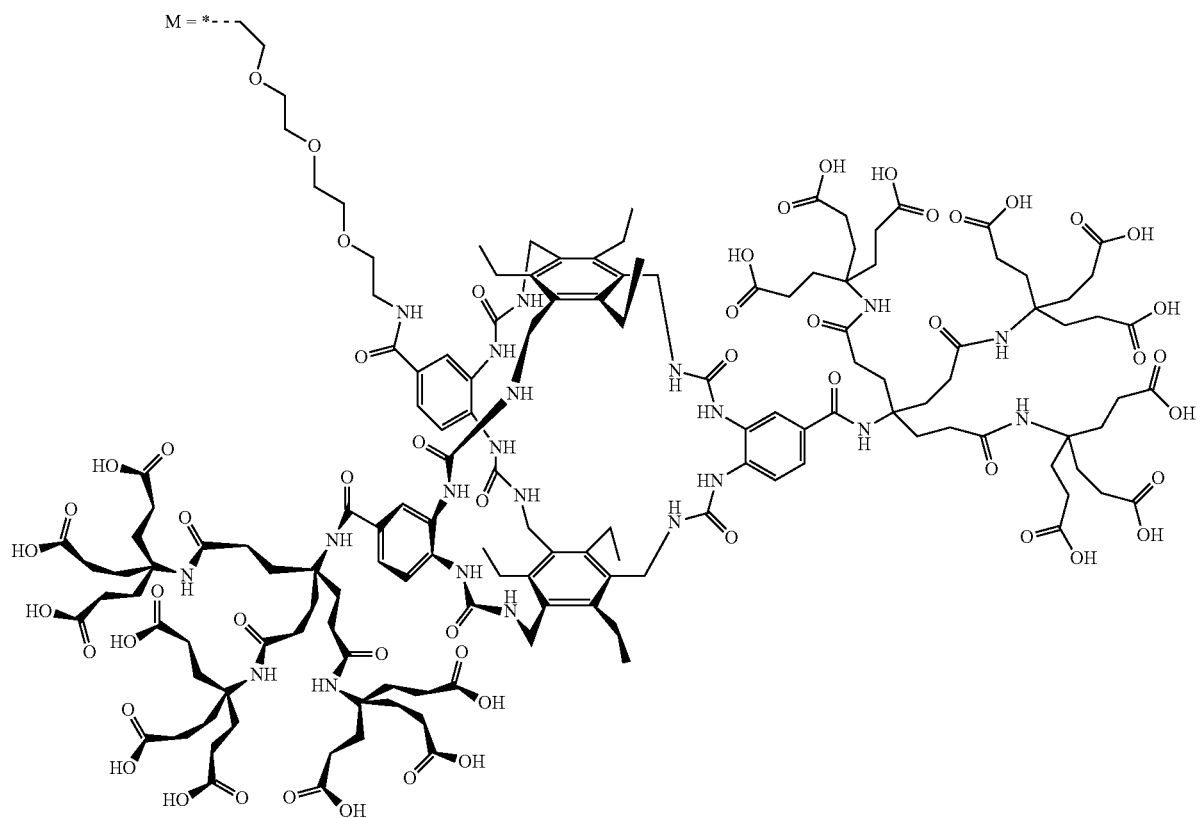

point of attachments for M on insulin INS8 = *

B1-3,5-bis-ethynyl-benzyl desB30 human insulin is produced from 3,5-bis-ethynyl-benzaldehyde and desB30 human insulin by reductive alkylation in analogy with the preparation of compound INS2 (Scheme 4). The bis-alkyne INS7 is reacted with macrocycle azide 6d under conditions as described for compound INS3, the reaction is followed by LCMS, and the intermediate INS8 is isolated using RP-HPLC as described in Example 1, Step 1. Active ester glucoside 8 is reacted with 3,5-bis-aminomethyl-benzoic acid. The purified product is activated as succinimidyl ester as described for glucoside 8, and reacted with insulin intermediate INS8 at pH 10.5 as described for INS3. The reaction is followed by LCMS, and the B1-bis-macrocycle B29-bis-glycoside desB30 human insulin INS6 of example 4 is isolated using RP-HPLC as described in Example 1, Step 1.

Example 5: Preparation of
B1-Benzyl-4-Triazolyl-PEG4-G2macrocycle
B29-Acetylethyleneglycol-D-Glycoside desB30
Human Insulin INS9
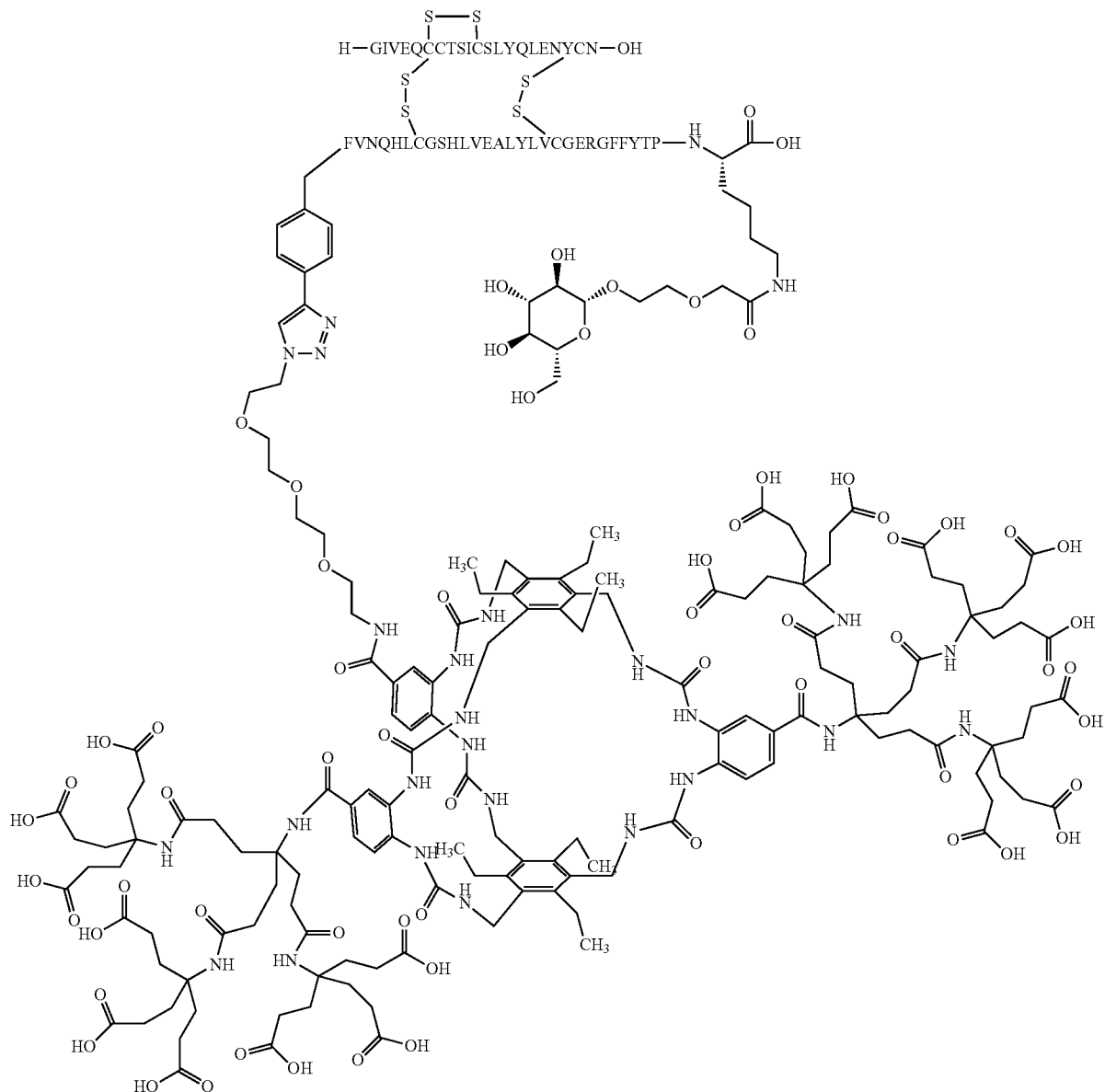
Step 1: INS2 was dissolved in 0.1 M $Na_2CO_3$ at pH 11 on icebath and treated with active ester 11 in THF for 10 mins. INS10 was isolated by HPLC similar to description in Example 1. LCMS measured 1564.25 $[M+4H]^{4+}$, calculated 1564.24.

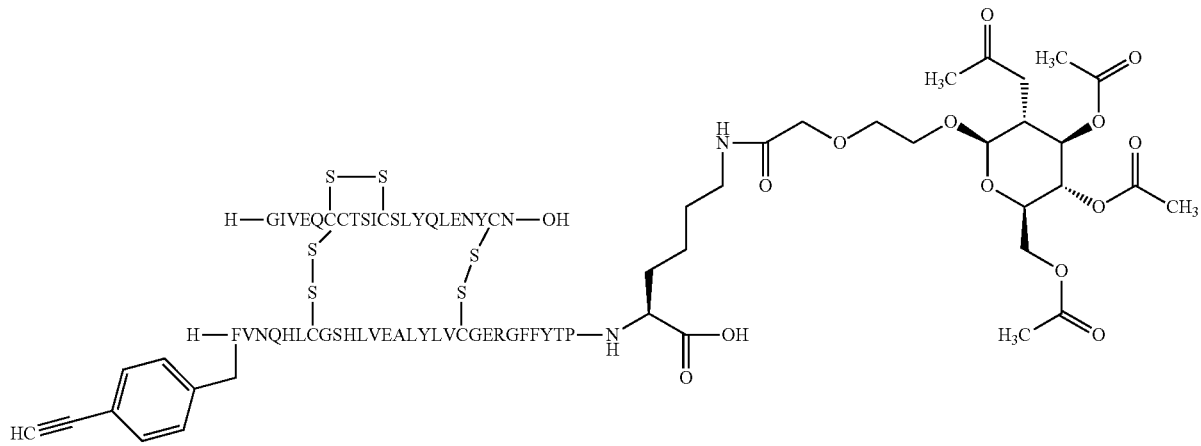

INS10

Step 2: INS10 was dissolved in 0.2 M K2CO3 with 33% MeOH and stirred 30 mins. INS11 was isolated by HPLC similar to description in Example 1. LCMS measured 1522.21 [M+4H]$^{4+}$, calculated 1522.21.

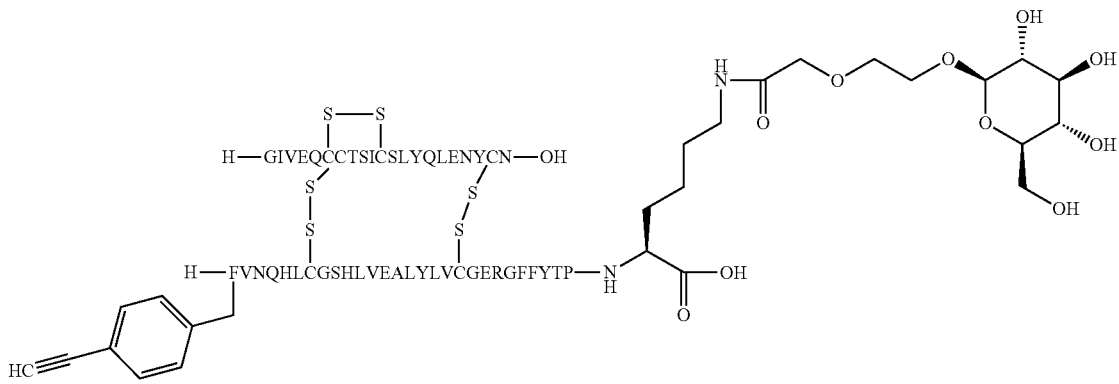

INS11

Step 3: INS11 (4.1 mg, 0.001 mmol) and macrocycle azide 6d (3.579 mg, 0.001 mmol) were dissolved in 2 M Et3N/CH3COOH aqueous buffer pH 7 (0.6 mL) and DMSO (0.3 mL) further diluted with water (0.3 mL), and the mixture degassed. The mixture was treated with THPTA (0.015 mg, 5 mol %) and with spatula tip of CuI and left 10 mins. INS9 was isolated by HPLC similar to description in Example 1, LCMS measured 1846.8 [M+5H]$^{5+}$, calculated 1847.0.

Example 8: Preparation of B1-Methyl-4-Triazolyl-PEG4-G1macrocycle B29-PEG4-Glycoside desB30 Human Insulin INS18

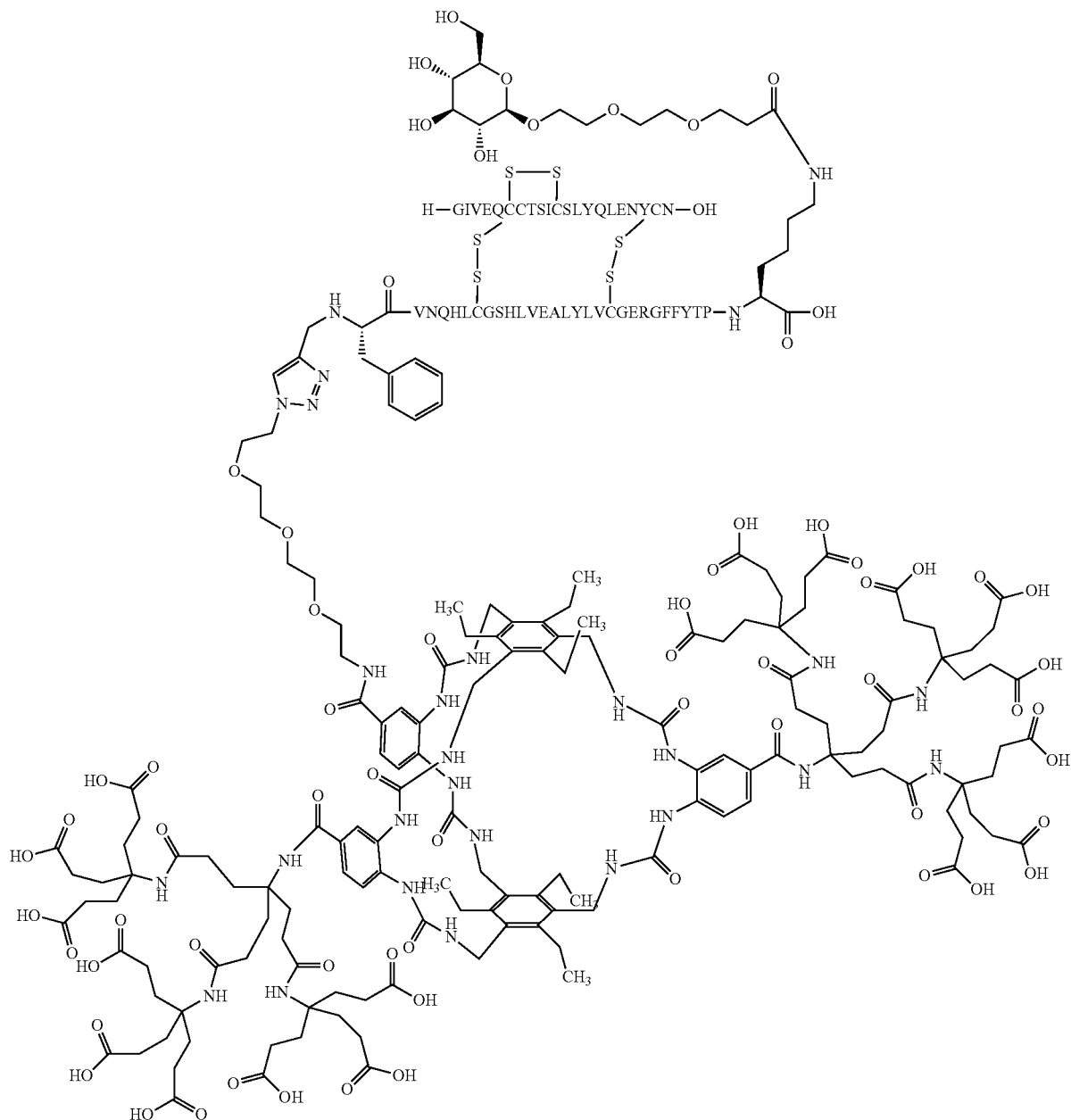

Step 1: DesB30 human insulin (1.71 g, 0.3 mmol) was dissolved in 0.1M AcOH/water (5 mL)+MeOH (5 mL). Propynal was added (29 mg, 0.54 mmol), the mixture was stirred 15 mins, then treated with more propynal (15 mg), and stirred for 30 mins. Alpha-picoline borane (192 mg, 1.8 mmol) in DMF was added, and the mixture was stirred 1 h. INS19 was isolated by HPLC similar to description in Example 1. LCMS measured 1436.8 [M+4H]$^{4+}$, calculated 1437.1.

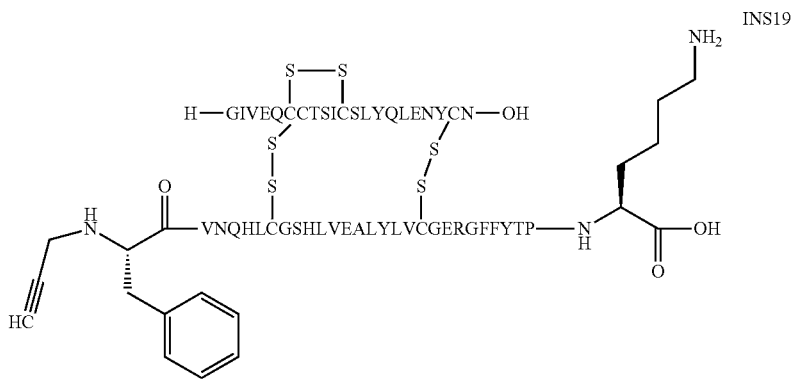

INS19

Step 2: INS19 (150 mg, 0.026 mmol) was dissolved 0.1M Na2HPO4 buffer pH 11.5 (3 mL) and reacted with glucoside active ester 8 for 1 h. INS20 was isolated by HPLC similar to description in Example 1. LCMS measured 1517.4 [M+4H]$^{4+}$, calculated 1517.7

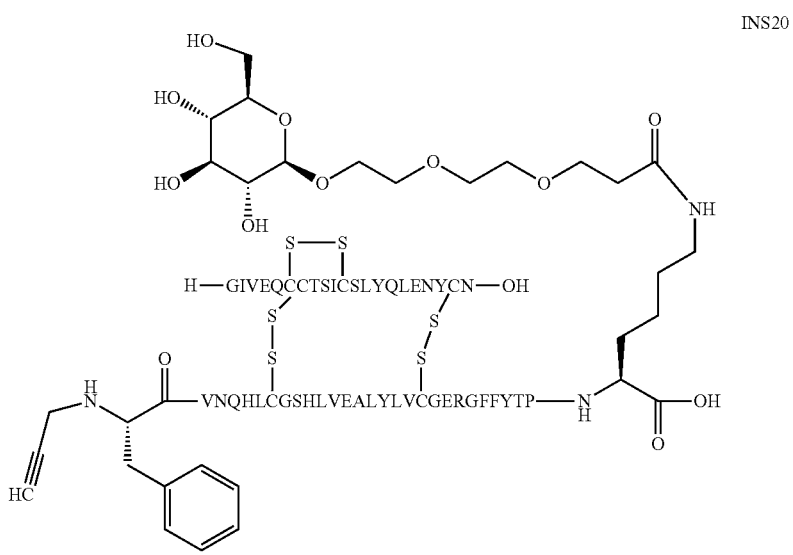

INS20

Step 3: INS20 (11 mg, 1.8 umol) and macrocycle azide 6d (8.3 mg, 2.4 umol) were dissolved in 2 M triethanolamine pH 7.0 (0.4 mL)+DMSO (0.8 mL). THPTA was added (0.236 mg, 0.54 umol) and the mixture was degassed carefully. CuI was added (0.003 mg, 0.018 umol) and the mixture was stirred 90 mins. INS18 was isolated by HPLC similar to description in Example 1. LCMS measured 1843.5 [M+5H]$^{5+}$, calculated 1843.4

Example 9: Preparation of
B1-Benzyl-4-Triazolyl-PEG4-G2macrocycle
B29-Acetyldiethyleneglycol-Glycoside desB30
Human Insulin INS21

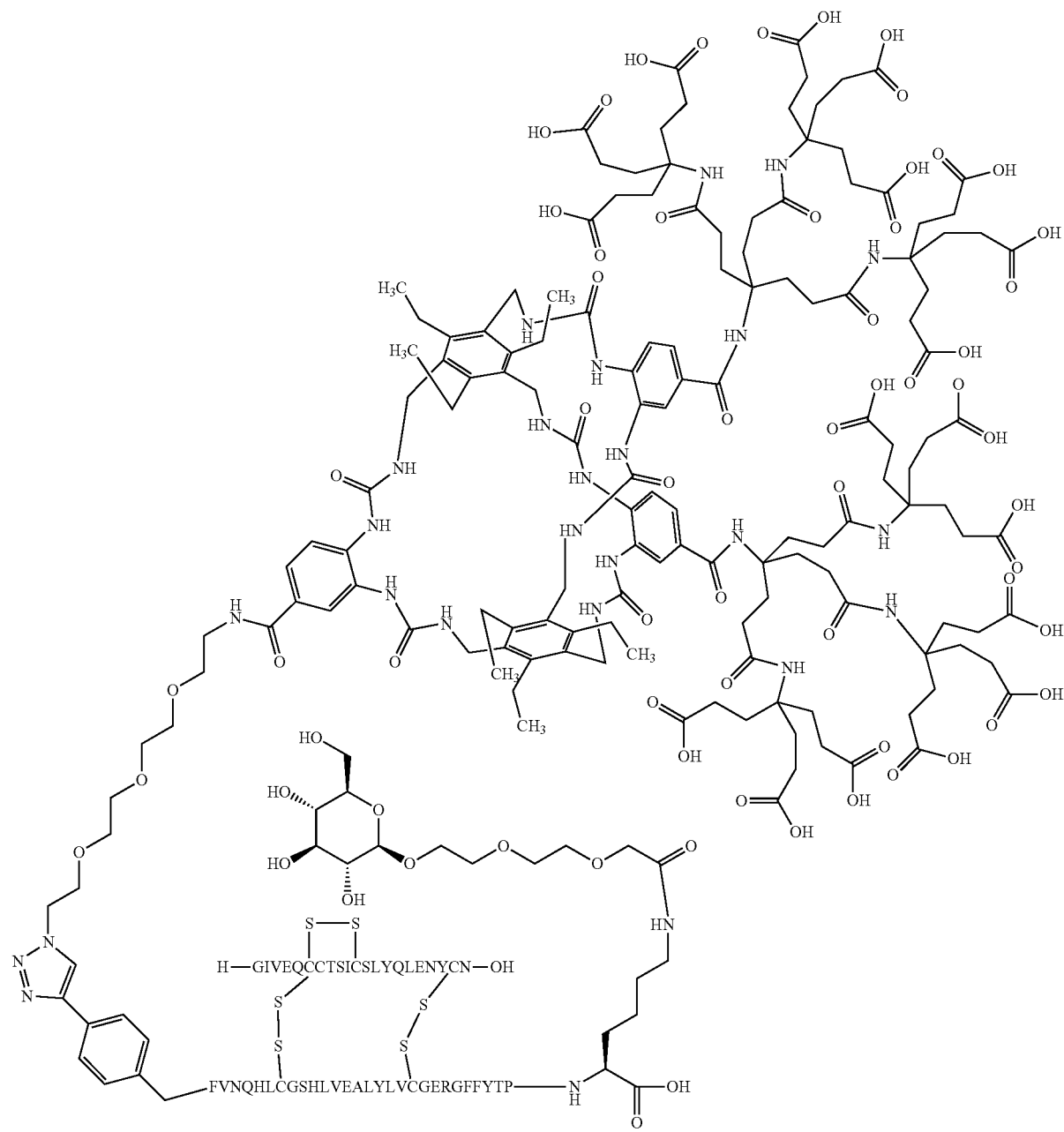

INS21 was prepared similarly to INS9, using triethylenglycol for making the glucoside, and macrocycle azide 6d. INS21 LCMS measured 1855.7 $[M+5H]^{5+}$, calculated 1855.9.

Example 10: Preparation of B1-Benzyl-3,5-Bis-Triazolyl-PEG4-G1macrocycle B29-Nε-Propanoyl, Cα-Aminomethyl-Bis-Triazolyl-PEG4-Glycoside desB30 Human Insulin INS22

INS22
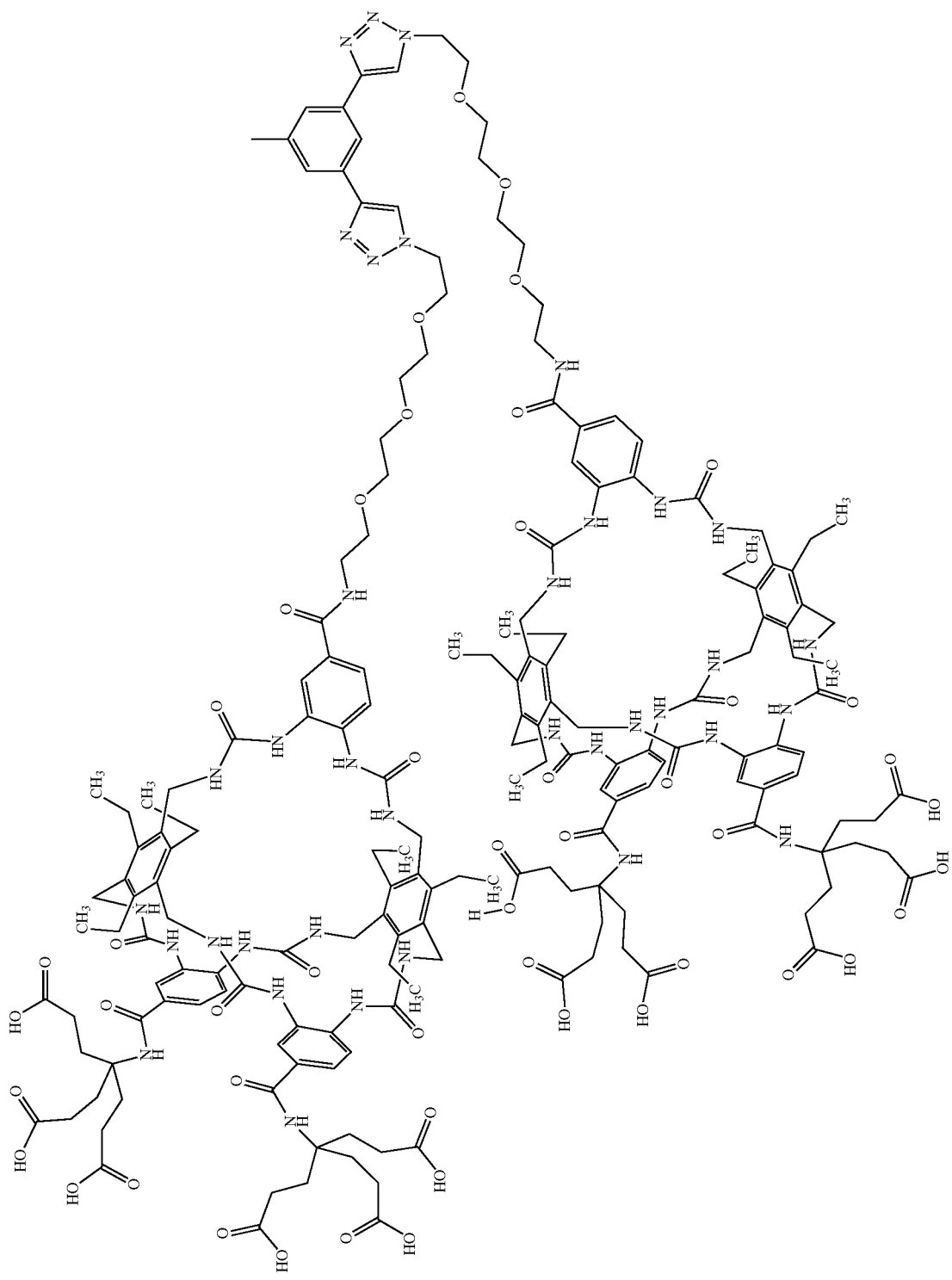

-continued
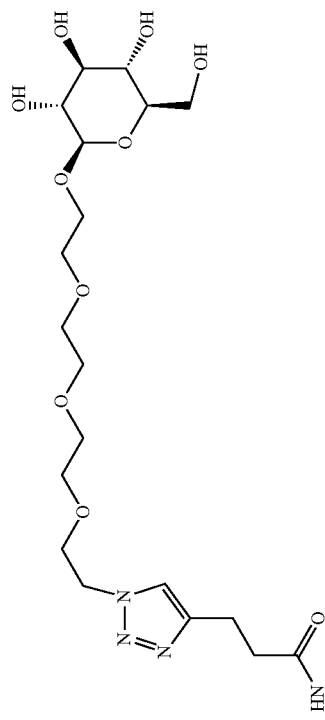
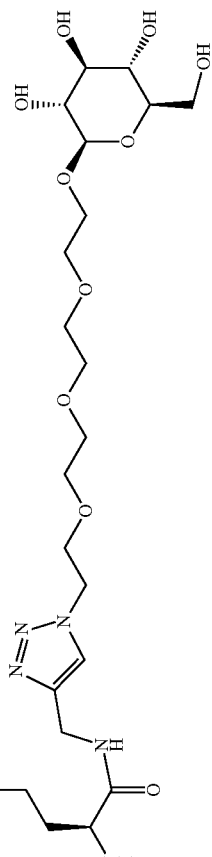

Step 1: DesB30 human insulin (120 mg, 0.21 mmol) and propargylamine (100 mg, 1.8 mmol) were dissolved in a mixture of DMSO (1 mL), DMF (1 mL), ethanol (1 mL) and 0.1 M sodium phosphate pH 7 (1 mL), adjusted to pH 7.0 with TFA. A solution of achromobactor lyticus protease was added (40 uL, 6.3 mg/mL), and the mixture was left overnight. INS23 was isolated by HPLC similar to description in Example 1. LCMS measured 1436.5 [M+4H]$^{4+}$, calculated 1436.9.

HPLC as described in Example 1. LCMS measured 1456.6 [M+4H]$^{4+}$, calculated 1456.9.

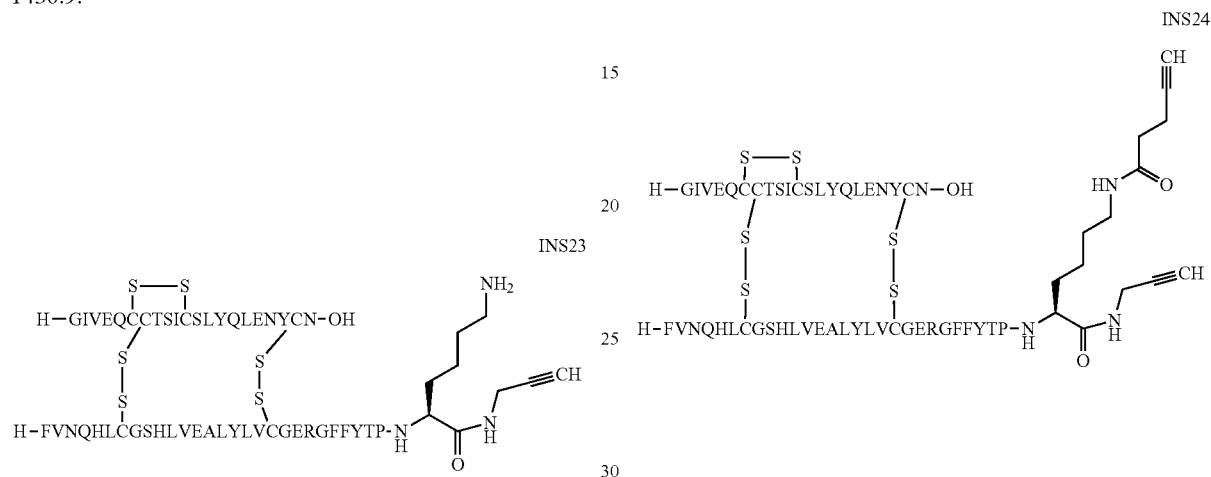

Step 2: INS23 (300 mg, 52 umol) was dissolved in 0.1 M Na$_2$CO$_3$ buffer pH 11 (15 mL), and treated with 0-succinimidyl pentynate (10.1 mg, 51 umol) dissolved in DMSO (1 mL). The reaction was left 1 h, and INS24 was isolated by Step 3: INS24 (97 mg, 17 umol) was reacted with compound 12 (12.7 mg, 33 umol) using THPTA and CuI as described for INS3. INS25 was isolated by HPLC as described in Example 1. LCMS measured 1647.4 [M+4H]$^{4+}$, calculated 1647.6

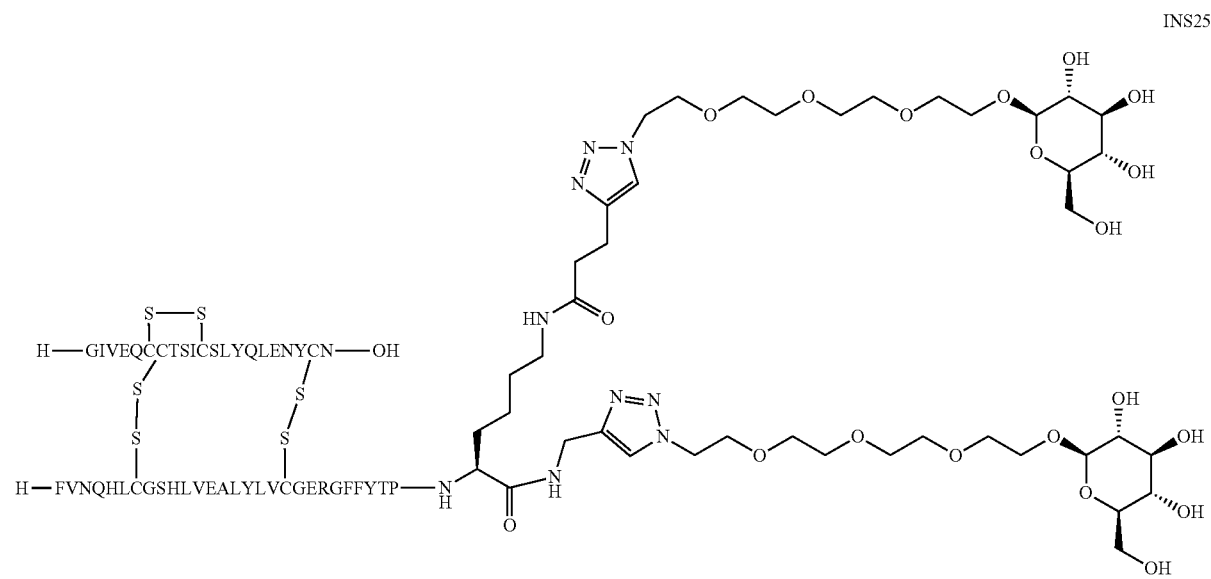

Step 4: INS25 (85 mg, 13 umol) was dissolved in 50% acetonitrile/water (1.2 mL) and treated with 3,5-diethynyl-benzaldehyde (3.1 mg, 21 umol). pH was adjusted to 4 using 0.1 M $Na_2CO_3$. NaCNBH3 was added (4 mg, 65 umol) and the mixture was left overnight. INS26 was isolated by HPLC similar to description in Example 1. LCMS measured 1345.7 $[M+5H]^{5+}$, calculated 1345.9

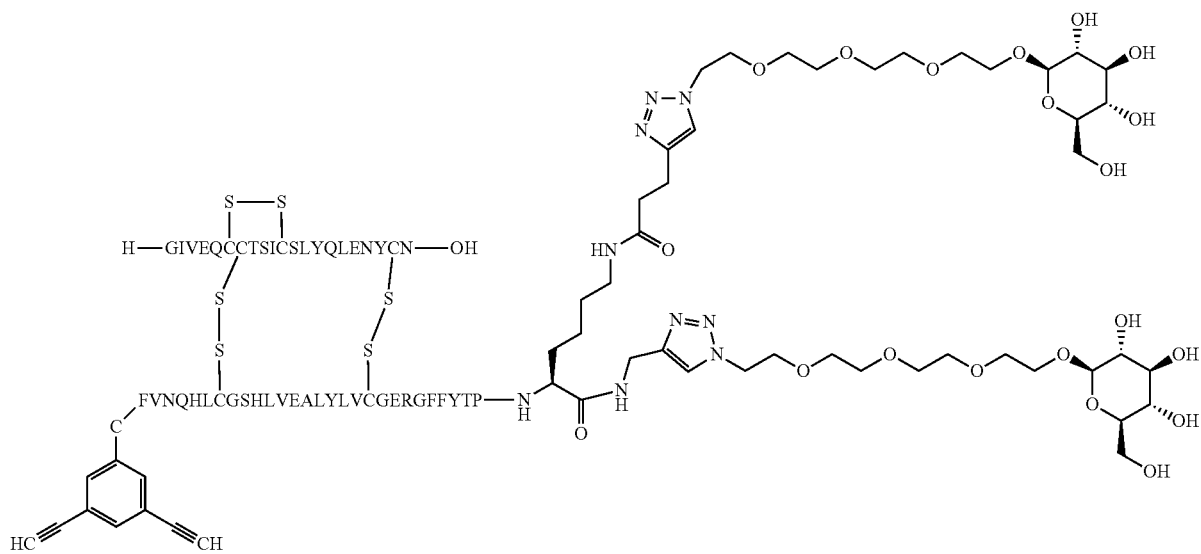

INS26

Step 5: INS26 (24 mg, 4 umol), compound 16 (20 mg, 11 umol), THPTA (1 mg) and methyl-beta-D-glycopyranoside (20 mg) was dissolved in 2 M $Et_3N$/AcOH (1 mL)+DMSO (1 mL) and degassed. Treated with spatula tip of CuI and left 2 h. INS22 was isolated by HPLC similar to description in Example 1. LCMS measured 1711.5 $[M+6H]^{6+}$, calculated 1711.7

Example 11: Preparation of B1-Benzyl-4-Triazolyl-PEG4-G2macrocycle B29-Acetyl-Glycoside desB30 Human Insulin INS27
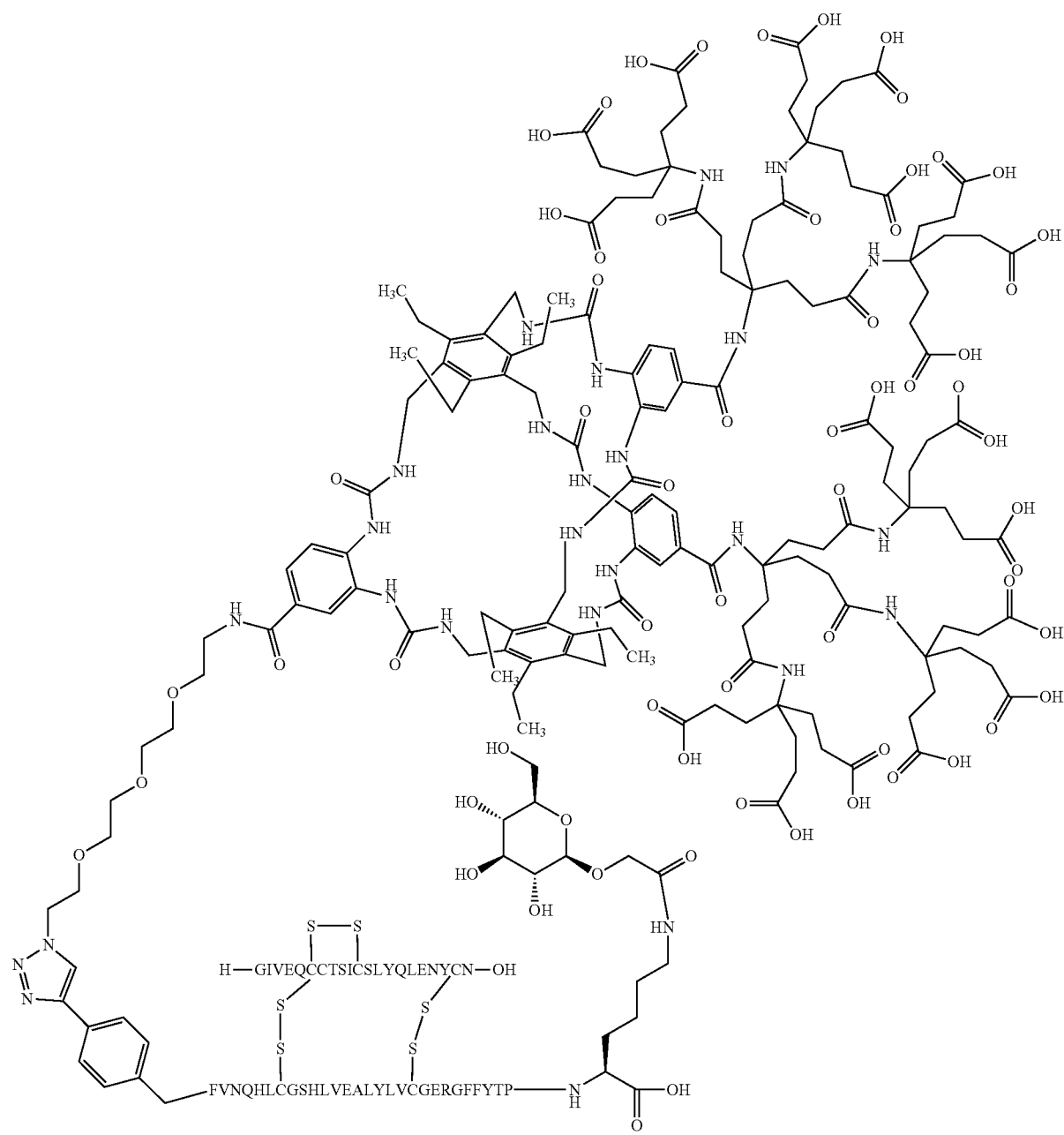
INS27 was prepared similarly to INS9, using ethylenglycol for making the glucoside, and macrocycle azide 6d. INS27 LCMS measured 1838.2 $[M+5H]^{5+}$, calculated 1838.2.

Example 12: Preparation of B1-Methyl-4-Triazolyl-PEG3-G1macrocycle B29-PEG3-Glycoside desB30 Human Insulin INS28

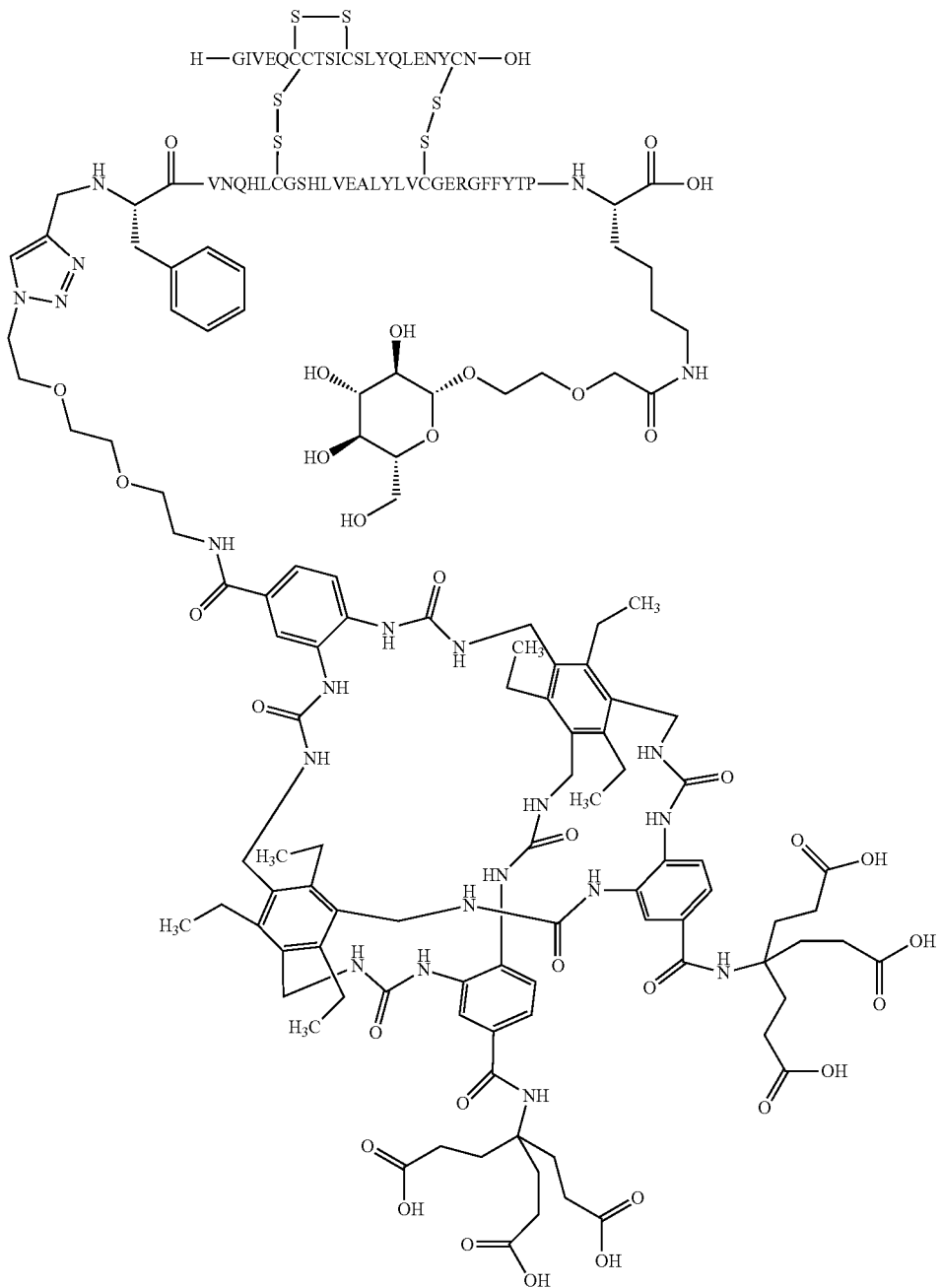

INS20 (36.4 mg, 6 umol) and compound 20 (14.5 mg, 7.8 umol) were dissolved in DMSO (4 mL)+2 M triethylamine pH 7.0 (3 mL). THPTA was added (0.78 mg, 1.8 umol) and the flask was degassed. CuI was added (0.011 mg, 0.06 umol) and the mixture was left 1 h. INS28 was isolated by HPLC similar to description in Example 1. LCMS measured 1559.2 $[M+5H]^{5+}$, calculated 1559.5

Example 13: B1-Benzyl-3,5-Bis-Triazolyl-PEG4-G1macrocycle B29-Cα-Ethylenediamine-Methyltriazolyl-PEG4-Glycoside desB30 Human Insulin INS29

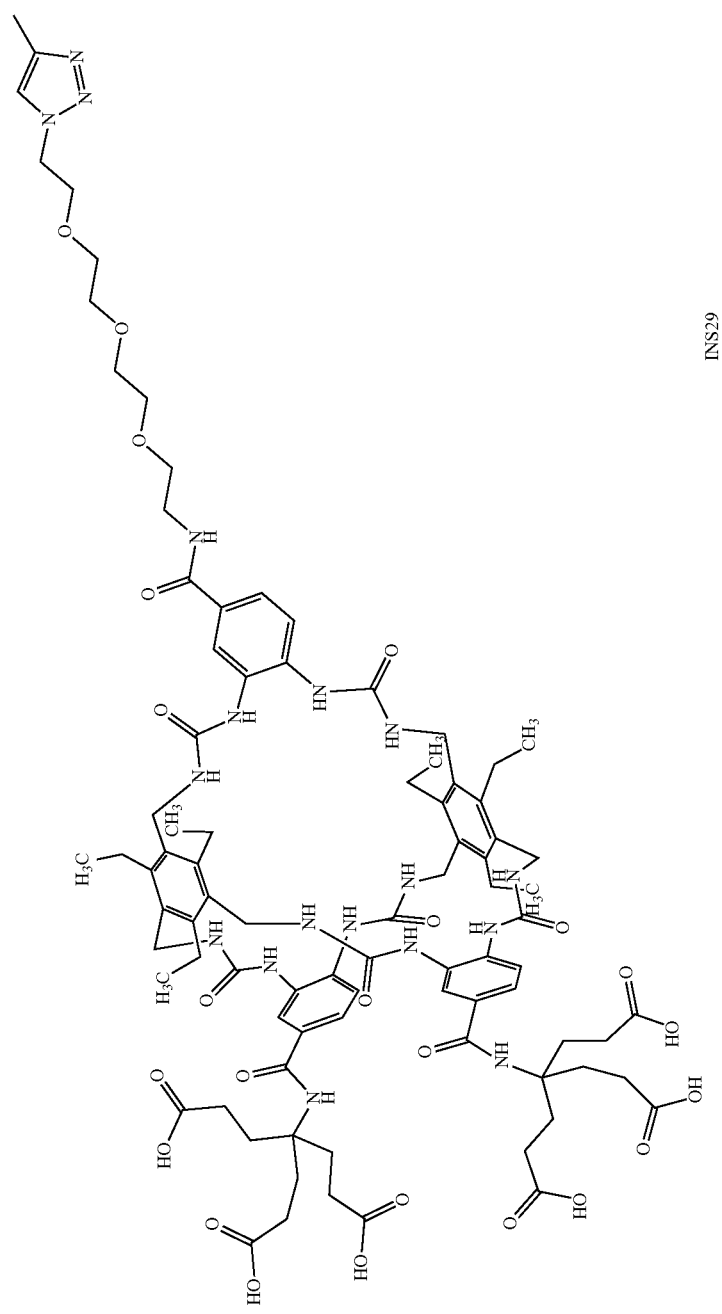

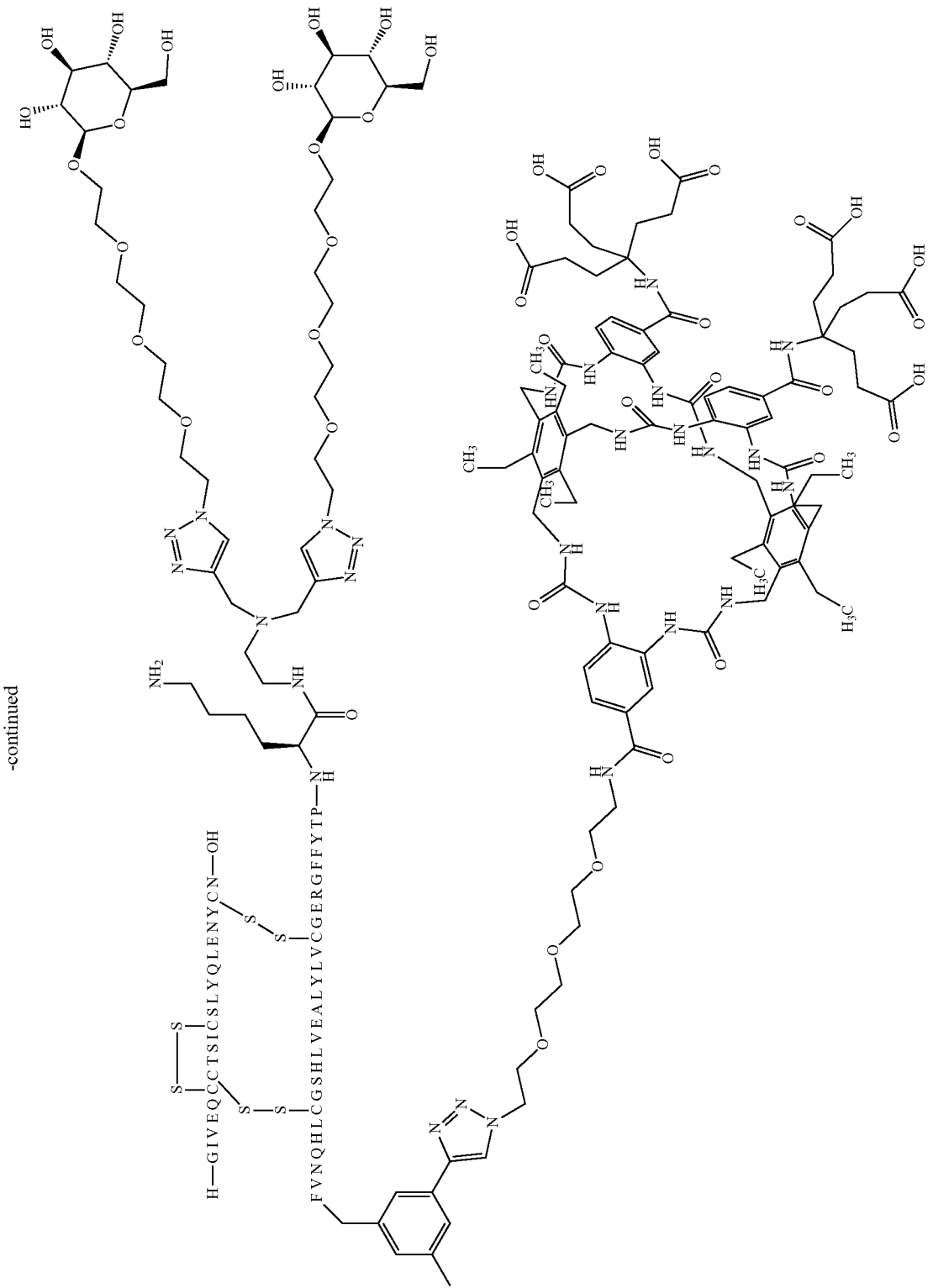

N,N-dipropynyl-ethylenediamine was conjugated to Cα of B29 in desB30 human insulin by enzymatic coupling as described for INS23. Azide PEG4 glucoside 12 was double conjugated to the alkynes as described for INS3, and B1 of the product was reductively alkylated with 3,5-diethynyl-benzaldehyde as described for INS26. The product was conjugated to G1 macrocycle PEG4 azide (compound 16) as described for synthesis of INS22, and the product was purified by HPLC as described for INS1. LCMS measured 1711.8 $[M+6H]^{6+}$, calculated 1711.9.

Example 14:
B1-Methyl-4-Triazolyl-PEG4-G1macrocycle
B29Nε-PEG3-Glycoside desB30 Human Insulin
INS30

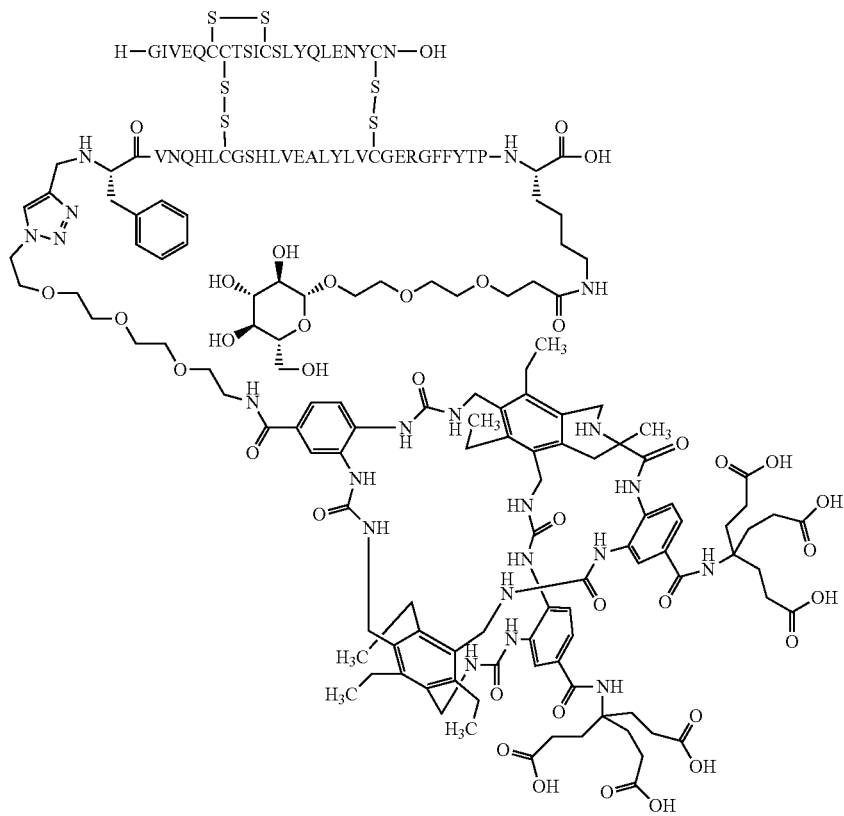

INS 30

INS30 was prepared from INS20 and G1 macrocycle PEG4 azide 16 as described for INS9, and purified by HPLC as described for INS1. LCMS measured 1568.1 $[M+5H]^{5+}$, calculated 1568.3

Example 15:
B1-Methyl-4-Triazolyl-Propyl-G1macrocycle
B29Nε-Acetyl-Glycoside desB30 Human Insulin
INS31
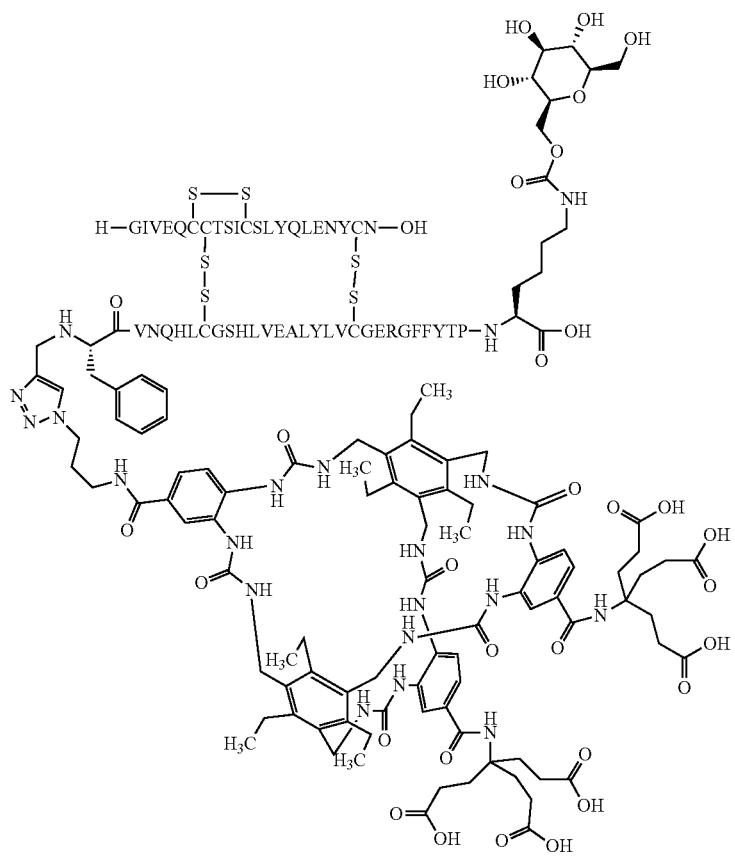
INS31 was prepared as INS18 from 1-acetyl-glucoside and G1 macrocycle propyl azide 21, and purified by HPLC as described for INS1. LCMS measured 1524.2 $[M+5H]^{5+}$, calculated 1524.3.

Example 16:
B1-Benzyl-3,5-Triazolyl-PEG4-G1macrocycle
B29Nε-Benzoyl-3,5-Triazolyl-PEG4-Glycoside
desB30 Human Insulin INS32

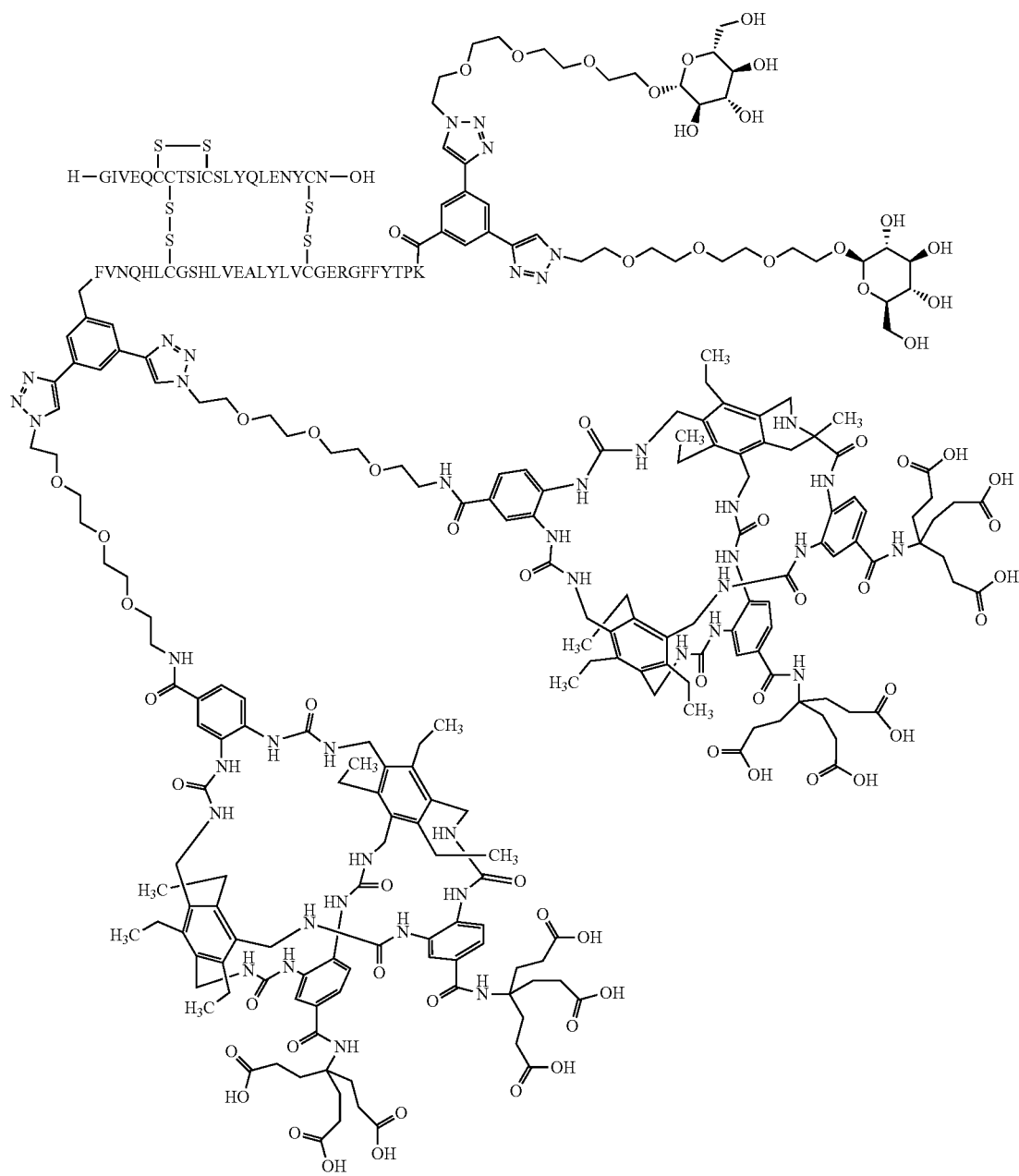

INS32

INS32 was prepared by acylating desB30 human insulin in B29 using succinimidyl 3,5-diethynylbenzoate, as described for INS23, followed by reaction with glucoside PEG4 azide 12 as described for INS3, then followed by reductive alkylation using 3,5-diethynylbenzaldehyde as described for INS26. The product was conjugated to G1macrocycle-PEG4-azide (compound 16) as described for synthesis of INS22, and the product was purified by HPLC as described for INS1. LCMS measured 1717.3 $[M+6H]^{6+}$, calculated 1717.6.

Example 17: B1-Benzyl-3,5-Triazolyl-Propyl-G1macrocycle B29Nε-B29-Benzoyl-3,5-Triazolyl-PEG4-Glycoside desB30 Human Insulin INS33

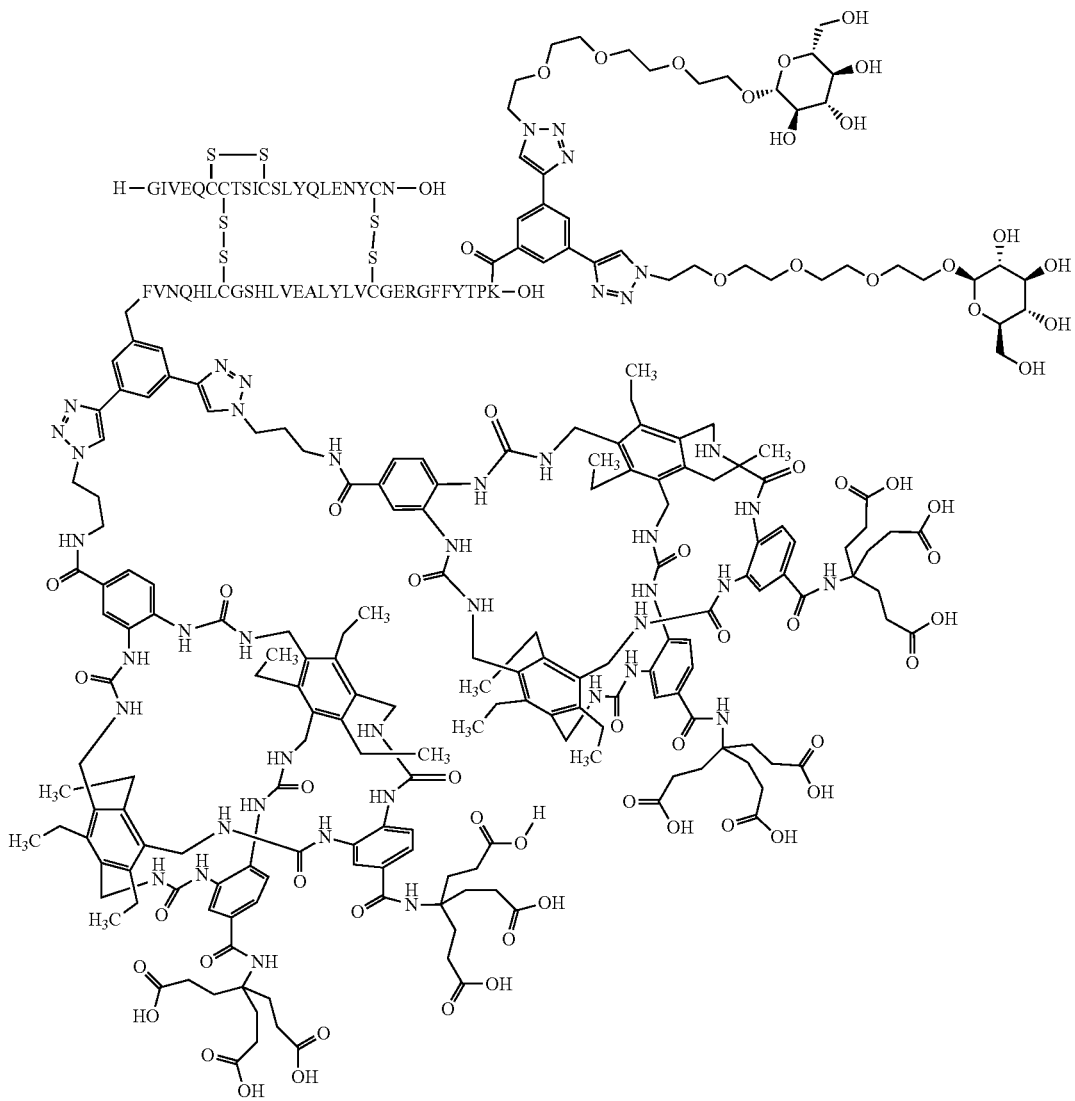

INS33 was prepared from desB30 human and succinimidyl 3,5-diethynylbenzoate as described for INS32, followed by reaction with glucoside PEG4 azide 12 as described for INS3, then followed by reductive alkylation using 3,5-diethynylbenzaldehyde as described for INS26. The product was conjugated to G1macrocycle-propyl azide (compound 21) as described for synthesis of INS32, and the product was purified by HPLC as described for INS1. LCMS measured 1677.9 $[M+6H]^{6+}$, calculated 1678.2.

Example 18:
B1-Methyl-Triazolyl-Propyl-G1macrocycle B29Nε-PEG3-Glycoside desB30 Human Insulin
INS34
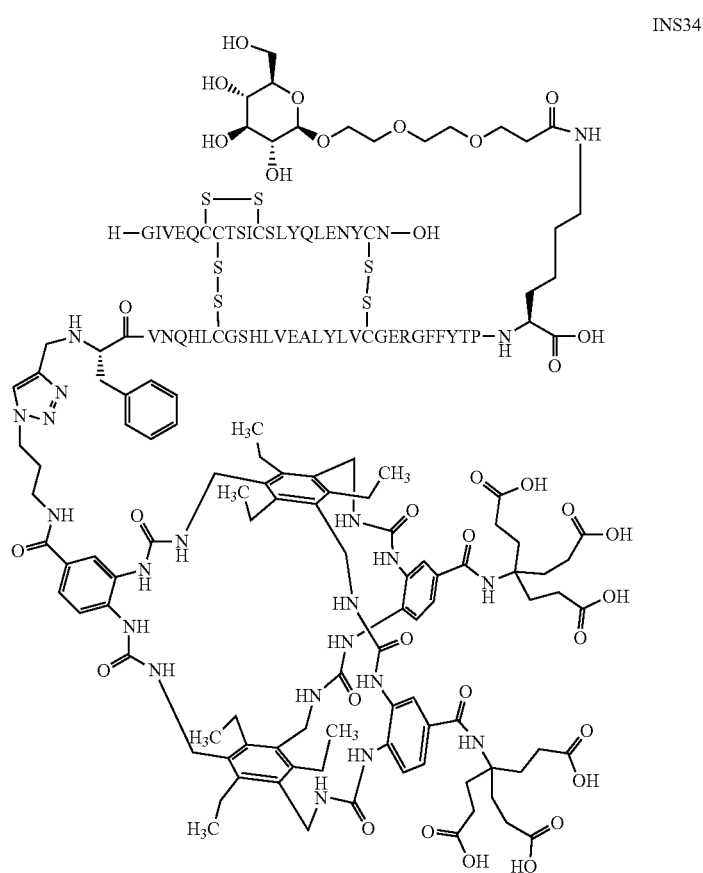
INS34
INS34 was prepared from INS20 and G1 macrocycle propyl azide 21 as described for INS9. The product was purified by HPLC as described for INS1. LCMS measured 1930.7 [M+4H]$^{4+}$, calculated 1930.7.

Example 19:
B1-Propanoyl-Triazolyl-PEG3-G2macrocycle B29Nε-PEG3-Glycoside desB30 Human Insulin
INS35

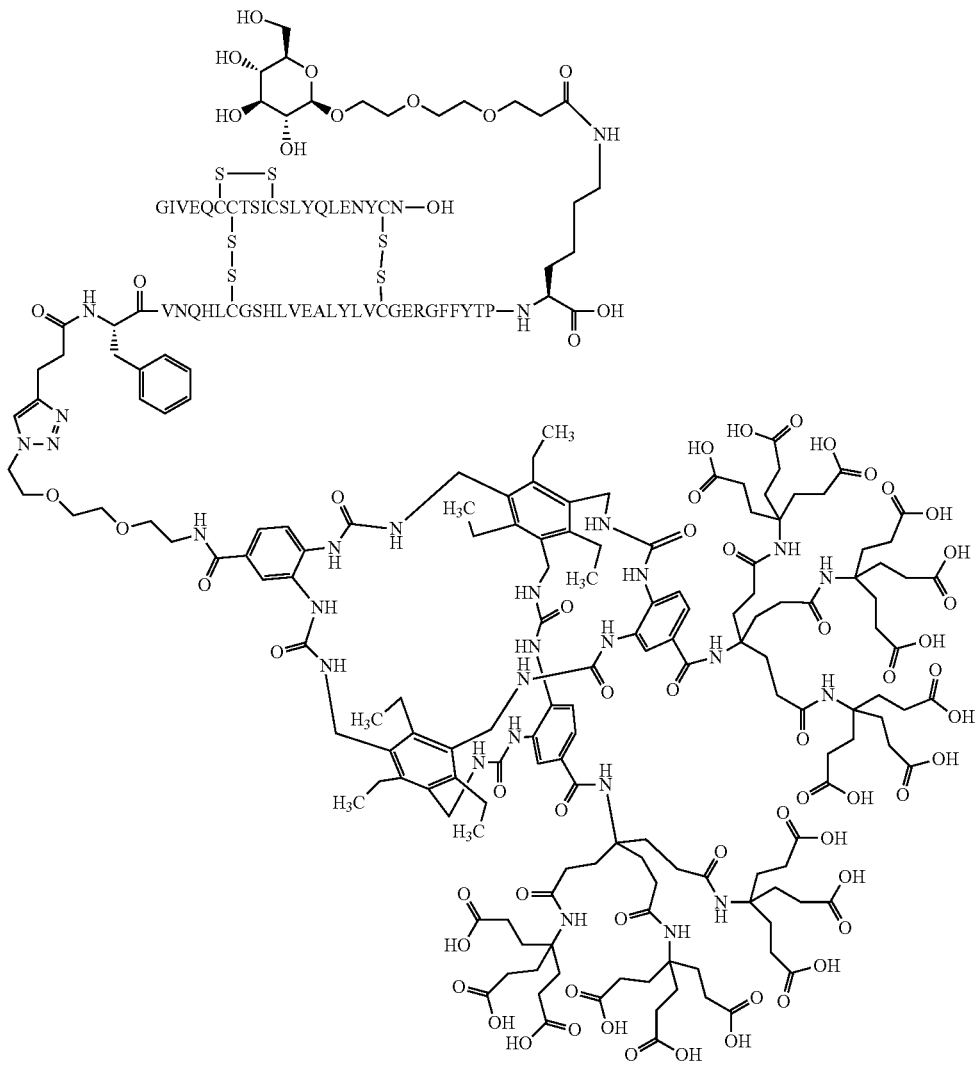

INS35

A1-Boc desB30 human insulin (EP0132770) was reacted with glucoside PEG3 active ester 8 as described for INS20. The product was purified by HPLC as described for INS1, and B1 acylated using succinimidyl pentynate, and the product was purified by HPLC as described for INS1. The product was conjugated with G2-macrocycle PEG3 azide 22 as described for INS9. LCMS measured 1843.1 [M+5H]$^{5+}$, calculated 1843.0.

Example 20:
B1-Propanoyl-Triazolyl-PEG5-G2macrocycle
B29Nε-PEG3-Glycoside desB30 Human Insulin
INS36

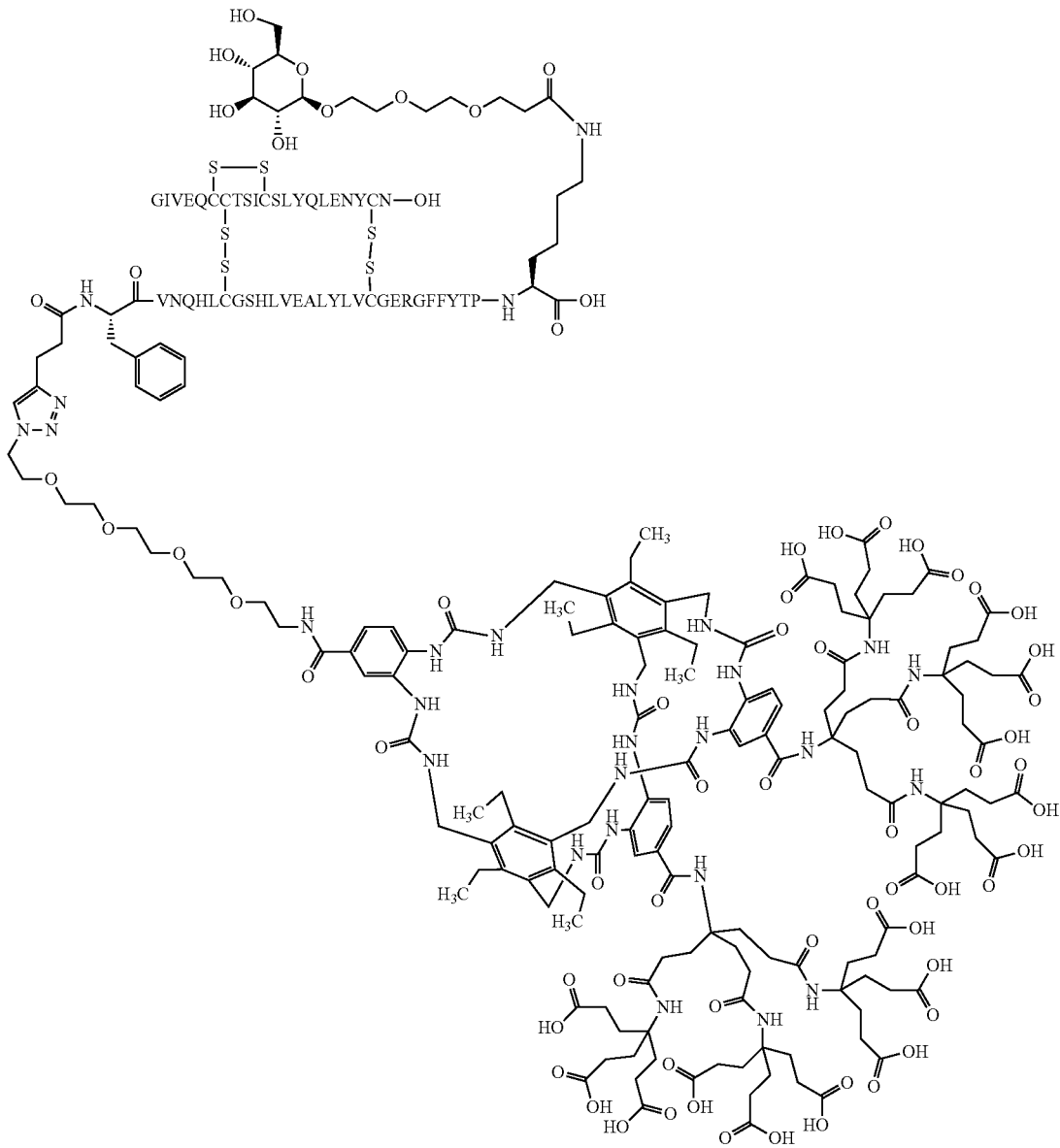

INS36

A1-Boc desB30 human insulin was reacted with glucoside PEG3 active ester 8 as described for INS20. The product was purified by HPLC as described for INS1, and B1 acylated using succinimidyl pentynate, and the product was purified by HPLC as described for INS1. The product was conjugated with G2-macrocycle PEG5 azide 23 as described for INS9. LCMS measured 1860.73 [M+5H]$^{5+}$, calculated 1860.6.

Example 21:
B1-Methyl-Triazolyl-PEG5-G1macrocycle
B29Nε-PEG3-Glycoside desB30 Human Insulin
INS37
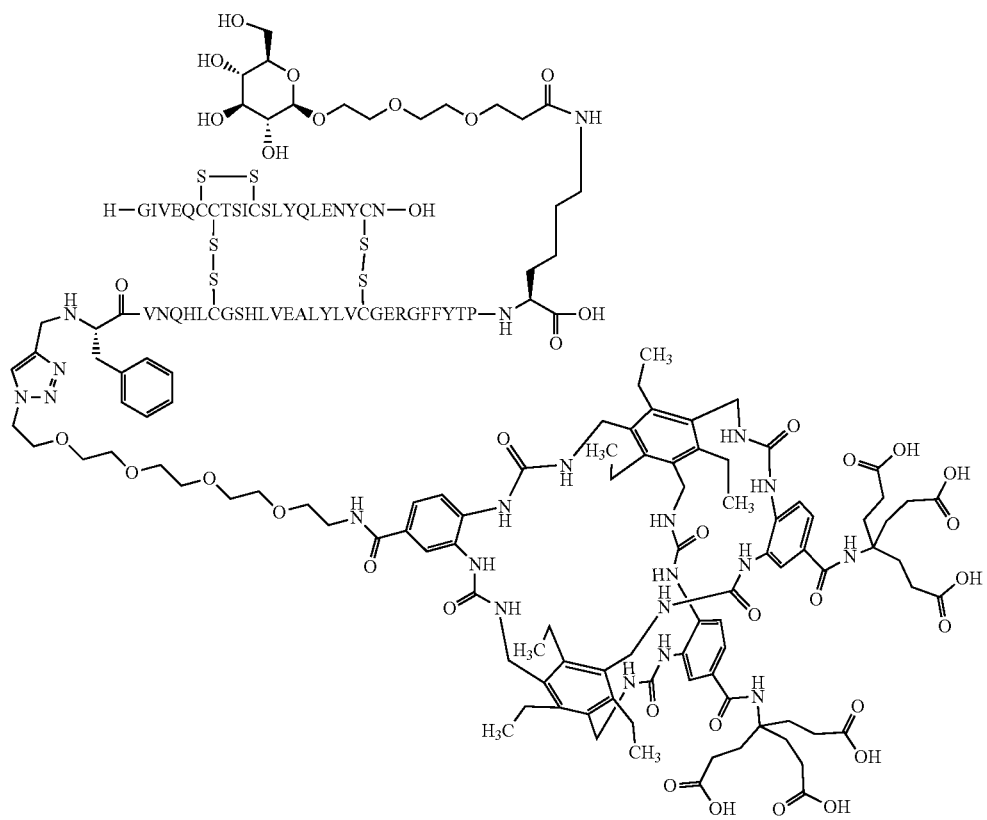
INS37
INS37 was prepared from INS20 and G2 macrocycle PEG5 azide 24 as described for INS9. The product was purified by HPLC as described for INS1. LCMS measured 1971.3 $[M+4H]^{4+}$, calculated 1971.2.

Example 22:
B1-Methyl-Triazolyl-PEG4-G0macrocycle
B29Nε-PEG3-Glycoside desB30 Human Insulin
INS38
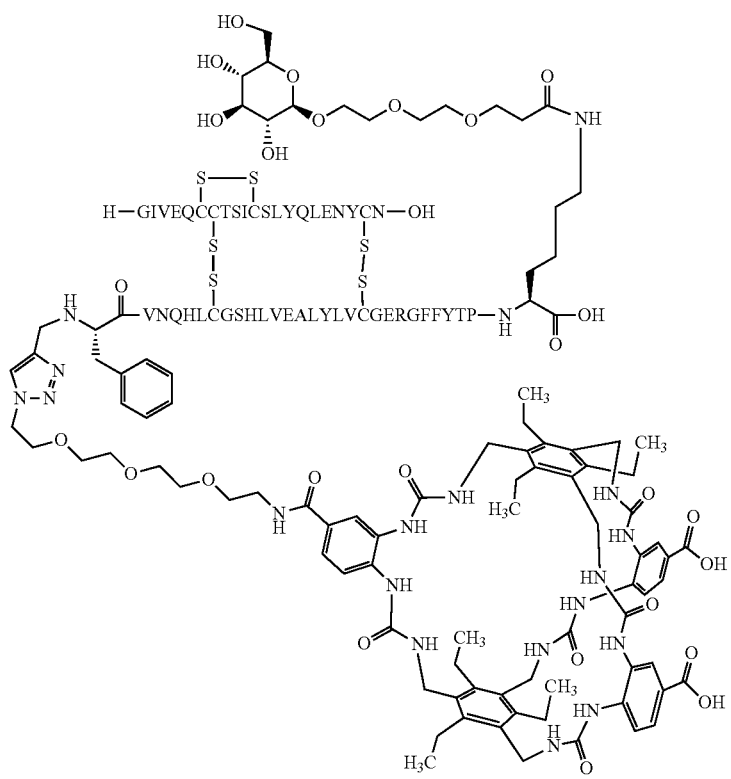
INS38
INS38 was prepared from INS20 and G0 macrocycle PEG4 azide 25 as described for INS9. The product was purified by HPLC as described for INS1. LCMS measured 1845.4 $[M+4H]^{4+}$, calculated 1845.6.

Example 23:
B1-Methyl-Triazolyl-PEG4-G1macrocycle B29NεAcetyl-Glycoside desB30 Human Insulin
INS39
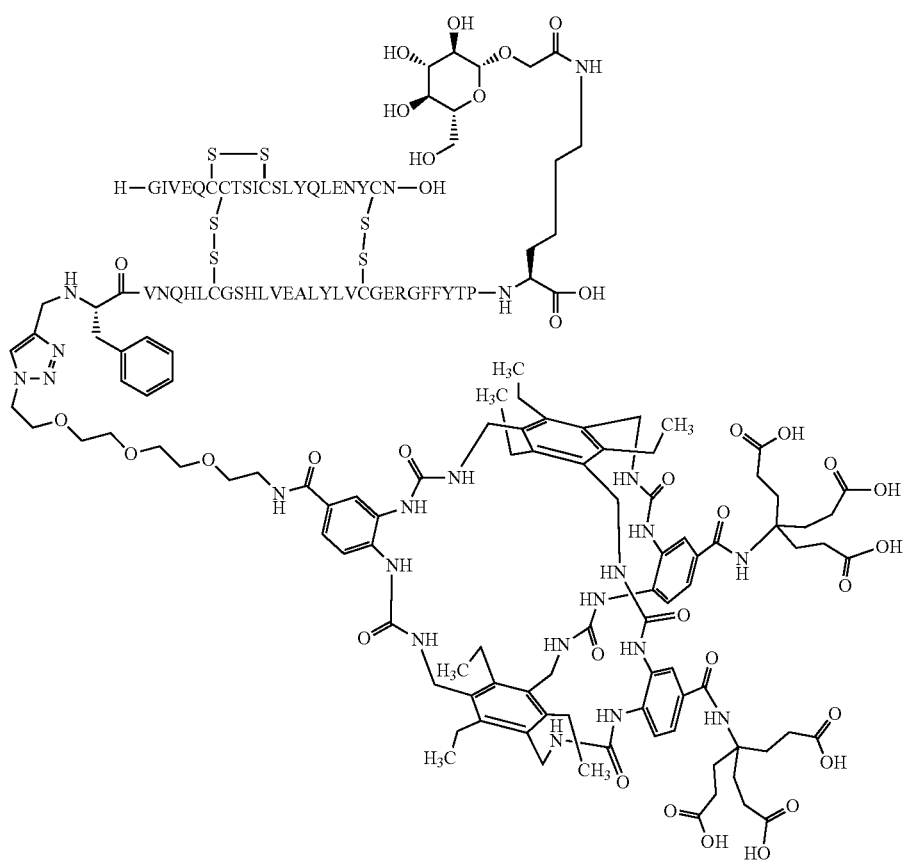
INS39
INS39 was prepared as INS18 using 1-acetyl-glycoside and G1macrocycle PEG4 azide 16. The product was purified by HPLC as described for INS1. LCMS measured 1934.4 [M+4H]$^{4+}$, calculated 1934.7.

Example 24:
B1-Methyl-Triazolyl-PEG3-G1macrocycle B29Nε-Acetyl-Glycoside desB30 Human Insulin
INS40
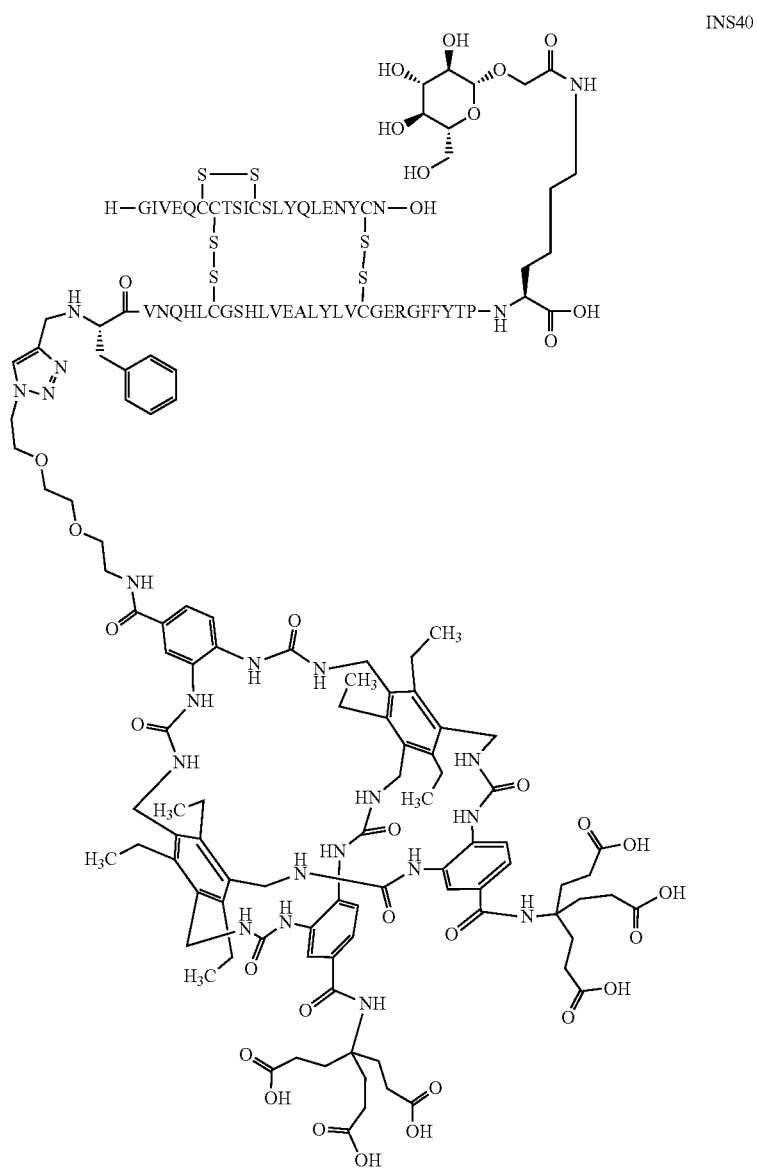
INS40
INS40 was prepared as INS18 using 1-acetyl-glycoside and G1macrocycle PEG3 azide 20. The product was purified by HPLC as described for INS1. LCMS measured 1923.6 $[M+4H]^{4+}$, calculated 1923.6.

Example 25: B29-Propanyol-Triazolyl-Propyl-G1macrocycle A1-Acetyl-Glycoside desB30 Human Insulin INS41

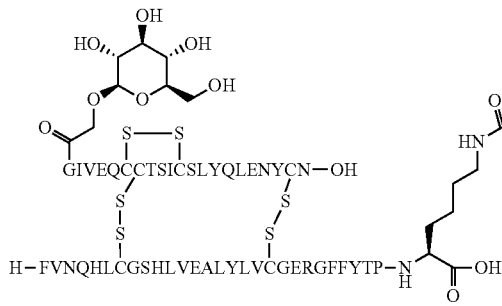
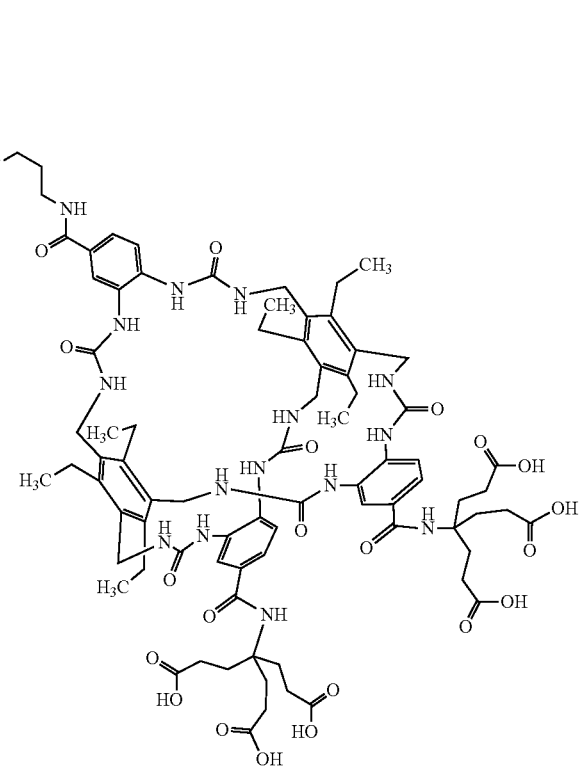

DesB30 human insulin var reacted at B29 with succinimidyl 4-pentynate (pH 10.5), and at A1 with succinimidyl O-peracetyl-1-acetyl-glucoside (pH 8.5), product purified by HPLC as described for INS1. The 0-acetyls were removed by saponification using 1:1 MeOH+100 mM aqueous sodium carbonate. The product was reacted with G1macrocycle propyl azide 21 as for INS31. The product was purified by HPLC as described for INS1. LCMS measured 1532.7 $[M+5H]^{5+}$, calculated 1532.7.

Glucose Sensitive Insulin Receptor Activation

Example 26: Glucose Affinity of Macrocycles by Fluorescence Titration

The optic properties (fluorescence) of the given macrocycle changes between the unbound state, and the glucose-bound state. Titrating the macrocycle with glucose in the relevant glucose concentration range, and measuring the changes in fluorescence of the system can thus give binding curves for binding to glucose, which can be used to determine the glucose binding constant, Ka (and the displacement constant, Kd).

All solutions were maintained at pH 7.4 using 10 mM Phosphate buffer solution. The titration was performed using a Horiba Scientific Duetta fluorescence spectrometer with an excitation wavelength of 310 nm and monitoring emission from 320-550 nm. The excitation and emission slit width/band widths were set to 5 nm. All points were acquired using a 0.5 second integration time and 5 accumulations.

Solution 1—Stock Solution of Compound 6d:

2 mg of compound 6d (Mw=3540 g/mol) was dissolved in 5.6 mL of ultrapure H2O (pH 7.4, 10 mM PB). The purity of Compound 6d was previously assayed by 1H NMR spectroscopy using a known concentration of DMF in D2O as an internal standard. The purity was calibrated at 80% (40 µM). This was then diluted by a four-fold to give a 10 µM solution of Compound 6d.

Solution 2—Stock Solution of D-Glucose and Compound 6d:

D-glucose (180.16 mg) was dissolved in 1 mL 10 mM PB and allowed to stand overnight to allow for equilibration of the a and 13 anomers. This was sequentially diluted to give a 20 mM stock solution of D-glucose. 250 µL of this solution was combined with 250 µL Compound 6d stock solution to give a 10 mM D-glucose/5 µM Compound 6d.

In a 3 mL cuvette, 1500 µL of Solution 1 was diluted with 1500 µL of 10 mM phosphate buffer to give a 5 µM solution. This was titrated with Solution 2. For each addition of titrant solution (Solution 2), the equivalent volume was removed from the cuvette prior to addition to keep the cell volume constant (3000 µL). Each addition was stirred for 1 minute then stirring stopped to allow 1 minute for the sample to equilibrate before acquisition. Additions (in µL): 0, 10, 10, 10, 10, 10, 20, 20, 50, 100, 100.

Figure 2:
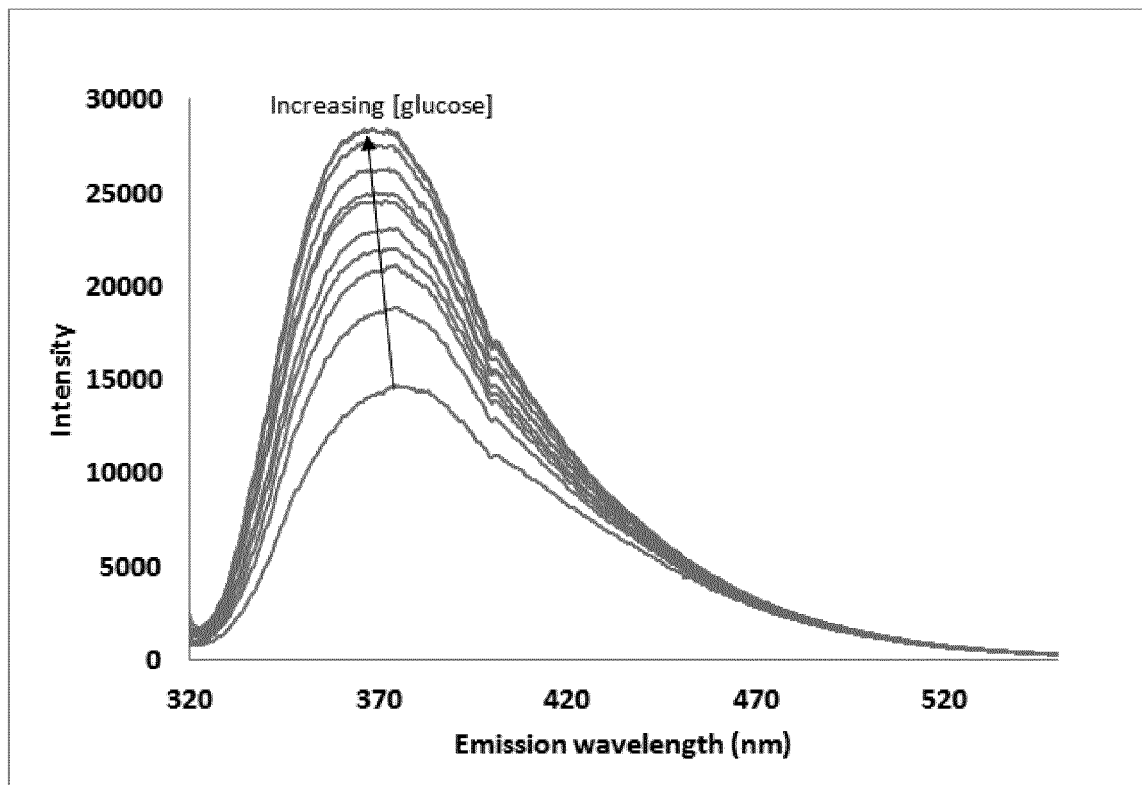
FIG. 2 shows fluorescence titration (λex=310 nm) of compound 6d (5 µM) titrated with D-glucose (10 mM) in 10 mM phosphate buffer.

Data is shown in FIG. 2 and FIG. 3.

Calculated Ka=14751.48±637.3 M-1; Kd compound 6d=1/14751 M-1=68 uM.

Glucose affinities were measured similarly for compound 21, Kd=89 uM compound 22, Kd=132 uM compound 23, Kd=78 uM compound 24, Kd=131 uM The macrocycles all bind glucose with affinity near 100 uM (Kd), no matter which linkers they are equipped with.

Example 27: Assay to Determine Affinity to the Human Insulin Receptor (hIR-A) in Absence or Presence of Glucose To measure the glucose sensitivity of the insulin derivatives, the affinity of the insulin derivatives towards the human insulin receptor was measured in the presence of no glucose or 20 mM glucose.

Insulin Receptor preparation

BHK cells over-expressing human Insulin Receptor A (hIR-A) was lysed in 50 mM Hepes pH 8.0, 150 mM NaCl, 1% Triton X-100, 2 mM EDTA and 10% glycerol. The cleared cell lysate was batch absorbed with wheat germ agglutinin (WGA)-agarose (Lectin from Triticum vulgaris-Agarose, L1394, Sigma-Aldrich Steinheim, Germany) for 90 minutes. The receptors were washed with 20 volumes 50 mM Hepes pH 8.0, 150 mM NaCl and 0.1% Triton X-100, where after the receptors were eluted with 50 mM Hepes pH 8.0, 150 mM NaCl, 0.1% Triton X-100, 0.5 M n-Acetyl Glucosamine and 10% glycerol. All buffers contain Complete (Roche Diagnostic GmbH, Mannheim, Germany).

Scintillation Proximity Assay (SPA) Binding Assay

SPA PVT anti-mouse beads (Perkin Elmer) were diluted in SPA binding buffer, consisting of 100 mM Hepes, pH 7.4, 100 mM NaCl, 10 mM $MgSO_4$, 0.025% (v/v) Tween-20. SPA beads were incubated with the IR-specific antibody 83-7 and solubilized semi-purified hl R-A. Receptor concentrations were adjusted to achieve 10% binding of 5000 cpm $^{125}$I-(Tyr31)-Insulin (Novo Nordisk A/S). Dilution series of cold ligands were added to 96 well Optiplate, followed by tracer ($^{125}$I-Insulin, 5000 cpm/well) and lastly receptor/SPA mix. In order to test the glucose sensitivity the binding experiments were set up in absence or presence of 20 mM glucose. The plates were rocked gently for 22.5 hours at 22° C., centrifuged for 5 minutes at 1000 rpm and counted in TopCounter (Perkin Elmer). The relative affinities for the analogues compared to human insulin were calculated and the increase in relative affinity from 0 to 20 mM glucose reflects the glucose sensitivity of the analogues (Glucose Factor). The experiments were performed in presence of 1.5% human serum albumin.

Data are shown in table 1.

The results show that the insulin derivatives of the present invention (insulin with glucose sensitive switches composed of glucose binder macrocycle in one position, plus glucoside in another position) have higher insulin receptor affinities in presence of 20 mM glucose than when no glucose is present. INS27, INS31, INS39, and INS40 show the weakest glucose sensitivity, demonstrating that the length of the linker affects the glucose sensitivity of the insulin conjugates.

TABLE 1

Relative insulin receptor binding affinity in the absence and presence of glucose (20 mM)

| Insulin derivative | Example no | hIRA SPAsol [Kd apparent relative (%)] | hIRA SPAsol incl. 20 mM glucose [Kd apparent relative (%)] | hIRA SPAsol [20 mM Glucose Factor (ratio)] |
|---|---|---|---|---|
| INS1 | 1 | 3.89 | 6.92 | 1.78 |
| INS9 | 5 | 2.29 | 5.97 | 2.60 |
| INS18 | 8 | 2.10 | 7.40 | 3.53 |
| INS21 | 9 | 1.47 | 4.57 | 3.12 |
| INS22 | 10 | 0.25 | 0.85 | 3.40 |
| INS28 | 12 | 2.64 | 8.64 | 3.31 |
| INS29 | 13 | 0.39 | 0.76 | 1.94 |
| INS30 | 14 | 2.72 | 7.91 | 2.94 |
| INS32 | 16 | 0.11 | 0.40 | 3.47 |
| INS33 | 17 | 0.17 | 0.61 | 3.24 |
| INS34 | 18 | 2.75 | 6.38 | 2.33 |
| INS35 | 19 | 1.63 | 6.88 | 4.21 |
| INS36 | 20 | 1.32 | 6.89 | 4.41 |
| INS37 | 21 | 2.39 | 8.35 | 3.50 |
| INS38 | 22 | 5.39 | 33.30 | 5.98 |
| INS41 | 25 | 0.42 | 3.11 | 7.41 |
| INS27 | 11 | 5.23 | 8.39 | 1.61 |
| INS31 | 15 | 9.35 | 9.37 | 1.00 |
| INS39 | 23 | 13.99 | 17.12 | 1.22 |
| INS40 | 24 | 14.07 | 16.76 | 1.20 |

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. An insulin derivative comprising human insulin or a human insulin analogue, a glucose mimetic and a macrocycle M of Formula M1:

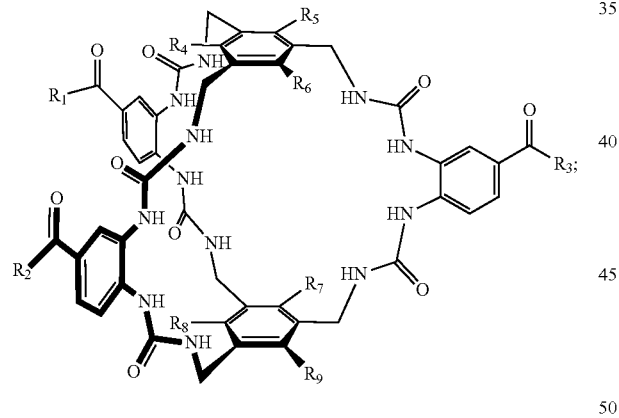

Formula M1 wherein $R_1$ and $R_2$ are independently selected from —OH,

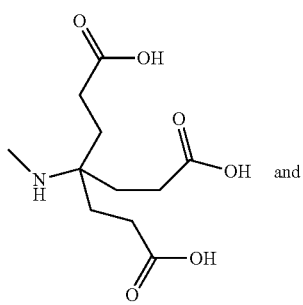

and wherein $R_4$, $R_5$, $R_6$, $R_7$, $R_8$, and $R_9$ are independently selected from hydrogen, halogen, (1-4C) alkyl and (1-4C) alkoxy; and wherein $R_3$ denotes the attachment point of the macrocycle of Formula M1.

2. The insulin derivative according to claim 1, wherein the glucose mimetic is beta-D-glucopyranoside.

3. The insulin derivative according to claim 2, wherein the macrocycle and the glucose mimetic, respectively, each is attached via an optional linker to the human insulin or human insulin analogue, wherein the points of attachment to human insulin or the human insulin analogue are selected from:

a) the alpha amino group of the amino acid residue in position 1 of the A-chain of human insulin or the human insulin analogue;

b) the alpha amino group in position 1 of the B-chain of human insulin or the human insulin analogue; and c) the epsilon amino group or the alpha carboxylic acid group of the lysine (K) in position 29 of the B-chain of the human insulin or human insulin analogue;

provided that the macrocycle and the glucose mimetic are not attached to the same attachment point on human insulin or the human insulin analogue.

4. The insulin derivative according to claim 3, wherein the macrocycle is attached to the alpha amino group in position 1 of the B-chain of human insulin or the human insulin analogue; and wherein the glucose mimetic is attached to the epsilon amino group of the lysine (K) in position 29 of the B-chain of the human insulin or human insulin analogue.

5. The insulin derivative according to claim 4, wherein the macrocycle M is attached via a linker to the human insulin or human insulin analogue, wherein said linker is of Formula L1

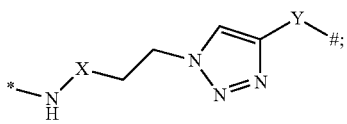

Formula L1 wherein X is CH$_2$— or (CH$_2$CH$_2$O—)$_p$, wherein p is an integer from 2 to 4;

wherein Y is CH$_2$—, (CH$_2$CH$_2$CO—), or -Ph-para-CH$_2$—;

wherein * denotes the attachment point to the macrocycle M; and wherein # denotes the attachment point to human insulin or the human insulin analogue.

6. The insulin derivative according to claim 5, wherein the glucose mimetic is attached via a linker to the human insulin or human insulin analogue, wherein said linker is of Formula L2:

"—(CH$_2$CH$_2$O—)$_q$—(CH$_2$)$_r$—C(O)—#;

wherein q is 1 or 2;

wherein r is 1 or 2;

wherein " denotes the attachment point to the glucose mimetic; and wherein # denotes the attachment point to human insulin or the human insulin analogue.

7. The insulin derivative according to claim 1, wherein the insulin derivative comprises two glucose mimetics and two macrocycles M of Formula M1.

8. The insulin derivative according to claim 7, wherein the two macrocycles are attached to the alpha amino group in position 1 of the B-chain of human insulin or the human insulin analogue.

9. The insulin derivative according to claim 8, wherein the two macrocycles M are attached via a trivalent linker to the alpha amino group in position 1 of the B-chain of human insulin or the human insulin analogue, wherein said linker is of Formula L3

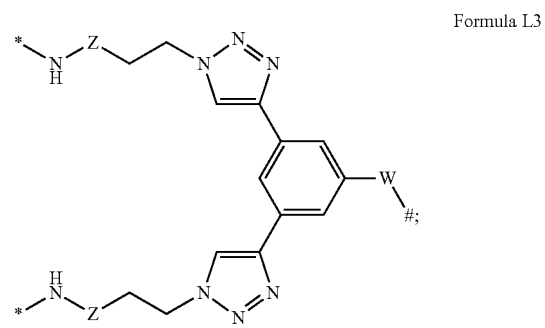

Formula L3 wherein Z is CH$_2$— or (CH$_2$CH$_2$O—)$_3$;

wherein W is CH$_2$—, (CH$_2$CH$_2$CO—), or -Ph-para-CH$_2$—;

wherein * denotes the attachment point to the macrocycle M; and wherein # denotes the attachment point to human insulin or the human insulin analogue.

10. The insulin derivative according to claim 9, wherein the two glucose mimetics are attached via a trivalent linker attached to the alpha carboxylic acid group or the epsilon amino group of the lysine (K) in position 29 of the B-chain of the human insulin or human insulin analogue;

wherein said linker is selected from the group of a)

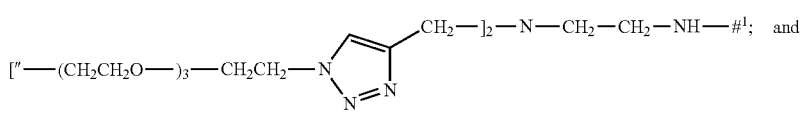

Formula L4 b)

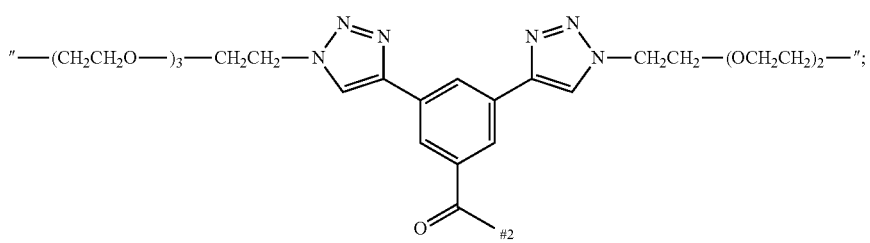

Formula L5 or wherein the two glucose mimetics are each attached via a bivalent linker attached to the alpha carboxylic acid group and the epsilon amino group of the lysine (K), respectively, in position 29 of the B-chain of the human insulin or human insulin analogue;

wherein said linkers are of Formula L6 and Formula L7:

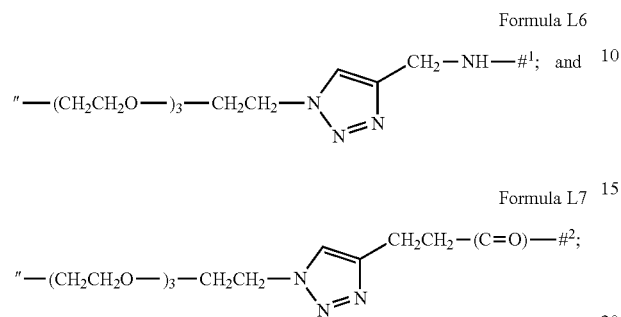

wherein " denotes the attachment point to the glucose mimetic; and wherein #$^1$ denotes the attachment point to the alpha carboxyl acid group of the lysine (K) in position 29 of the B-chain of the human insulin or human insulin analogue; and wherein #$^2$ denotes the attachment point to the epsilon amino group of the lysine (K) in position 29 of the B-chain of the human insulin or human insulin analogue.

11. The insulin derivative according to claim 1, wherein the glucose mimetic is attached to the alpha amino group of the amino acid residue in position 1 of the A-chain of human insulin or the human insulin analogue.

12. An insulin derivative selected from the group consisting of

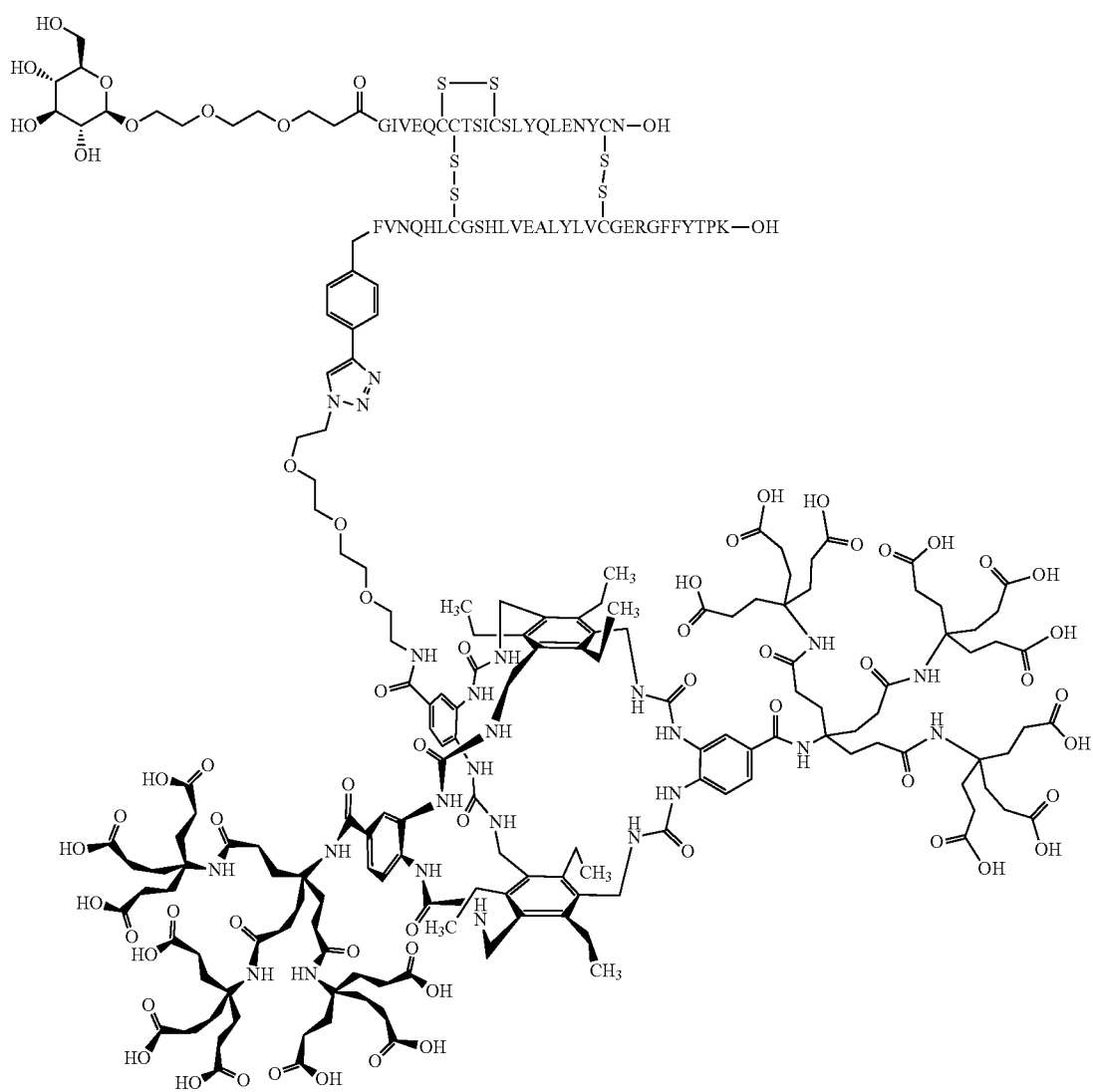

INS4 of Example 2;

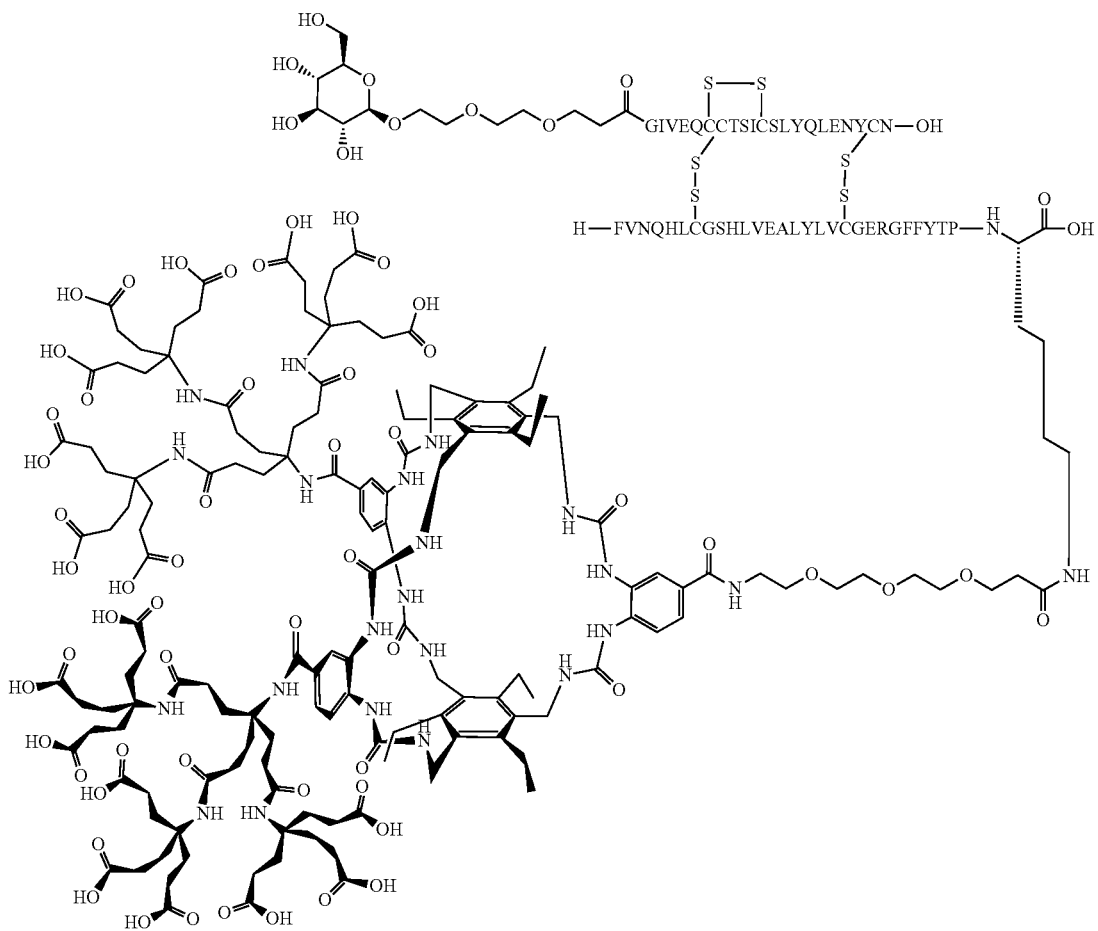
INS5 of Example 3; and

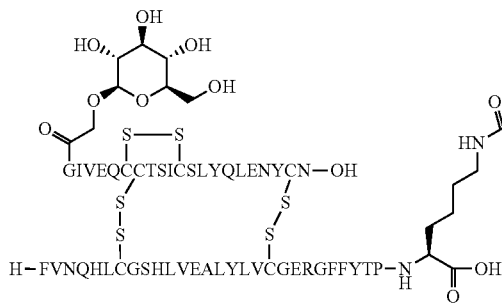
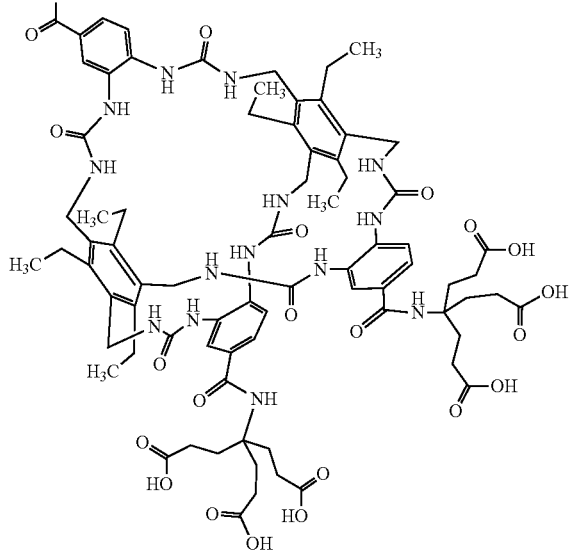

INS41 of Example 25.

13. A pharmaceutical composition comprising a therapeutically effective amount of an insulin derivative according to claim 1 and a pharmaceutically acceptable excipient.

14. A method of treating a disease comprising administering an insulin derivative according to claim 1 to a patient in need thereof, wherein said disease is selected from the group consisting of diabetes, impaired glucose tolerance, hyperglycemia and metabolic syndrome.

15. A method of treating Type 1 diabetes or Type 2 diabetes comprising administering an insulin derivative according to claim 1 to a patient in need thereof.

16. A method of treating metabolic syndrome X or insulin resistance syndrome comprising administering an insulin derivative according to claim 1 to a patient in need thereof.

17. The insulin derivative according to claim 3, wherein the insulin derivative comprises two glucose mimetics and two macrocycles M of Formula M1.

18. The insulin derivative according to claim 3, wherein the glucose mimetic is attached to the alpha amino group of the amino acid residue in position 1 of the A-chain of human insulin or the human insulin analogue.

19. A pharmaceutical composition comprising a therapeutically effective amount of an insulin derivative according to claim 12 and a pharmaceutically acceptable excipient.

20. A method of treating a disease comprising administering an insulin derivative according to claim 12 to a patient in need thereof, wherein said disease is selected from the group consisting of diabetes, impaired glucose tolerance, hyperglycemia and metabolic syndrome.

21. A method of treating diabetes comprising administering an insulin derivative according to claim 12 to a patient in need thereof.

22. The method of claim 21, wherein diabetes is Type 1 diabetes or Type 2 diabetes.

23. A method of treating metabolic syndrome X or insulin resistance syndrome comprising administering an insulin derivative according to claim 12 to a patient in need thereof.

* * * * *